(12) United States Patent
Kim et al.

(10) Patent No.: US 9,435,807 B2
(45) Date of Patent: Sep. 6, 2016

(54) USE OF LEUCYL TRNA SYNTHETASE

(71) Applicant: Medicinal Bioconvergence Research Center, Suwon-si (KR)

(72) Inventors: Sunghoon Kim, Seoul (KR); Jung Min Han, Seoul (KR)

(73) Assignee: Medicinal Bioconvergence Research Center, Suwon-si (KR)

( * ) Notice: Subject to any disclaimer, the term of this patent is extended or adjusted under 35 U.S.C. 154(b) by 0 days.

(21) Appl. No.: 14/223,188

(22) Filed: Mar. 24, 2014

(65) Prior Publication Data

US 2014/0249045 A1 Sep. 4, 2014

Related U.S. Application Data

(63) Continuation of application No. PCT/KR2012/007656, filed on Sep. 24, 2012.

(30) Foreign Application Priority Data

Sep. 22, 2011 (KR) ........................ 10-2011-0095893

(51) Int. Cl.
*G01N 33/573* (2006.01)
*G01N 33/574* (2006.01)
*C12N 15/113* (2010.01)

(52) U.S. Cl.
CPC ......... *G01N 33/573* (2013.01); *C12N 15/1137* (2013.01); *C12Y 601/01004* (2013.01); *G01N 33/574* (2013.01); *C12N 2310/14* (2013.01); *G01N 2800/044* (2013.01)

(58) Field of Classification Search
CPC ............. G01N 33/573; G01N 33/574; C12N 15/1137; C12Y 601/01004
See application file for complete search history.

(56) References Cited

U.S. PATENT DOCUMENTS

| | | |
|---|---|---|
| 4,366,241 A | 12/1982 | Tom et al. |
| 4,376,110 A | 3/1983 | David et al. |
| 4,517,288 A | 5/1985 | Giegel et al. |
| 4,837,168 A | 6/1989 | De Jaeger et al. |
| 5,583,973 A | 12/1996 | DeLisi et al. |
| 5,612,894 A | 3/1997 | Wertz |

FOREIGN PATENT DOCUMENTS

| | | |
|---|---|---|
| WO | 91/18980 | 12/1991 |
| WO | 93/06121 | 4/1993 |
| WO | 94/08051 | 4/1994 |
| WO | 95/12608 | 5/1995 |

(Continued)

OTHER PUBLICATIONS

Guertin, D. et al. An expanding role for mTOR in cancer. Trends in Molecular Medicine 11: 353-361 (2005).*

(Continued)

*Primary Examiner* — Gail R Gabel
(74) *Attorney, Agent, or Firm* — H.C. Park & Associates, PLC

(57) ABSTRACT

Provided is a method of screening for agents for preventing or treating mTORC 1 mediated diseases by screening test agents to determine test agents that inhibit the binding ability of LRS to RagD, or RagD GTPases, and a method of reducing cell size as compared to the control group, including inhibiting the expression of intracellular LRS in the cells.

1 Claim, 33 Drawing Sheets

(56) References Cited

FOREIGN PATENT DOCUMENTS

| | | |
|---|---|---|
| WO | 95/30642 | 11/1995 |
| WO | 95/35503 | 12/1995 |

OTHER PUBLICATIONS

Um et al. Absence of S6K1 protects against age- and diet-induced obesity while enhancing insulin sensitivity, Nature, 431: 200-205 (2004).*

Han et al. Leucyl-tRNA Synthetase is an Intracellular Leucine Sensor for the mTORC1-Signaling Pathway. Cell 49: 410-424 (Apr. 2012).*

Sancak et al. The Rag GTPases bind raptor and mediate amino acid signaling to mTORC1. Science 320: 1496-1501 (2008).*

Roccio et al., "Regulation of the small GTPase Rheb by amino acids", Oncogene, 2006, p. 657-664, vol. 25.

Park et al., "Aminoacyl tRNA synthetases and their connections to disease", Proceedings of the National Academy of Sciences, Aug. 12, 2008, p. 11043-11049, vol. 105, No. 32.

Crozier et al., "Oral Leucine Administration Stimulates Protein Synthesis in Rat Skeletal Muscle", The Journal of Nutrition, 2005, p. 376-382.

Sekiguchi et al., "Novel G Proteins, Rag C and Rag D, Interact with GTP-binding Proteins, Rag A and Rag B", Journal of Biological Chemistry, Mar. 9, 2001, p. 7246-7257, vol. 276, No. 10.

Eriani et al., "Partition of tRNA synthetases into two classes based on mutually exclusive sets of sequence motifs", Nature, Sep. 13, 1990, p. 203-206, vol. 347.

Ma et al., "Molecular mechanisms of mTOR-mediated translational control", Nature Reviews Molecular Cell Biology, May 2009, p. 307-318, vol. 10.

Tee et al., "Tuberous Sclerosis Complex Gene Products,Tuberin and Hamartin,Control mTOR Signaling by Acting as a GTPase-Activating Protein Complex toward Rheb" Current Biology, Aug. 5, 2003, p. 1259-1268, vol. 13.

Fernandes, "Technological advances in high-throughput screening", Current Opinion in Chemical Biology, 1998, p. 597-603, vol. 2.

Sancak et al., "Ragulator-Rag Complex Targets mTORC1 to the Lysosomal Surface and is Necessary for Its Activation by Amino Acids", Cell, Apr. 16, 2010, p. 290-303, vol. 141.

Holz, et al., "mTOR and S6K1 Mediate Assembly of the Translation Preinitiation Complex through Dynamic Protein Interchange and Ordered Phosphorylation Events", Cell, Nov. 18, 2005, p. 569-580, vol. 123.

Schurmann, et al., "Cloning of a Novel Family of Mammalian GTP-binding Proteins (RagA, RagBs, RagBl) with Remote Similarity to the Ras-related GTPases", Journal of Biological Chemistry, Dec. 1, 1995, p. 28982-28988, vol. 270, No. 48.

Kim, et al., "Regulation of TORC1 by Rag GTPases in nutrient response", Nature Cell Biology, Aug. 2008, p. 935-945, vol. 10, No. 8.

Sancak, et al., "The Rag GTPases Bind Raptor and Mediate Amino Acid Signaling to mTORC1", Science, Jun. 13, 2008, p. 1496-1501, vol. 320.

Bucci, et al., "Rab7: A Key to Lysosome Biogenesis", Molecular Biology of the Cell, Feb. 2000, p. 467-480, vol. 11.

Park, et al., "Functional expansion of aminoacyl-tRNA synthetases and their interacting factors: new perspectives on housekeepers", TRENDS in Biochemical Sciences, Oct. 2005, p. 569-574, vol. 30, No. 10.

Burbaum et al., "Structural Relationships and the Classification of Aminoacyl-tRNA Synthetases", The Journal of Biological Chemistry, Sep. 15, 1991, p. 16965-16968, vol. 266, No. 26.

Arnez et al., "Structural and functional considerations of the aminoacylation reaction", Trends in Biochemical Sciences, Jun. 1997, p. 211-216, vol. 22.

Cusack et al., "Sequence, structural and evolutionary relationships between class 2 aminoacyl-tRNA synthetases", Nucleic Acids Research, 1991, p. 3489-3498, vol. 19, No. 13.

Shaw, "mTOR signaling: RAG GTPases transmit the amino acid signal", Trends in Biochemical Sciences, 2008, p. 565-568, vol. 33, No. 12.

Lee et al., "Aminoacyl-tRNA synthetase complexes: beyond translation", Journal of Cell Science, 2004, p. 3725-3734, vol. 117.

Eriani, et al. "Aspartyl-tRNA synthetase from *Escherichia coli*: cloning and characterization of the gene, homologies of its translated amino acid sequence with asparaginyl -and lysyl-tRNA synthetases", Nucleic Acids Research, 1990, p. 7109-7118.

Ling et al., "The C-terminal Appended Domain of Human Cytosolic Leucyl-tRNA Synthetase Is Indispensable in Its Interaction with Arginyl-tRNA Synthetase in the Multi-tRNA Synthetase Complex", The Journal of Biological Chemistry, Oct. 14, 2005, p. 34755-34763, vol. 280, No. 41.

Um, et al. "Absence of S6K1 protects against age- and diet- induced obesity while enhancing insulin sensitivity", Nature, Sep. 9, 2004, p. 200-206, vol. 431.

Cho, et al. "Regulation of adipocyte differentiation and insulin action with rapamycin", Biochemical and Biophysical Research Communications, 2004, p. 942-948, vol. 321.

Ko et al., "Nucleolar Localization of Human Methionyl-tRNA Synthetase and Its Role in Ribosomal RNA Synthesis", Journal of Cell Biology, May 1, 2000, p. 567-574, vol. 149.

Kim, et al. "Regulation of Peroxisome Proliferator-Activated Receptor-γ Activity by Mammalian Target of Rapamycin and Amino Acids in Adipogenesis", Diabetes, Nov. 2004, p. 2748-2756, vol. 53.

Guertin, et al. "An expanding role for mTOR in cancer", Trends in Molecular Medicine, Jul. 5, 2005, p. 353-361, vol. 11, No. 8.

Li, et al., "Human Mitochondrial Leucyl-tRNA Synthetase Corrects Mitochondrial Dysfunctions Due to the tRNALeu (UUR) A3243G Mutation, Associated with Mitochondrial Encephalomyopathy, Lactic Acidosis, and Stroke-Like Symptoms and Diabetes", Molecular and Cellular Biology, May 2010, p. 2147-2154, vol. 30, No. 9.

Hitzeman, et al. "Isolation and Characterization of the Yeast 3-Phosphoglycerokinase Gene (PGK) by an Immunological Screening Technique", Journal of Biological Chemistry, Dec. 25, 1980, p. 12073-12080, vol. 255, No. 24.

Schultz, et al. "High Throughput Purification of Combinatorial Libraries", Bioorganic and Medicinal Chemistry Letters, 1998, p. 2409-2414, vol. 8.

Sittampalam, et al. "High-Throughput Screening: Advances in Assay Technologies", Current Opinion in Chemical Biology, 1997, p. 384-391, vol. 1.

Tsang, et al. "Targeting Mammalian Target of Rapamycin (mTOR) for Health and Diseases", Drug Discovery Today, Feb. 2007, p. 112-124, vol. 12, No. 3/4.

McLaughlin, et al. "CAG Trinucleotide RNA Repeats Interact with RNA-Binding Proteins", American Journal of Human Genetics, 1996, p. 561-569, vol. 59.

Tang, et al. "Human pro-Tumor Necrosis Factor is a Homotrimer", Biochemistry, 1996, p. 8216-8225, vol. 35.

Lingner, et al. "Purification of telomerase from Euplotes aediculatus: Requirement of a primer 3' overhang", Proceedings of the National Academy of Sciences of the USA, Oct. 1996, p. 10712-10717, vol. 93.

Chodosh, et al. "A Single Polypeptide Possesses the Binding and Transcription Activities of the Adenovirus Major Late Transcription Factor", Molecular and Cellular Biology, Dec. 1986, p. 4723-4733, vol. 6, No. 12.

Bevan, et al. "Identifying small-molecule lead compounds: the screening approach to drug discovery", Trends in Biotechnology, Mar. 1995, p. 115-121, vol. 13.

Morel, et al. "Monoclonal Antibodies to Bovine Serum Albumin: Affinity and Specificity Determinations", Molecular Immunology, 1988, p. 7-15, vol. 25, No. 1.

Cheung, et al. "Epitope-Specific Antibody Response to the Surface Antigen of Duck Hepatitis B Virus in Infected Ducks", Virology, 1990, p. 546-552, vol. 176.

(56) References Cited

OTHER PUBLICATIONS

Fingar, et al. "Mammalian cell size is controlled by mTOR and its downstream targets S6K1 and 4EBP1/eIF4E", Genes and Development, 2002, p. 1472-1487, vol. 16.

Kim, et al. "Downregulation of FUSE-binding protein and c-myc by tRNA synthetase cofactor p38 is required for lung cell differentiation", Nature Genetics, Jul. 2003, p. 330-336, vol. 34, No. 3.

Lynch, et al. "Regulation of Amino Acid-Sensitive TOR Signaling by Leucine Analogues in Adipocytes", Journal of Cellular Biochemistry, Mar. 2000, p. 234-251, vol. 77.

Wang, et al. "Autophagy in Cellular Growth Control", Federation of European Biochemical Studies Letters, Jan. 22, 2010, p. 1417-1426, vol. 584.

Xin, et al. "The 'KMSKS' Motif in Tyrosyl-tRNA Synthetase Participates in the Initial Binding of tRNATyr", Biochemistry, Dec. 17, 1999, p. 340-347, vol. 39, No. 2.

Vaughan, et al. "Control of Initiation of Protein Synthesis in Human Cells", Journal of Biological Chemistry, Oct. 25, 1973, p. 7087-7096, vol. 248, No. 20.

Cusack et al., "The 2 Angstrom crystal structure of leucyl-tRNA synthetase and its complex with a leucyl-adenylate analogue", The EMBO Journal, 2000, p. 2351-2361, vol. 19, No. 10.

Lee, et al., "The Function of Lysyl-tRNA Synthetase and Ap4A as Signaling Regulators of MITF Activity in FceRI-Activated Mast Cells", Immunity, Feb. 2004, p. 145-151, vol. 20.

Yannay-Cohen et al., "LysRS Serves as a Key Signaling Molecule in the Immune Response by Regulating Gene Expression", Molecular Cell, Jun. 12, 2009, p. 603-611, vol. 34.

Shin, et al., "Implication of leucyl-tRNA synthetase 1 (LARS1) over-expression in growth and migration of lung cancer cells detected by siRNA targeted knock-down analysis", Experimental and Molecular Medicine, Apr. 2008, p. 229-236, vol. 40, No. 2.

T Hart, et al., "Evidence that the Mitochondrial Leucyl tRNA Synthetase (LARS2) Gene Represents a Novel Type 2 Diabetes Susceptibility Gene", Diabetes, Jun. 2005, p. 1892-1895, vol. 54.

Stipanuk, "Leucine and Protein Synthesis: mTOR and Beyond", Nutrition Reviews, Mar. 2007, p. 122-129, vol. 65, No. 3.

Bhaskar et al., "The Two TORCs and Akt", Developmental Cell, Apr. 2007, p. 487-502.

* cited by examiner

HEK-293T cell

HeLa cell

KMSKS motif

| Substrates | Constants | LRS WT ||
| --- | --- | --- | --- |
| | | ATP-PPi exchange | Leucylation |
| Leucine | $K_m$ (mM) | 0.143 ± 0.061 | 0.0159 ± 0.0004 |
| | $k_{cat}$ ($S^{-1}$) | 0.16 ± 0.07 | 0.368 ± 0.009 |
| | $k_{cat}/K_m$ ($S^{-1}mM^{-1}$) | 1.16 ± 0.49 | 22.9 ± 0.57 |

USE OF LEUCYL TRNA SYNTHETASE

CROSS REFERENCE TO RELATED APPLICATIONS

This application is a continuation of International Application No. PCT/KR2012/007656, filed Sep. 24, 2012, and claims priority from Korean Patent Application No. 10-2011-0095893, filed Sep. 22, 2011, all of which are hereby incorporated by reference for all purposes as if fully set forth herein.

BACKGROUND OF THE INVENTION

1. Field

The present invention relates to novel use of leucyl tRNA synthetase and more particularly it relates a method of screening an agent for preventing or treating mTORC1 mediated diseases by screening an test agent which inhibits binding ability of LRS to RagD or RagD GTPases, and a method of reducing cell size as compared to the control group, comprising inhibiting expression of intracellular LRS.

2. Discussion of the Background

A leucine is one of three branched chain amino acids. Unlike other amino acids, leucine and the other branched chain amino acids, isoleucine and valine, escape liver metabolism due to the defect of the branched chain amino acid aminotransferase and directly influence muscle protein synthesis. Leucine not only serves as a substrate for protein synthesis but also is recognized as a potent signal nutrient that regulates protein metabolism. Oral administration of leucine increases rates of skeletal muscle protein synthesis in rats (Crozier S J, et. al., J Nutr. 135 (2005), 376382) and removal of leucine from a complete meal prevents stimulation of protein synthesis (Stipanuk M H., Nutr Rev. 65 (2007), 122129). Leucine-induced protein synthesis is mediated by the mammalian target of rapamycin (mTOR) complex 1 (mTORC1), which is composed of mTOR, regulatory associated protein of mammalian target of rapamycin (Raptor), G-protein βsubunit-like protein (GβL), and ras homolog enriched in brain (Rheb) (Bhaskar P T, et. al., Dev Cell. 12 (2007), 487502). mTORC1 phosphorylates S6K and 4E-BP, the rate-limiting step in translation, resulting in the translation initiation of mRNAs displaying a 5' cap structure (Ma X M, Nat Rev Mol Cell Biol., 10(2009), 307-318; Holz M K, et. al., Cell 123(2005), pp 569-580).

mTORC1 regulates translation and cell growth by coordinating several upstream inputs such as growth factors, intracellular energy status, and amino acid availability. The Tuberous Sclerosis Complex (TSC) 1 and TSC2 regulate GTP/GDP exchange of Ras-like GTPase, Rheb to transmit growth factor and intracellular energy signals to mTORC1. When bound to GTP, Rheb interacts with and activates mTORC1 (Tee A R, et. al., Curr Biol. 13 (2003), 12591268) and appears to be necessary for the activation of mTORC1 by all signals, including amino acid availability. In contrast, TSC1-TSC2 is dispensable for the regulation of mTORC1 by amino acids, and, in cells lacking TSC2, the mTORC1 pathway is sensitive to amino acid starvation but resistant to growth factor withdrawal (Roccio M, et. al., Oncogene. 25 (2006), 657-664).

Recently, the Rag GTPases, which are also the members of the Ras family of GTP-binding proteins, were shown to be amino acid-specific regulators of the mTORC1 pathway (Sancak Y, et. al., Cell 141 (2010), 290-303). Mammals express four Rag proteins—RagA, RagB, RagC, and RagD—form heterodimers consisting of RagA or RagB with RagC or RagD. RagA and RagB, like RagC and RagD, are highly similar to each other and are functionally redundant (Schurmann A, et. al., J Biol Chem. 270 (1995), 28982-28988). Rag heterodimers containing GTP-bound RagB interact with mTORC1, and amino acids induce the mTORC1-Rag interaction by promoting the loading of RagB with GTP, which enables it to directly interact with the Raptor component of mTORC1 (Sancak Y, et. al., Cell 141 (2010), 290-303; Kim E, Nat Cell Biol. 10 (2008), 935-945). The activation of the mTORC1 pathway by amino acids correlates with the movement of mTORC1 from an undefined location to a compartment containing Rab7 (Sancak Y, et. al., Science 320 (2008), 1496-1501), a marker of both late endosomes and lysosomes (Bucci C, et. al., Mol Biol Cell., 11 (2000), 467-480). Recent report shows that amino acids induce the movement of mTORC1 to lysosome, where the Rag GTPases reside. Ragulator complex, which is composed of MAPKSP1, ROBLD3, and c11orf59 gene products, interacts with the Rag GTPases, recruits them to lysosomes and is essential for mTORC1 activation (Sancak Y, et. al., Cell 141 (2010), 290-303). However, how intracellular leucine is sensed for mTORC1 activation and how GTP/GDP cycles of Rag GTPases are regulated by amino acid for mTORC1 activation are unknown.

Aminoacyl-tRNA synthetases (ARSs) are essential enzymes for cellular protein synthesis and viability that catalyze the ligation of specific amino acids to their cognate tRNAs. The enzyme reaction is separated into two steps: the ATP-PPi exchange reaction for amino acid activation and aminoacylation of tRNA (Park S, et. al., Trends Biochem Sci. 30 (2005), 569-574). Based on amino acid sequence alignments and structural features, ARSs have been divided into two classes (Eriani G, et. al., Nature 347 (1990), 203-206; Burbaum J J, et. al., J Biol Chem. 266 (1991), 16965-16968). The class I synthetases share two consensus sequences, the HIGH (His-Ile-Gly-His) and KMSKS (Lys-Met-Ser-Lys-Ser) motifs, that form a nucleotide binding Rossmann fold (Arnez J G, et. al., Trends Biochem sci. 22 (1997), 211-216). In contrast, the class II synthetases do not contain the Rossmann fold, but share a very different catalytic domain (Cusack S, et. al., Nucl Acids Res. 19 (1991), 3489-3498). Leucyl-tRNA synthetase (LRS) is the class I enzyme, which is characterized by the HIGH and KMSKS motifs (Cusack S, et. al., EMBO J. 19 (2000), 2351-361). Structurally, LRS consists of the catalytic domain of bipartite Rossmann fold with a large insertion domain called CP1, a tRNA-binding anticodon domain, and a C-terminal extension domain (Cusack S, et. al., EMBO J. 19 (2000), 2351-361). In higher eukaryotic cells, LRS exists as a component of the ARS complex consisting of nine different tRNA synthetases and three non-enzymatic components, p18/AIMP3, p38/AIMP2, and p43/AIMP1 (Lee S W, et. al., J Cell Sci. 117 (2004), 3725-3734; Park S, et. al., Trends Biochem Sci. 30 (2005), 569-574; Park S G, et. al., Proc Natl Acad Sci USA 105 (2008), pp. 11043-11049). It has been shown that the C-terminal domain of LRS is crucial for the interaction with other components of the ARS complex (Ling C, et. al., J Biol Chem. 280 (2005), 34755-3463). Among the components of the complex, several different components are involved in various cell signaling processes (Lee Y N, et. al., Immunity 20 (2004), 145?51; Park S, et. al., Trends Biochem Sci. 30 (2005), pp. 569-574; Park S G, et. al., Proc Natl Acad Sci USA 105 (2008), pp. 11043-11049). For instance, glutamyl-prolyl-tRNA synthetase (EPRS) suppresses translation of the target inflammatory mRNAs by forming an interferon gamma-activated inhibitor of translation (GAIT) complex (Sampath P, et. al., Cell. 119 (2004), 195-208). Lysyl-tRNA synthetase (KRS) and its product, Ap4A, function as signaling regulators in the immune response by regulating gene expression (Lee Y N, et. al., Immunity 20 (2004), 145?51; Yannay-Cohen N, et. al., Mol Cell 34 (2009), 603-611). Methionyl-tRNA synthetase (MRS) and glutaminyl-tRNA synthetase (QRS) are involved in rRNA biogenesis (Ko et al., 2000) and anti-apoptotic signal regulation (Ko Y G, et. al., J Cell Biol 149 (2000), 567-574), respectively. Besides, cytosolic LRS was reported to be potentially implicated in lung cancer growth (Shin S H, et. al., Exp Mol Med. 40 (2008), 229-236), and the mitochondrial LRS may be involved in diabetes ('t Hart L M, et. al., Diabetes. 54 (2005), 1892-1895; Li R., et. al., Mol Cell Biol. 30 (2010), 2147-154).

SUMMARY

The present invention relates to novel uses of LRS and provides a method of screening an agent for preventing or treating mTORC1 mediated diseases and a method of reducing cell size as compared to a control group. Accordingly, the screening methods can be used for developing novel treatment agents for diseases such as cancer.

Accordingly, the inventors investigated non-canonical function of LRS apart from its catalytic function for protein synthesis. In this work, they found that LRS is an mTORC1-associated protein and plays an essential role for amino acid induced mTORC1 activation. In addition, ablation of leucine binding ability in LRS desensitized the mTORC1 pathway to amino acid. Among the components of mTORC1, they found that LRS directly interacts with Rag GTPase in amino acid-dependent manner and functions as a GTPase-activating protein (GAP) for Rag GTPase to activate mTORC1 and thereby completing the present invention.

Accordingly, an object of the present invention is to provide a method for screening agents for preventing or treating mTORC1-mediated diseases comprising the steps of:
(a) contacting LRS (Leucyl tRNA synthetase), RagD and a test agent with or without the test agent;
(b) comparing the binding affinity between LRS and RagD with the test agent to the binding affinity between LRS and RagD without the test agent; and
(c) measuring a change between the binding affinity between LRS and RagD.

Another object of the present invention is to provide a method of reducing cell size compared to the control group comprising inhibiting expression of intracellular LRS.

Another object of the present invention is to provide method for screening agents for preventing or treating mTORC1-mediated diseases comprising the steps of:
(a) contacting LRS (Leucyl tRNA synthetase), RagD and a test agent with or without the test agent;
(b) comparing the binding affinity between LRS and RagD with the test agent to the binding affinity between LRS and RagD without the test agent; and
(c) identifying the test agent inhibiting the binding affinity between LRS and RagD.

Aspects of the present invention provide a method for screening agents for preventing or treating mTORC1-mediated diseases comprising the steps of:
(a) contacting LRS (Leucyl tRNA synthetase), RagD and a test agent with or without the test agent;
(b) comparing the binding affinity between LRS and RagD with the test agent to the binding affinity between LRS and RagD without the test agent; and
(c) measuring a change in the binding affinity between LRS and RagD.

Aspects of the present invention provide a method of reducing cell size as compared to the control group, comprising inhibiting expression of intracellular LRS.

Aspects of the present invention provide a method for screening agents for preventing or treating mTORC1-mediated diseases comprising the steps of:
(a) contacting LRS (Leucyl tRNA synthetase), RagD and a test agent with or without the test agent;
(b) comparing the binding affinity between LRS and RagD with the test agent to the binding affinity between LRS and RagD without the test agent; and
(c) identifying the test agent inhibiting the binding affinity between LRS and RagD.

Hereinafter, the present invention will be described in more detail. The present invention first identified that leucyl-tRNA synthetase (LRS) plays a critical role in amino acid-induced mTORC1 activation. That is, they identified that LRS of the present invention directly binds to Rag GTPase, the mediator of amino acid signaling to mTORC1, in amino acid-dependent manner and functions as a GTPase-activating protein (GAP) for Rag GTPase to activate mTORC1.

The present inventors confirmed that leucyltRNA synthetase (LRS) plays a critical role in amino acid-induced mTORC1 activation and LRS senses intracellular leucine concentration and mediates leucine-induced mTORC1 activation. More particularly, they confirmed that LRS directly binds to Rag GTPase, the mediator of amino acid signaling to mTORC1, in amino acid-dependent manner and functions as a GTPase-activating protein (GAP) for Rag GTPase to activate mTORC1.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

FIG. 1a shows subcellular fractionation of LRS.

FIG. 1b shows immunofluorescence staining of LRS in HeLa cells.

FIG. 1c shows lysosomal localization of LRS.

FIG. 1d shows 293T cell lysates that were immunoprecipitated with anti-mTOR antibodies and the co-precipitated LRS and Raptor were determined by immunoblotting.

FIG. 1e shows (E) 293T cells that were transfected with control plasmid (EV), myc-tagged LRS, or MRS.

FIG. 1f shows co-localization of LRS with mTOR in HeLa cells.

FIG. 1g shows co-localization of LRS with Raptor in HeLa cells.

FIG. 2a shows 293T cells that were transfected with 6 kinds of LRS siRNA.

FIG. 2b shows 293T cells that were transfected with control, mTOR, LRS, IRS, MRS, or VRS siRNA.

FIG. 2c shows 293T cells that were transfected with control, LRS, IRS, MRS, or VRS siRNA.

FIG. 2d shows 293T cells that were transfected with control or LRS siRNA.

FIG. 2e shows cell size distributions of cells transfected with control, LRS, IRS, VRS, or MRS siRNA.

FIG. 2f shows cell size distributions (FSC of G1 cells) from FIG. 2e.

FIG. 2g shows the effects of LRS down regulation on LC3 cleavage.

FIG. 2h shows results after co-transfection of EGFP-LC3 with the indicated siRNAs.

FIG. 2i shows quantitative analysis of EGFP-LC3 puncta from FIG. 2f.

FIG. 3a shows purified GST-LRS that were incubated with protein extracts from 293T cells transfected with HA-tagged RagA, RagB, RagC, RagD, Rheb1, GβL, Raptor, or mTOR.

FIG. 3b shows 293T cells that were transfected with the indicated cDNAs in expression vectors.

FIG. 3c shows, after co-transfection of HA-tagged RagD with myc-tagged LRS, IRS, MRS, or EPRS, cell lysates were immunoprecipitated with anti-HA antibodies.

FIG. 3d shows (D)293T cells that were transfected with the indicated cDNAs in expression vectors.

FIG. 3e shows 293T cells that were transfected with control or myc-RagD/HA-RagB.

FIG. 3f shows each of the functional domains of RagD GTPase was expressed as GST fusion protein.

FIG. 3g shows after co-transfection of FLAG tagged LRS with HA-tagged RagB, and myc-tagged WT or mutated RagD, cell lysates were immunoprecipitated with anti-myc antibody.

FIG. 3h shows each of the C-terminal fragments of LRS was expressed as GST fusion protein.

FIG. 3i shows after co-transfection of HA-tagged RagD with myc-tagged WT or mutated LRS, cell lysates were immunoprecipitated with anti-HA antibody.

FIG. 4a shows amino acid-stimulated interaction of LRS with RagD and Raptor.

FIG. 4b shows 293T cells transfected with the indicated cDNAs in expression vectors.

FIG. 4c shows 293T cells transfected with the indicated cDNAs in expression vectors.

FIG. 4d shows 293T cells transfected with control or LRS siRNAs.

FIG. 5a shows primary sequence alignment of N-terminal region of several species leucyl-tRNA synthetases.

FIG. 5b shows leucylations by LRS WT and mutants (F50A/Y52A, F50A, and Y52A) were carried out.

FIG. 5c shows 293T cells transfected with LRS WT or F50A/Y52A mutant.

FIG. 5d shows co-transfection of HA-RagD/myc-RagB with myc-tagged WT or mutated LRS.

FIG. 5e shows 293T cells transfected with cDNAs in expression vectors.

FIGS. 6a and 6b show effects of expressing the indicated proteins on the phosphorylation of S6K in response to starvation and stimulation with amino acids.

FIG. 6c shows purified GST or GST-LRS protein incubated with HA-RagD transfected cell lysates in the presence of GDPβS or GTPγS.

FIG. 6d shows purified GST or GST-LRS protein incubated with myc-tagged RagD WT, S77L (GDP), or Q121L (GTP) transfected cell lysates.

FIG. 6e shows cell lysates immunoprecipitated with anti-myc antibody.

FIG. 6f shows 293T cells transfected with the indicated cDNAs in expression vectors.

FIG. 6g shows 293T cells transfected with the indicated cDNAs in expression vectors.

FIG. 7a shows amounts of Histagged LRS (759-1176 a.a) fragment incubated with 0.15 μM RagD.

FIG. 7b shows his-tagged LRS fragments (0.3 μM) incubated with RagD.

FIG. 7c shows sequence alignment of putative GAP motif of LRS with several species ADP-ribosylation factor-GAPs (ARF-GAPs).

FIG. 7d shows the effects of LRS WT and mutants on GTP hydrolysis of RagD.

FIG. 7e shows schematic representation for the role of LRS in amino acid signaling to mTORC1.

FIGS. 8a and 8b show 293T cells transfected with EGFP-LRS and an EGFP control expression vector.

FIG. 8c includes a quantitative analysis showing leucine-dependent lysosomal localization of LRS.

FIG. 9a shows the effect of leucine analogues on leucine-stimulated S6K phosphorylation.

FIG. 9b shows HeLa cells starved for 1 hour of leucine and preincubated with either 0.8 or 8 mM leucinol or leucine amide.

FIG. 9c shows 293T cells transfected with control or LRS siRNAs.

FIG. 9d shows HeLa cells transfected with control or LRS siRNAs.

FIG. 10a shows the effect of tRNA on in vitro LRS-RagD binding.

FIG. 10b shows the primary sequence alignment of several species leucyl-tRNA synthetases.

FIG. 10c shows leucylation and ATP-PPi exchange activities by LRS K716A/K719A mutant.

FIG. 10d shows the effect of K716A/K719A mutant on RagD binding.

FIG. 10e shows 293T cells transfected with cDNAs.

FIG. 11a shows 293T cells treated with leucine.

FIG. 11b shows quantitation of p-S6K band in FIG. 11a.

FIG. 11c shows kinetic parameters for leucylation and ATP-PPi exchange activity of WT LRS.

FIG. 13a shows ELISA results that RagD protein binds to LRS-(1-1176).

FIG. 13b shows the comparison result of binding affinity for control (GST), RagD and RagD+LRS-(759-1176) on a 96 well plate coated with LRS-(1-1176).

DETAILED DESCRIPTION OF THE ILLUSTRATED EMBODIMENTS

Figure 1A:
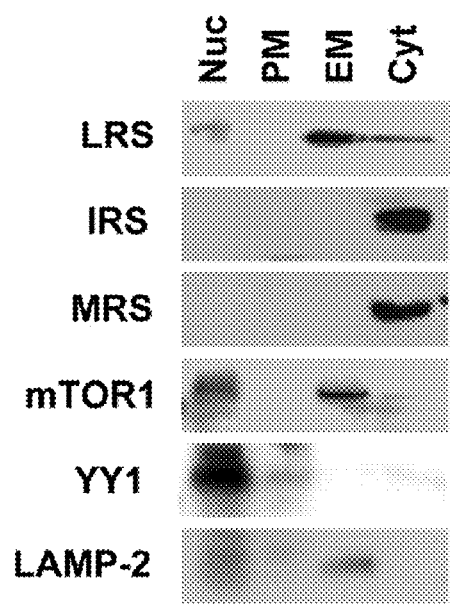
FIGS. 1a-1g include experimental results showing Leucyl-tRNA synthetase (LRS) is an mTOR-associated protein.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOTY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY. In addition, the following definitions are provided to assist the reader in the practice of the invention.

An "expression", as used herein, refers to formation of protein or nucleic acid in cells.

A "host cell," as used herein, refers to a prokaryotic or eukaryotic cell that contains heterologous DNA that has been introduced into the cell by any means, e.g., electroporation, calcium phosphate precipitation, microinjection, transformation, viral infection, and/or the like.

The term "polypeptide" is used interchangeably herein with the terms "polypeptides" and "protein(s)", and refers to a polymer of amino acid residues, e.g., as typically found in proteins in nature.

The term "LRS polypeptide," refers to a polypeptide known as leucyl tRNA synthetase. The LRS polypeptide may be a polypeptide having an amino acid sequence of SEQ ID NO: 1 (GenBank Accession No: NP 064502.9). The inventive LRS includes functional equivalents thereof.

The term "functional equivalents" refers to polypeptide comprising the amino acid sequence having at least 70% amino acid sequence homology (i.e., identity), preferably at least 80%, and more preferably at least 90%, for example, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100% amino acid sequence homology, that exhibit substantially identical physiological activity to the polypeptide of SEQ ID NO: 1. The "substantially identical physiological activity" means binding to RagD and functioning as a GTPase-activating protein (GAP) for Rag GTPase to activate mTORC1. The functional equivalents may include, for example peptides produced by as a result of addition, substitution or deletion of some amino acid(s) of SEQ ID NO:1. Substitutions of the amino acids are preferably conservative substitutions. Examples of conservative substitutions of naturally occurring amino acids are as follows: aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn) and sulfur-containing amino acids (Cys, Met). Furthermore, the functional equivalents also include variants with deletion of some of the amino acid sequence of the LRS of the present invention. Deletions or substitutions of the amino acids are preferably located at regions that are not directly involved in the physiological activity of the inventive polypeptide. Deletions of the amino acids are preferably located at regions that are not directly involved in the physiological activity of the LRS. In addition, the functional equivalents also include variants with addition of several amino acids in both terminal ends of the amino acid sequence of the LRS or in the sequence. Moreover, the inventive functional equivalents also include polypeptide derivatives which have modification of some of the chemical structure of the inventive polypeptide while maintaining the fundamental backbone and physiological activity of the inventive polypeptide. Examples of this modification include structural modifications for changing the stability, storage, volatility or solubility of the inventive polypeptide.

Sequence identity or homology is defined herein as the percentage of amino acid residues in the candidate sequence that are identical with amino acid sequence of LRS (SEQ ID NO: 1), after aligning the sequences and introducing gaps, if necessary, to achieve the maximum percent sequence identity, and not considering any conservative substitutions (as described above) as part of the sequence identity. None of N-terminal, C-terminal, or internal extensions, deletions, or insertions into the amino acid sequence of LRS shall be construed as affecting sequence identity or homology. Thus, sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences or along a predetermined portion of one or both sequences). The programs provide a default opening penalty and a default gap penalty, and a scoring matrix such as PAM 250 (a standard scoring matrix; see Dayhoff et al., in Atlas of Protein Sequence and Structure, vol. 5, supp. 3 (1978)) can be used in conjunction with the computer program. For example, the percent identity can be calculated as the follow. The total number of identical matches multiplied by 100 and then divided by the sum of the length of the longer sequence within the matched span and the number of gaps introduced into the longer sequences in order to align the two sequences.

The polypeptide according to the present invention can be prepared by separating from nature materials or genetic engineering methods. For example, a DNA molecule encoding the LRS or its functional equivalents (ex: In case of LRS, SEQ ID NO: 2 (Genbank Accession No. NM_020117.9), and in case of RagD, SEQ ID NO: 3 (Genbank Accession No. NM_021244.4)) is constructed according to any conventional method. The DNA molecule may synthesize by performing PCR using suitable primers. Alternatively, the DNA molecule may also be synthesized by a standard method known in the art, for example using an automatic DNA synthesizer (commercially available from Biosearch or Applied Biosystems). The constructed DNA molecule is inserted into a vector comprising at least one expression control sequence (ex: promoter, enhancer) that is operatively linked to the DNA sequence so as to control the expression of the DNA molecule, and host cells are transformed with the resulting recombinant expression vector. The transformed cells are cultured in a medium and condition suitable to express the DNA sequence, and a substantially pure polypeptide encoded by the DNA sequence is collected from the culture medium. The collection of the pure polypeptide may be performed using a method known in the art, for example, chromatography. In this regard, the term "substantially pure polypeptide" means the inventive polypeptide that does not substantially contain any other proteins derived from host cells. For the genetic engineering method for synthesizing the inventive polypeptide, the reader may refer to the following literatures: Maniatis et al., *Molecular Cloning: A Laboratory Manual*, Cold Spring Harbor Laboratory 1982; Sambrook et al., *Molecular Cloning; A Laboratory Manual*, Cold Spring Harbor Press, N.Y., Second (1998) and Third (2000) Editions; *Gene Expression Technology, Method in Enzymology, Genetics and Molecular Biology, Method in Enzymology*, Guthrie & Fink (eds.), Academic Press, San Diego, Calif. 1991; and Hitzeman et al., *J. Biol. Chem.*, 255, 12073-12080 1990.

Alternatively, the inventive polypeptide can be chemically synthesized easily according to any technique known in the art (Creighton, Proteins: Structures and Molecular Principles, W.H. Freeman and Co., NY, 1983). As a typical technique, they are not limited to, butinclude liquid or solid phase synthesis, fragment condensation, F-MOC or T-BOC chemistry (Chemical Approaches to the Synthesis of Peptides and Proteins, Williams et al., Eds., CRC Press, Boca Raton Fla., 1997; A Practical Approach, Atherton & Sheppard, Eds., IRL Press, Oxford, England, 1989).

The terms "nucleic acid," "DNA sequence" or "polynucleotide" refer to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides.

The term "the nucleotide encoding LRS or functional equivalents thereof" may have a nucleic acid encoding a polypeptide having the amino acid sequence of SEQ ID NO: 1 or a polypeptide having the amino acid sequence homology of at least 70% to the polypeptide. The nucleic acid includes DNA, cDNA or RNA. The polynucleotide may have a nucleotide sequence encoding the amino acid sequence of SEQ ID NO: 1 or an amino acid sequence homology of at least 70% to SEQ ID NO: 1. Preferably, the polynucleotide comprises the nucleotide sequence of SEQ ID NO. 2. The nucleic acid can be isolated from a natural source or be prepared by a genetic engineering method known in the art.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved traits (such as higher binding affinity for a target molecule) is an approach that is well known in pharmaceutical chemistry.

The term "homologous" when referring to proteins and/or protein sequences indicates that they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence.

As used herein, "contacting" has its normal meaning and refers to combining two or more agents (e.g., two polypeptides) or combining agents and cells (e.g., a protein and a cell). Contacting can occur in vitro, e.g., combining two or more agents or combining a test agent and a cell or a cell lysate in a test tube or other container. Contacting can also occur in a cell or in situ, e.g., contacting two polypeptides in a cell by coexpression in the cell of recombinant polynucleotides encoding the two polypeptides, or in a cell lysate.

The term "agent" or "test agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

More specifically, test agents that can be identified with methods of the present invention include polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, structural analogs or combinations thereof. Some test agents are synthetic molecules, and others natural molecules. Test agents are obtained from a wide variety of sources including libraries of synthetic or natural compounds. Combinatorial libraries can be produced for many types of compound that can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Libraries of natural compounds in the form of bacterial, fungal, plant and animal extracts can be obtained from commercial sources or collected in the field. Known pharmacological agents can be subject to directed or random chemical modifications, such as acylation, alkylation, esterification, amidification to produce structural analogs.

The test agents can be naturally occurring proteins or their fragments. Such test agents can be obtained from a natural source, e.g., a cell or tissue lysate. Libraries of polypeptide agents can also be prepared, e.g., from a cDNA library commercially available or generated with routine methods. The test agents can also be peptides, e.g., peptides of from about 5 to about 30 amino acids, with from about 5 to about 20 amino acids being preferred and from about 7 to about 15 being particularly preferred. The peptides can be digests of naturally occurring proteins, random peptides, or "biased" random peptides.

The test agents can also be "nucleic acids". Nucleic acid test agents can be naturally occurring nucleic acids, random nucleic acids, or "biased" random nucleic acids. For example, digests of prokaryotic or eukaryotic genomes can be similarly used as described above for proteins.

In some preferred methods, the test agents are small molecules (e.g., molecules with a molecular weight of not more than about 1,000). Preferably, high throughput assays are adapted and used to screen for such small molecules. A number of assays are available for such screening, e.g., as described in Schultz (1998) Bioorg Med Chem Lett 8:2409-2414; The Weller (1997) Mol Divers. 3:61-70; Fernandes (1998) Curr Opin Chem Biol 2:597-603; and Sittampalam (1997) Curr Opin Chem Biol 1:384-91.

The library of the inventive method of screening test agent may be prepared based on the structural research of LRS or a fragment or analog thereof. These structural research makes it possible to identify test agent which may bind to LRS.

The three-dimensional structures of the LRS can be studied in a number of ways, e.g., crystal structure and molecular modeling. Methods of studying protein structures using x-ray crystallography are well known in the literature. See, Physical Bio-chemistry, Van Holde, K. E. (Prentice-Hall, New Jersey 1971), pp. 221-239, and Physical Chemistry with Applications to the Life Sciences, D. Eisenberg & D. C. Crothers (Benjamin Cummings, Menlo Park 1979). Computer modeling of structures of LRS provides another means for designing test agents for screening LRS. Methods of molecular modeling have been described in the literature, e.g., U.S. Pat. No. 5,612,894 entitled "System and method for molecular modeling utilizing a sensitivity factor", and U.S. Pat. No. 5,583,973 entitled"Molecular modeling method and system". In addition, protein structures can also be determined by neutron diffraction and nuclear magnetic resonance (NMR). See, e.g., Physical Chemistry, 4th Ed. Moore, W. J. (Prentice-Hall, New Jersey 1972), and NMR of Proteins and Nucleic Acids, K. Wuthrich (Wiley-Interrscience, New York 1986).

Hereinafter, the present invention will be described in detail. The present invention provides a method for screening agent for preventing or treating of mTORC1-mediated disease comprising the steps of:

(a) contacting LRS (Leucyl tRNA synthetase), RagD, and a test agent with or without the test agent;

(b) comparing the binding affinity between LRS and RagD with the test agent, to the binding affinity between LRS and RagD without the test agent; and (c) measuring a change in the binding affinity between LRS and RagD.

In the present invention, the Rag protein belongs to the Rag subfamily of Ras small GTPase, and there are four kinds of Rag proteins, namely, RagA, RagB, RagC, RagD. Among them, RagA and RagB are orthologs of Gtrlp GTPase of yeast, and RagC and RagD are orthologs of Gtr2p GTPase of yeast. RagD binds to RagA or RagB to form a dimer and mediates activation of the mTORC1 pathway by amino acids. (Trends in Biochemiccal Sciences, 33: 565-568, 2008). Preferably, Rag may be RagD.

It is known that mTOR (mammalian target of rapamycin) is related to cancer, rejection of transplants, autoimmune diseases, diabetes, obesity, cardiovascular diseases, disorders in nerve system, aging, and the like (Drug Discovery Today, 12; 112-124, 2007). Accordingly, mTOR mediated diseases of the present invention may be cancer, autoimmune diseases, diabetes, obesity, and cardiovascular diseases.

More particularly, the cancers comprise, but are not limited to, malignant melanoma, leukaemia, colon cancer, lung cancer, liver cancer, stomach cancer, esophagus cancer, pancreatic cancer, gall bladder cancer, kidney cancer, bladder cancer, prostate cancer, testicular cancer, cervical cancer, endometrial carcinoma, choriocarcinoma, ovarian cancer, breast cancer, thyroid cancer, brain tumors, head or neck cancer, skin cancer, lymphoma, B-cell neoplasms such as precursor B-cell neoplasm, T-cell and NK-cell neoplasms such as precursor T-cell neoplasm and Hodgkin lymphoma (Hodgkin disease) such as Classical Hodgkin lymphoma.

Various biochemical and molecular biology techniques or assays well known in the art can be employed to practice the present invention. Such techniques are described in, e.g., Sambrook et al., Molecular Cloning: A Laboratory Manual, Cold Spring Harbor Press, N.Y., Second (1989) and Third (2000) Editions; and Ausubel et al., Current Protocols in Molecular Biology, John Wiley & Sons, Inc., New York (1987-1999).

Preferably, the test agent is first assayed for its ability to modulate a biological activity of LRS (the first assay step). Particularly, in the first step, modulating agents that modulate a biological activity of an the polypeptide may be identified by assaying a biological activity of isolated LRS, in the presence of a test agent. More preferably, the present invention may comprise:

(a) contacting test agents with LRS; and (b) measuring the activity of LRS, and selecting a testing agent that changes the activity of LRS.

More preferably, the present invention may comprise:

(a) contacting LRS (Leucyl tRNA synthetase), RagD, and a test agent with or without the test agent;

(b) measuring a binding affinity between LRS and RagD with or without the test agent;

(c) comparing the binding affinity between LRS and RagD with the test agent to the binding affinity between LRS and RagD without the test agent; and (d) measuring a change between the binding affinity between LRS and RagD with the test agent to the binding affinity between LRS and RagD without the test agent.

Modulation of different biological activities of LRS can be assayed in the first step. For example, a test agent can be assayed for activity to modulate expression levels of LRS, e.g., transcription or translation. The test agent can also be assayed for activities in modulating cellular level or stability of LRS, e.g., post-translational modification or proteolysis.

Test agents that increase a biological activity of LRS are identified by the first assay, the test agents are then subject to further testing to determine whether the test agents have ability to bind Rag, more exactly RagD (or RagD GTPase), in the presence of LRS (the second testing step).

In both the first step and the second step, an intact LRS and subunits or their fragments, analogs, or functional derivatives can be used. The fragments that can be employed in these assays usually retain one or more of the biological activities of LRS. Fusion proteins containing such fragments or analogs can also be used for the screening of test agents. Functional derivatives of LRS usually have amino acid deletions and/or insertions and/or substitutions, while maintaining one or more of the bioactivities and therefore, can also be used in practicing the screening methods of the present invention.

A variety of the well-known techniques can be used to identify test agents that modulate LRS. Preferably, the test agents are screened with a cell-based assay system. For example, in a typical cell-based assay (i.e., the second screening step), the activity of a reporter gene (i.e., enzyme activity) is measured in the presence of a test agent, and then compared to the activity of the reporter gene in the absence of test agent. The reporter gene can encode any detectable polypeptide (response or reporter polypeptide) known in the art, e.g., detectable by fluorescence or phosphorescence or by virtue of its possessing an enzymatic activity. The detectable response polypeptide can be, e.g., luciferase, alpha-glucuronidase, alpha-galactosidase, chloramphenicol acetyl transferase, green fluorescent protein, enhanced green fluorescent protein, and the human secreted alkaline phosphatase.

In the cell-based assays, the test agent (e.g., a peptide or a polypeptide) can also be expressed from a different vector that is also expressed in the host cell. In some methods, a library of test agents is encoded by a library of such vectors (e.g., a cDNA library; see the Example below). Such libraries can be generated using methods well known in the art (see, e.g., Sambrook et al. and Ausubel et al., supra) or obtained from a variety of commercial sources.

In addition to cell based assays described above, it can also be screened with non-cell based methods. These methods include, e.g., mobility shift DNA-binding assays, methylation and uracil interference assays, DNase and hydroxy radical footprinting analysis, fluorescence polarization, and UV crosslinking or chemical cross-linkers. For a general overview, see, e.g., Ausubel et al., supra (chapter 12, DNA-Protein Interactions). One technique for isolating co-associating proteins, including nucleic acid and DNA/RNA binding proteins, includes the use of UV crosslinking or chemical cross-linkers, including e.g., cleavable cross-linkers dithiobis (succinimidylpropionate) and 3,3'-dithiobis (sulfosuccinimidyl-propionate); see, e.g., McLaughlin, Am. J. Hum. Genet., 59:561-569, 1996; Tang, Biochemistry, 35:8216-8225, 1996; Lingner, Proc. Natl. Acad. Sci. U.S.A., 93:10712, 1996; and Chodosh, Mol. Cell. Biol., 6:4723-4733, 1986.

First Assay Step: Screening Test Agents that Modulate LRS (Optional)

A number of assay systems can be employed to screen test agents for modulators of LRS. As noted above, the screening can utilize an in vitro assay system or a cell-based assay system. In this screening step, test agents can be screened for binding to LRS, altering cellular level of LRS, or modulating other biological activities of LRS.

1) Screening of Test Agents that Bind LRS

In the first screening step, binding of a test agent to LRS is determined. For example, it can be assayed by a number of methods including e.g., labeled in vitro protein-protein binding assays, electrophoretic mobility shift assays, immunoassays for protein binding, functional assays (phosphorylation assays, etc.), and the like. See, e.g., U.S. Pat. Nos. 4,366,241; 4,376,110; 4,517,288; and 4,837,168; and also Bevan et al., Trends in Biotechnology 13:115-122, 1995; Ecker et al., Bio/Technology 13:351-360, 1995; and Hodgson, Bio/Technology 10:973-980, 1992. The test agent can be identified by detecting a direct binding to LRS, e.g., co-immunoprecipitation with LRS by an antibody directed to LRS. The test agent can also be identified by detecting a signal that indicates that the agent binds to LRS, e.g., fluorescence quenching.

Competition assays provide a suitable format for identifying test agents that specifically bind to LRS. In such formats, test agents are screened in competition with a compound already known to bind to LRS. The known binding compound can be a synthetic compound. It can also be an antibody, which specifically recognizes LRS polypeptide, e.g., a monoclonal antibody directed against LRS. If the test agent inhibits binding of the compound known to bind LRS, then the test agent also binds LRS.

Numerous types of competitive binding assays are known, for example: solid phase direct or indirect radioimmunoassay (MA), solid phase direct or indirect enzyme immunoassay (ETA), sandwich competition assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using.sup.125I label (see Morel et al., Mol. Immunol. 25(1): 7-15 (1988)); solid phase direct biotin-avidin EIA (Cheung et al., Virology 176:546-552 (1990)); and direct labeled RIA (Moldenhauer et al., Scand. J. Immunol. 32:77-82 (1990)). Typically, such an assay involves the use of a purified polypeptide bound to a solid surface or cells bearing either of these, an unlabeled test agent and a labeled reference compound. Competitive inhibition is measured by determining the amount of label bound to the solid surface or cells in the presence of the test agent. Usually the test agent is present in excess. Modulating agents identified by competition assay include agents binding to the same epitope as the reference compound and agents binding to an adjacent epitope sufficiently proximal to the epitope bound by the reference compound for steric hindrance to occur. Usually, when a competing agent is present in excess, it will inhibit specific binding of a reference compound to a common target polypeptide by at least 50 to 75%.

The screening assays can be either in insoluble or soluble formats. One example of the insoluble assays is to immobilize LRS or its fragments onto a solid phase matrix. The solid phase matrix is then put in contact with test agents, for an interval sufficient to allow the test agents to bind. Following washing away any unbound material from the solid phase matrix, the presence of the agent bound to the solid phase allows identification of the agent. The methods can further include the step of eluting the bound agent from the solid phase matrix, thereby isolating the agent. Alternatively, other than immobilizing LRS, the test agents are bound to the solid matrix and the LRS is then added.

Soluble assays include some of the combinatory libraries screening methods described above. Under the soluble assay formats, neither the test agents nor LRS are bound to a solid support. Binding of LRS or fragment thereof to a test agent can be determined by, e.g., changes in fluorescence of either LRS or the test agents, or both. Fluorescence may be intrinsic or conferred by labeling either component with a fluorophor.

In some binding assays, either LRS, the test agent, or a third molecule (e.g., an antibody against LRS) can be provided as labeled entities, i.e., covalently attached or linked to a detectable label or group, or cross-linkable group, to facilitate identification, detection and quantification of the polypeptide in a given situation. These detectable groups can comprise a detectable polypeptide group, e.g., an assayable enzyme or antibody epitope. Alternatively, the detectable group can be selected from a variety of other detectable groups or labels, such as radiolabels (e.g., 125I, 32P, 35S) or a chemiluminescent or fluorescent group. Similarly, the detectable group can be a substrate, cofactor, inhibitor or affinity ligand.

2) Screening Test Agents Modulating Other Activities of LRS

Binding of a test agent to LRS provides an indication that the agent can be a modulator of LRS. It also suggests that the agent may modulate biological activity of Rag, preferably RagD or RagD GTPase. Thus, a test agent that binds to LRS can be further tested for ability to modulate activity of a laminin receptor.

Alternatively, a test agent that binds to LRS can be further examined to determine its activity on LRS. The existence, nature, and extent of such activity can be tested by an activity assay. Such an activity assay can confirm that the test agent binding to LRS indeed has a modulatory activity on LRS. More often, such activity assays can be used independently to identify test agents that modulate activities of LRS (i.e., without first assaying their ability to bind to LRS). In general, such methods involve adding a test agent to a sample containing LRS in the presence or absence of other molecules or reagents which are necessary to test a biological activity of LRS and determining an alteration in the biological activity of LRS. In addition to assays for screening agents that modulate enzymatic or other biological activities of LRS, the activity assays also encompass in vitro screening and in vivo screening for alterations in expression or cellular level of LRS.

Second Test Step: Screening Agents that Modulate mTORC1 Activity by Rag

Once a modulating agent has been identified to bind to KRS and/or to modulate a biological activity (including cellular level) of LRS, it can be tested for ability to modulate mTORC1 activity by Rag or further be tested whether there is ability of preventing or treating mTORC1 mediated diseases such as cancer. Modulation of the modulating agent is typically tested in the presence of LRS. When a cell-based screening system is employed, LRS can be expressed from an expression vector that has been introduced into a host cell. Alternatively, LRS can be supplied endogenously by the host cell in the screening system.

Meanwhile, the present invention provides a method of reducing cell size as compared to a control group, comprising inhibiting expression of intracellular LRS.

mTORC1 is known to regulate cell size (Fingar D C, Salama S, Tsou C, Harlow E, Blenis J. Mammalian cell size is controlled by mTOR and its downstream targets S6K1 and 4EBP1/eIF4E. Genes Dev. 16 (2002), pp. 1472-1487). According to the relationship between LRS and mTORC1, which is identified by the present inventors, the present inventors confirmed that suppression of LRS expression results reduction of cell size. As a result, it is confirmed that the cells suppressed LRS showed smaller size as compared to those of the control group (FIG. 2e upper and FIG. 2f).

The suppression of intracellular LRS is regulated with various well known methods in the art. The suppression of intracellular LRS may be controlled, but not limited thereto, through transforming the cells with the vectors comprising polynucleotides encoding antisense RNA or interference RNA of LRS operably linked to a promoter.

The "promoter" means a DNA sequence regulating the expression of nucleic acid sequence operably linked to the promoter in a specific host cell, and the term "operably linked" means that one nucleic acid fragment is linked to other nucleic acid fragment so that the function or expression thereof is affected by the other nucleic acid fragment. Additionally, the promoter may further comprise an operator sequence for controlling transcription, a sequence encoding a suitable mRNA ribosome-binding site, and sequences controlling the termination transcription and translation. The promoter may be constitutive promoter which constitutively induces the expression of a target gene, or inducible promoter which induces the expression of a target gene at a specific site and a specific time.

The cells of the present invention may be cells having signal transduction system mediated by mTORC1.

The present invention also provides a method for screening agents for preventing or treating mTORC1-mediated diseases comprising the steps of:

(a) contacting LRS (Leucyl tRNA synthetase) and RagD with a test agent and without the test agent;

(b) comparing the binding affinity between LRS and RagD with the test agent to the binding affinity between LRS and RagD without the test agent; and (c) identifying the test agent's effect on the binding affinity between LRS and RagD.

More preferably, the present invention may comprise:

(a) contacting LRS (Leucyl tRNA synthetase) and RagD with a test agent and without the test agent;

(b) measuring a binding affinity between LRS and RagD with and without the test agent;

(c) comparing the binding affinity between LRS and RagD with the test agent to the binding affinity between LRS and RagD without the test agent; and (d) identifying the test agents that inhibit the binding affinity between LRS and RagD.

As mentioned above, the screening method can be performed using various methods known in the art, including labeled invitro protein-protein binding assays (invitro fulldown assays), EMSA (electrophoretic mobility shift assays), immuno assays for protein binding, functional assays (phosphorylation assays, etc.), yeast-2hybrid assay, assays of non-immune immuno-precipitations, immuno-precipitation/Westernblot assays, immuno-co-localization assays, and the like.

For example, yeast two hybrid assays can be performed using yeast expressing LRS and RagD, or parts or homologues of these proteins, fused with the DNA-binding domain of bacteria repressor LexA, or yeast GAL4 and the transactivation domain of yeast GAL4 protein, respectively (KIM, M. J. et al., Nat. Gent., 34:330-336, 2003). The binding between LRS and RagD reconstitutes a transactivator that induces the expression of a reporter gene under the control by a promoter having a regulatory sequence bound to the DNA-binding domain of LexA protein or GAL4.

As described above, the reporter gene may be any gene known in the art, that encodes a detectable polypeptide. For example, chloramphenicol acetyltransferase (CAT), luciferase, β-galactosidase, β-glucosidase, alkaline phosphatase, green fluorescent protein (GFP), etc. may be used. If the level of binding between LRS and RagD, or parts or homologues of these proteins is stimulated or enhanced by a test agent, the expression of the reporter gene will be increased compared to that under a normal condition. Conversely, if the level of the binding is suppressed or attenuated by a test agent, the reporter gene will not be expressed or expressed less than that under normal conditions.

Further, a reporter gene encoding a protein which enables growth of yeast (i.e., when the reporter gene is not expressed, the growth of yeast is inhibited) may be selected. For example, the reporter genes may be auxotropic genes encoding enzymes involved in a biosynthesis pathway for amino acids or nitrogenous bases (e.g., yeast genes such as ADE3, HIS3, etc. or equivalent genes from other species). If the interaction between LRS and RagD, or parts or homologues of these proteins, expressed in this system, is inhibited or attenuated by a test agent, the reporter gene will not be expressed.

Accordingly, the growth of yeast is arrested or reduced under the above conditions. This effect is caused by the expression of the reporter gene and may be observed by the naked eye or a device (e.g., a microscope).

Hereafter, the figures of the present invention will be described.

FIGS. 1a-1g show experimental results indicating that Leucyl-tRNA synthetase (LRS) is an mTOR-associated protein. FIG. 1a shows subcellular fractionation of LRS. Each fraction was subjected to immunoblotting with anti-LRS, IRS, MRS, and mTOR antibodies. YY1 and LAMP2 were used as nucleus and endomembrane markers, respectively.

In FIG. 1a: Nuc refers to nucleus; PM refers to plasma membrane; EM refers to endomembrane; Cyt refers to cytosol.

Figure 1B:
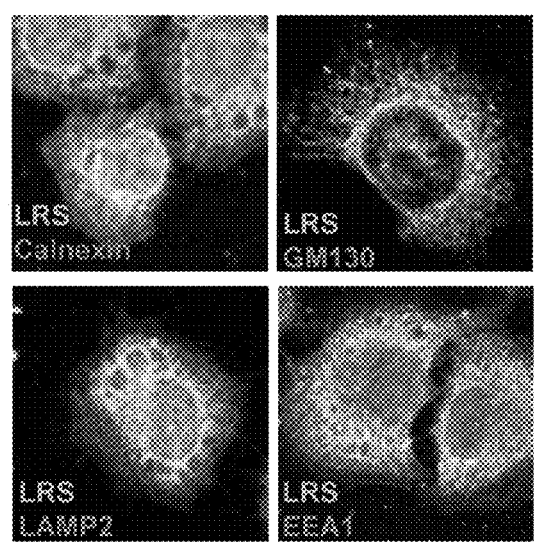

FIG. 1b shows immunofluorescence staining of LRS in HeLa cells. HeLa cells were reacted with anti-LRS, anti-calnexin (ER marker), anti-GM130 (Golgi marker), anti-LAMP2 (lysosome marker), or anti-EEA1 (endosome marker) antibodies and visualized with alexa 488-conjugated and alexa 594-conjugated secondary antibodies, respectively.

Figure 1C:
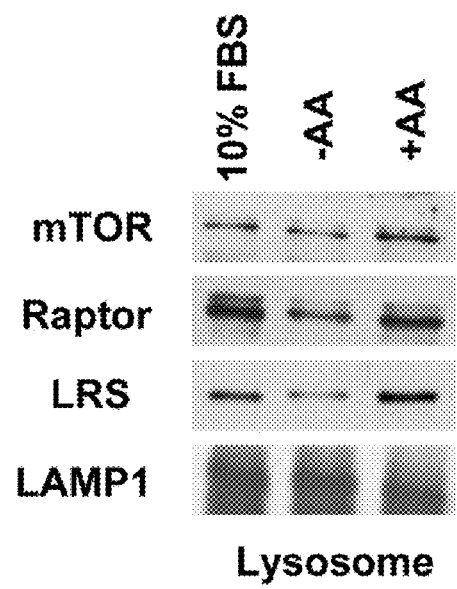

FIG. 1c shows lysosomal localization of LRS. 293T cells were starved for amino acids for 1 hour and re-stimulated with amino acids for 5 min. Cells were fractionated with lysosome isolation kit (Sigma-Aldrich). Lysosomal proteins were immunoblotted with anti-mTOR, anti-Raptor, anti-LRS, and anti-LAMP1 antibodies.

Figure 1D:
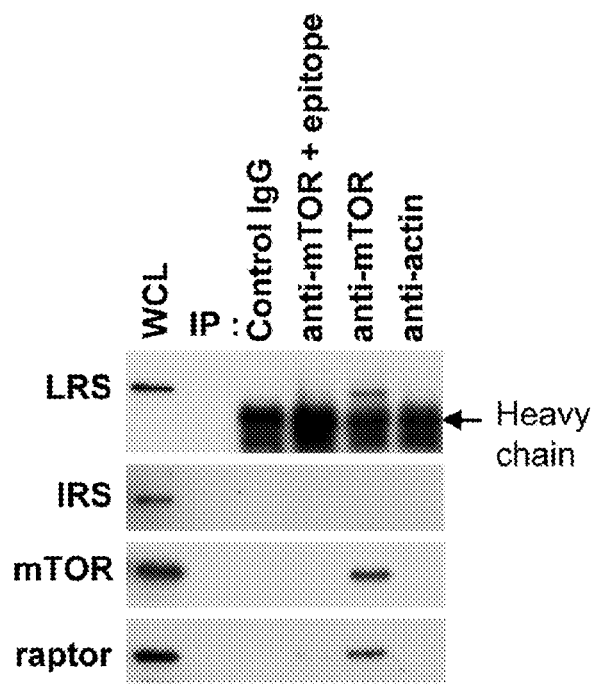

FIG. 1d shows 293T cell lysates that were immunoprecipitated with anti-mTOR antibodies and the co-precipitated LRS and Raptor were determined by immunoblotting. Goat IgG, anti-mTOR antibody plus blocking epitope peptide and anti-actin antibody were used as negative controls.

Figure 1E:
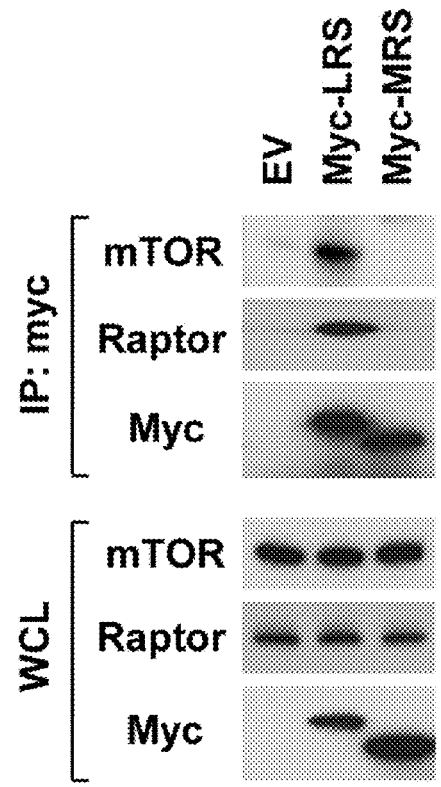

FIG. 1e shows (E) 293T cells that were transfected with control plasmid (EV), myc-tagged LRS, or MRS. Cell lysates were immunoprecipitated with anti-myc antibody and the co-precipitated mTOR and Raptor were determined by immunoblotting.

Figure 1F:
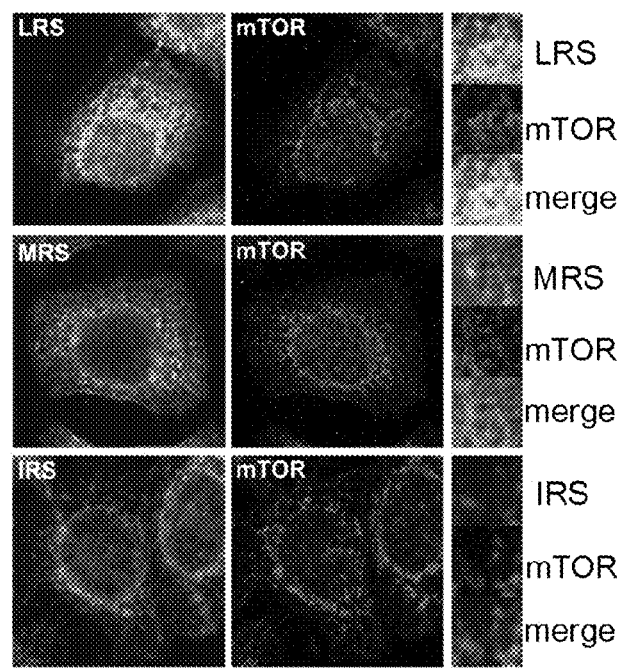

FIG. 1f shows co-localization of LRS with mTOR in HeLa cells. Cells were reacted with anti-LRS, anti-MRS, anti-IRS, and anti-mTOR antibodies and visualized with alexa 488-conjugated and alexa 594-conjugated secondary antibodies, respectively.

Figure 1G:
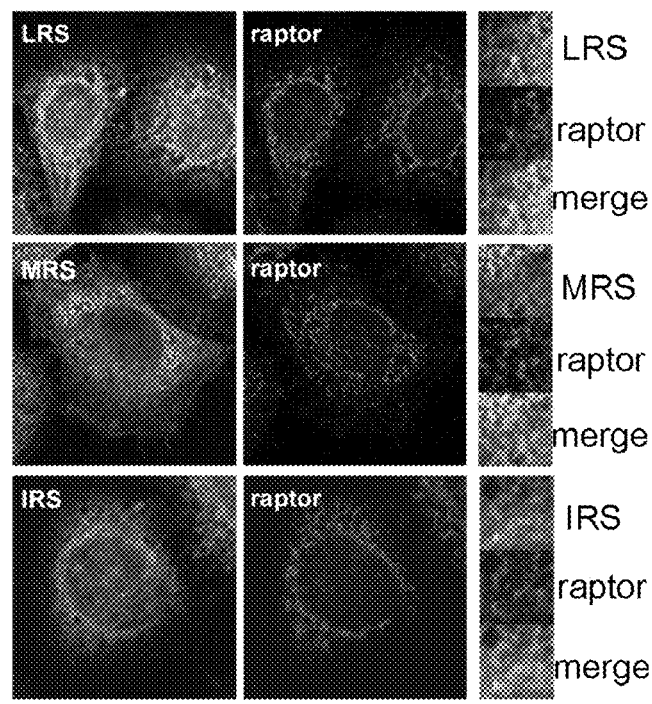

FIG. 1g shows co-localization of LRS with Raptor in HeLa cells. Cells were reacted with anti-LRS, anti-MRS, anti-IRS, and anti-Raptor antibodies and visualized with alexa 488-conjugated and alexa 594-conjugated secondary antibodies, respectively.

Figure 2A:
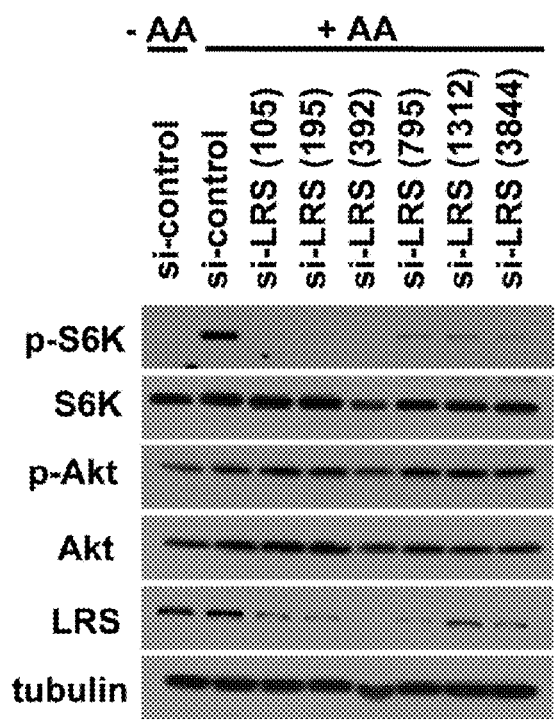
FIGS. 2a-2i include experimental results showing the effect of LRS on mTORC1 activation and lysosomal localization, cell size, and autophagy.
Figure 2B:
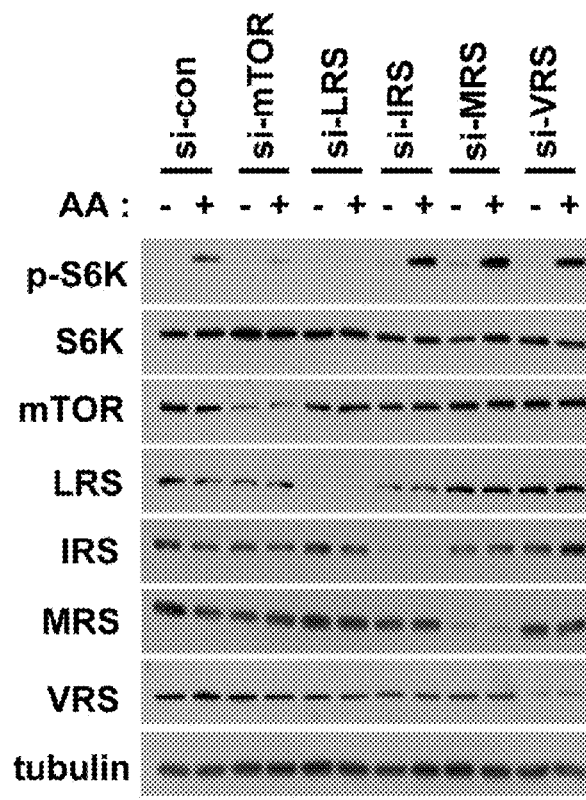
Figure 2C:
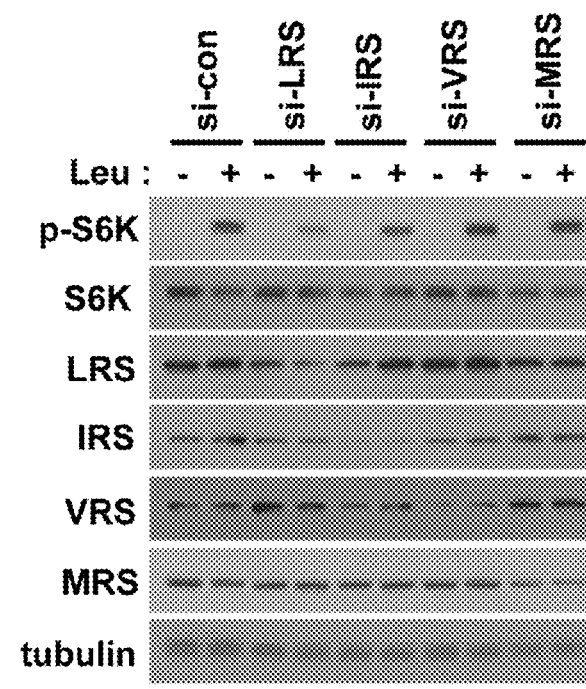
Figure 2D:
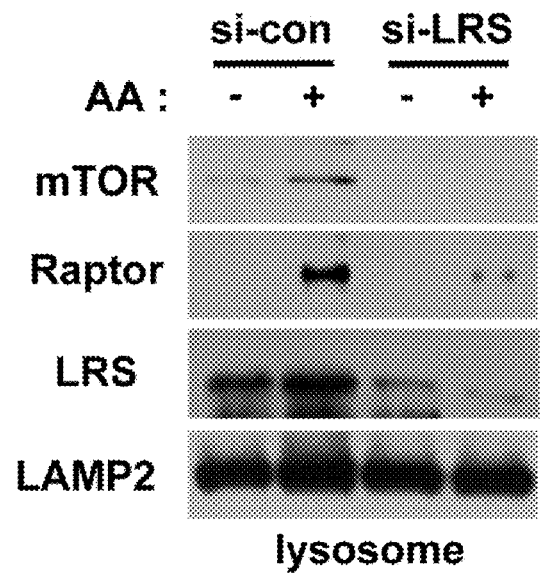
Figure 2E:
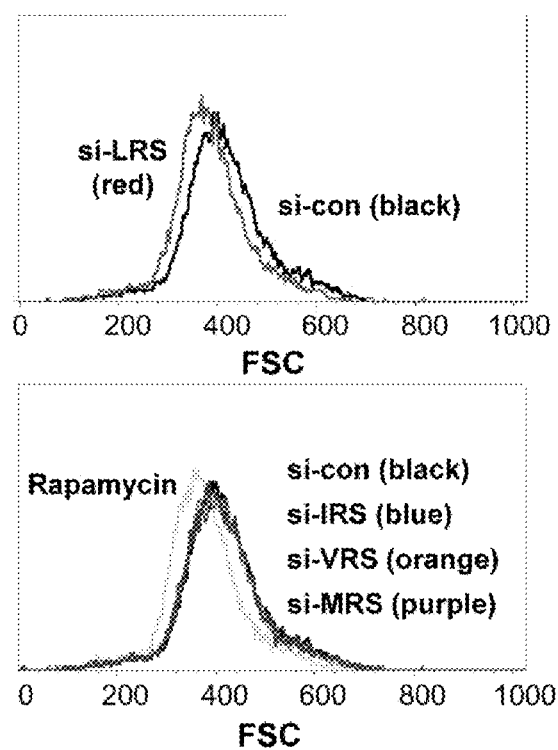
Figure 2F:
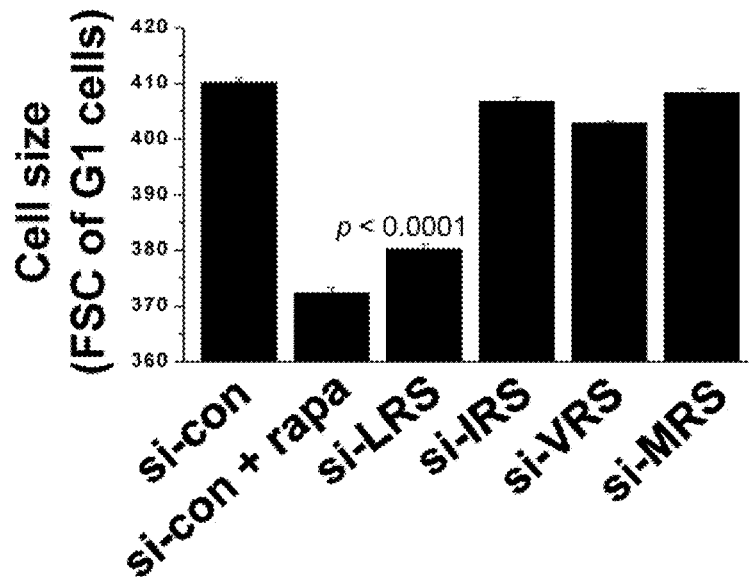

FIGS. 2a-2i show the effect of LRS on mTORC1 activation and lysosomal localization, cell size, and autophagy. FIG. 2a shows 293T cells that were transfected with 6 kinds of LRS siRNA for 48 hours, and amino acid dependent S6K phosphorylation was determined by immunoblotting.

FIG. 2b shows 293T cells that were transfected with control, mTOR, LRS, IRS, MRS, or VRS siRNA for 48 hours. Amino acid-dependent S6K phosphorylation was determined by immunoblotting.

FIG. 2c shows 293T cells that were transfected with control, LRS, IRS, MRS, or VRS siRNA for 48 hours. Leucine-dependent S6K phosphorylation was determined by immunoblotting.

FIG. 2d shows 293T cells that were transfected with control or LRS siRNA for 48 hours. The cells were starved for amino acids for 1 hour and re-stimulated with amino acids for 5 min. The cells were fractionated with lysosome isolation kit (Sigma-Aldrich). Lysosomal proteins were immunoblotted with anti-mTOR, anti-Raptor, anti-LRS, and anti-LAMP2 antibodies FIG. 2e shows cell size distributions of cells transfected with control, LRS, IRS, VRS, or MRS siRNA. FIG. 2f shows cell size distributions (FSC of G1 cells) from FIG. 2e that were quantified. (n=3 and p<0.0001).

Figure 2G:
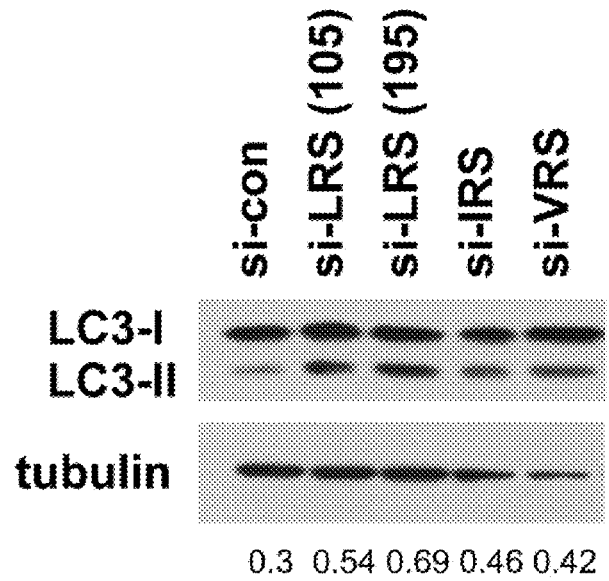

FIG. 2g shows the effects of LRS down regulation on LC3 cleavage. 293T cells were transfected with the indicated siRNAs for 48 hours and starved for leucine for 2 hours. Cell lysates were prepared and LC3-I and -II were determined by immunoblotting with anti-LC3 antibody. Autophagy induction is indicated by the ratio of LC3 II/LC3 I.

Figure 2H:
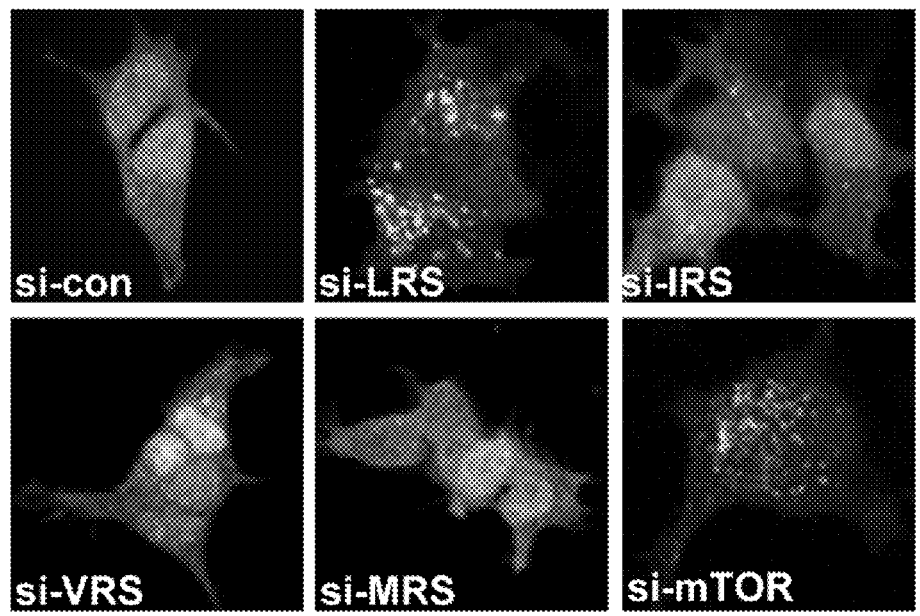

FIG. 2h shows results after co-transfection of EGFP-LC3 with the indicated siRNAs. The cells were starved for leucine and serum for 2 hours. Accumulation of EGFP-LC3 in puncta, was monitored.

Figure 2I:
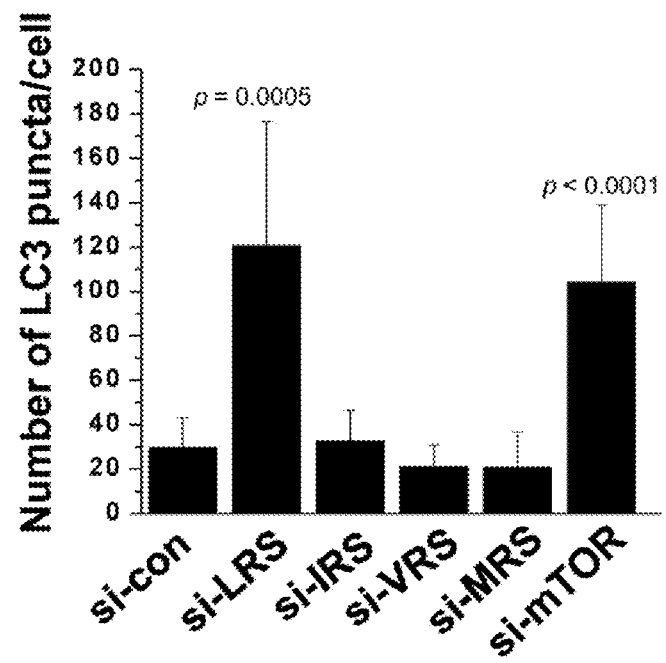

FIG. 2i shows quantitative analysis of EGFP-LC3 puncta from FIG. 2f At least eight cells were analyzed per sample. The data represents mean±S.D. LRS siRNA and mTOR siRNA-transfected cells showed statistically significant increase of LC3 puncta per cell, as compared to control siRNA-transfected cells (p=0.0005 and p<0.0001, respectively).

Figure 3A:
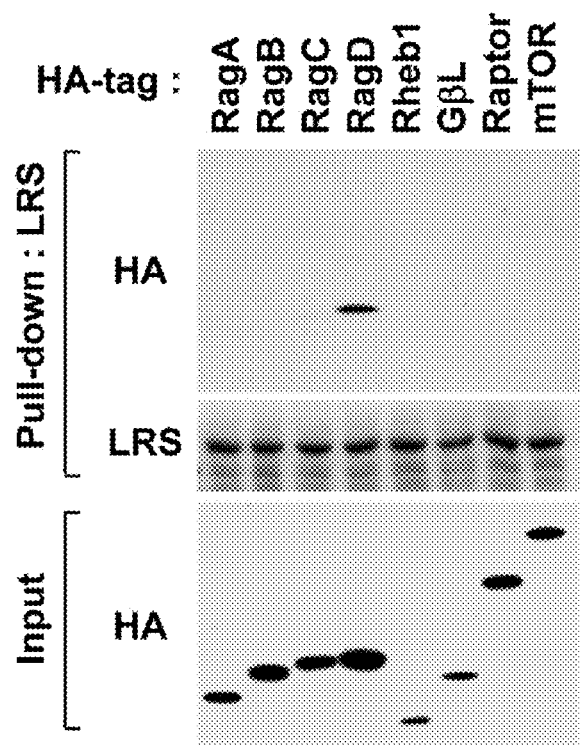
FIGS. 3a-3i include experimental results showing direct interactions of LRS with RagD GTPase.

FIGS. 3a-3i show direct interactions of LRS with RagD GTPase. FIG. 3a shows purified GST-LRS that were incubated with protein extracts from 293T cells transfected with HA-tagged RagA, RagB, RagC, RagD, Rheb1, GβL, Raptor, or mTOR. The co-precipitation of HA-tagged proteins were determined by immunoblotting with anti-HA antibodies. Inputs are the amount of 10% protein extract used.

Figure 3B:
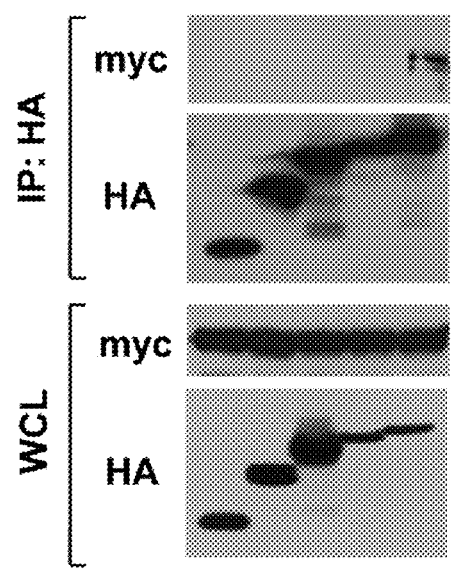

FIG. 3b shows 293T cells that were transfected with the indicated cDNAs in expression vectors. Cell lysates were prepared, and cell lysates and HA-tagged immunoprecipitates were analyzed by immunoblotting with anti-myc or anti-HA antibodies. WCL means whole cell lysate.

Figure 3C:
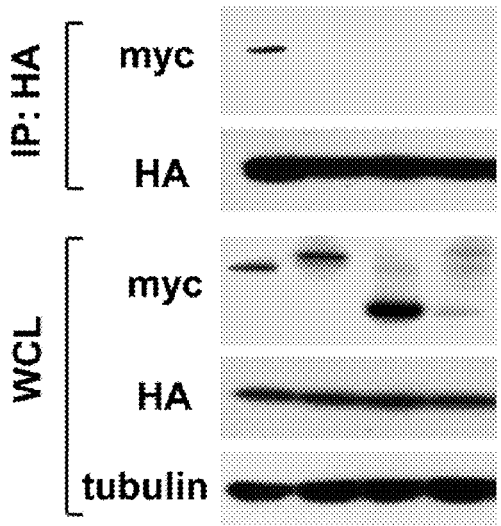

In FIG. 3c, after co-transfection of HA-tagged RagD with myc-tagged LRS, IRS, MRS, or EPRS, cell lysates were immunoprecipitated with anti-HA antibodies. The co-precipitated myc-tagged protein was determined by immunoblotting with anti-myc antibodies.

Figure 3D:
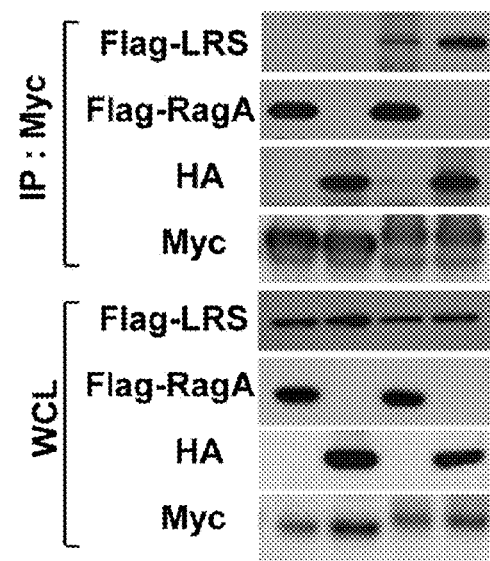

FIG. 3d shows (D)293T cells that were transfected with the indicated cDNAs in expression vectors. Cell lysates were prepared, and cell lysates and myc-tagged immunoprecipitates were analyzed by immunoblotting with anti-FLAG, anti-myc, or anti-HA antibodies.

Figure 3E:
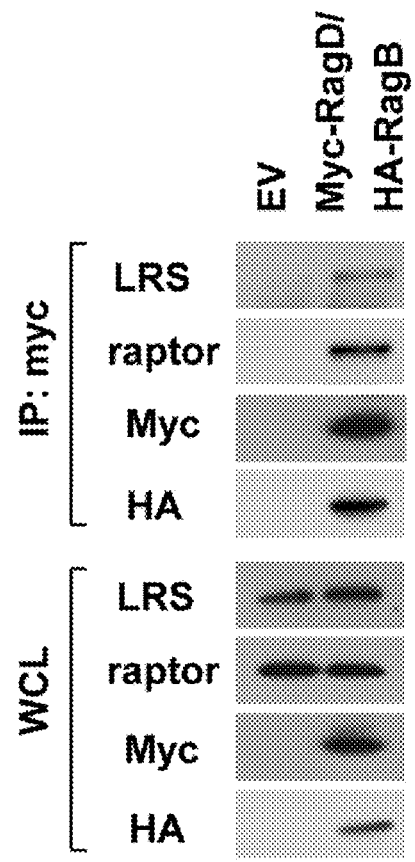

FIG. 3e shows 293T cells that were transfected with control or myc-RagD/HA-RagB. Cell lysates were immunoprecipitated with anti-myc antibody and the myc-tagged immunoprecipitates were analyzed by immunoblotting with anti-HA, anti-LRS or anti-Raptor antibodies.

Figure 3F:
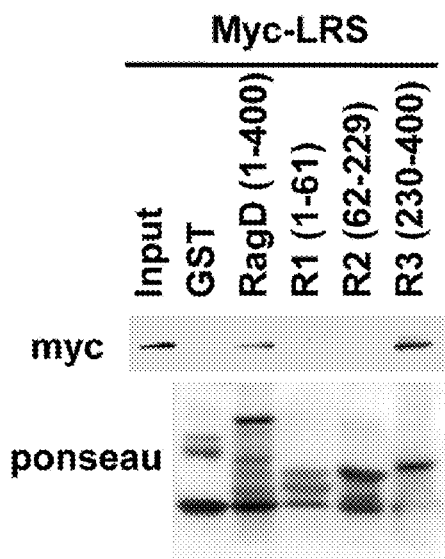

In FIG. 3f, each of the functional domains of RagD GTPase was expressed as GST fusion protein. Purified GST-RagD proteins were incubated with myc-tagged LRS, and the co-precipitation of myc-LRS was determined by immunoblotting with anti-myc antibody.

Figure 3G:
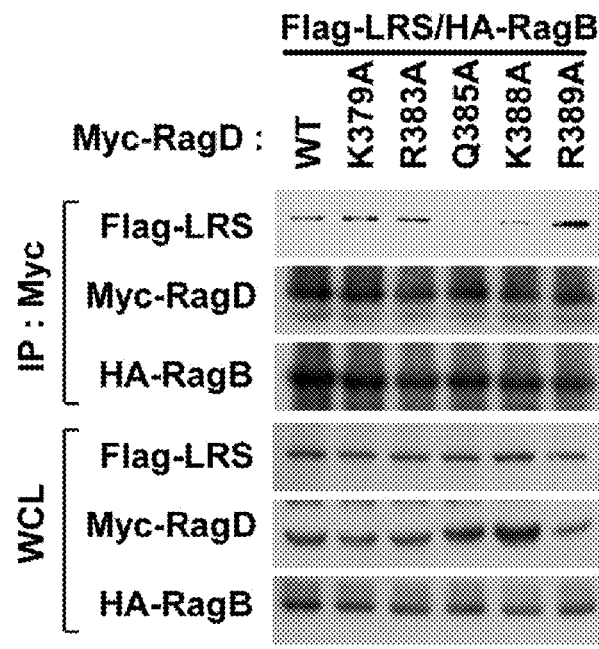

In FIG. 3g, after co-transfection of FLAG tagged LRS with HA-tagged RagB, and myc-tagged WT or mutated RagD, cell lysates were immunoprecipitated with anti-myc antibody and the co-precipitated LRS and RagB were determined by immunoblotting with anti-FLAG and anti-HA antibodies.

Figure 3H:
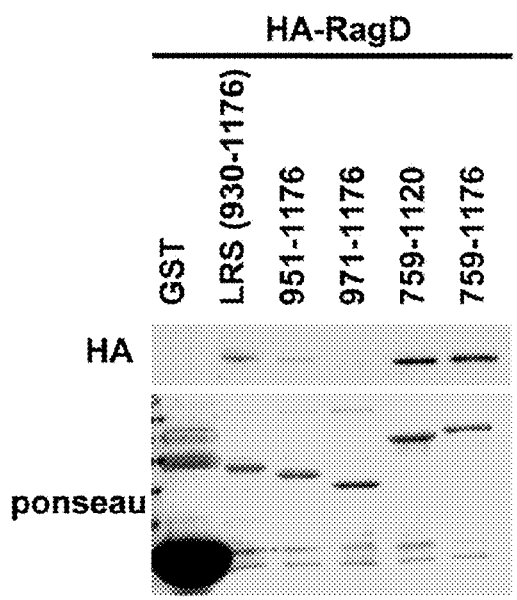

In FIG. 3h, each of the C-terminal fragments of LRS was expressed as GST fusion protein. Purified GST-LRS proteins were incubated with HARagD-transfected cell lysates, and the co-precipitation of HA-RagD was determined by immunoblotting with anti-HA antibody.

Figure 3I:
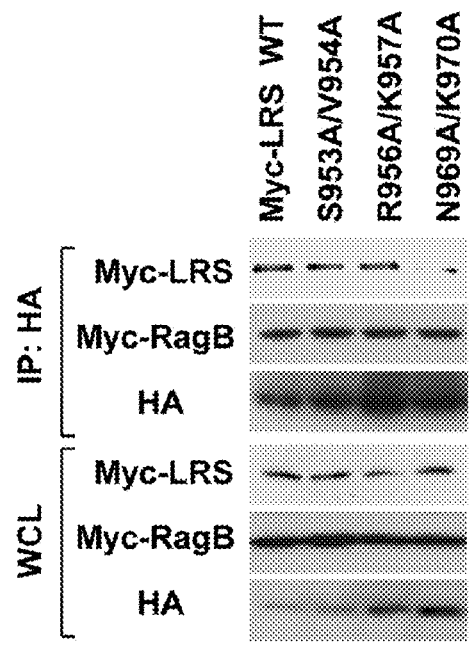

In FIG. 3i, after co-transfection of HA-tagged RagD with myc-tagged WT or mutated LRS, cell lysates were immunoprecipitated with anti-HA antibody. The coprecipitated LRS was determined by immunoblotting with anti-myc antibody.

Figure 4A:
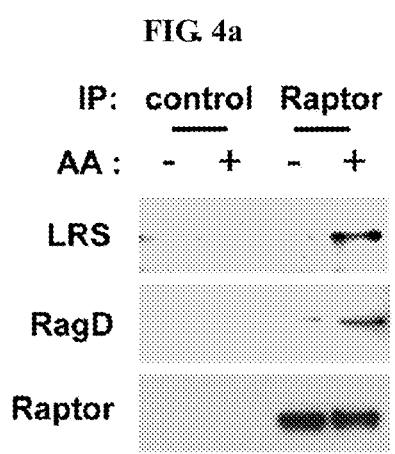
FIGS. 4a-4d include experimental results showing that LRS forms a molecular complex with RagD and Raptor in amino acid-dependent manner.

FIGS. 4a-4d show that LRS forms a molecular complex with RagD and Raptor in amino acid-dependent manner. In FIG. 4a, amino acid-stimulated interaction of LRS with RagD and Raptor is shown. 293T cells were starved for amino acids for 1 hour and re-stimulated with amino acids for 5 min. Cell lysates were immunoprecipitated with anti- Raptor antibody and the co-precipitated LRS and RagD were determined by immunoblotting with anti-LRS and anti-RagD antibody.

Figure 4B:
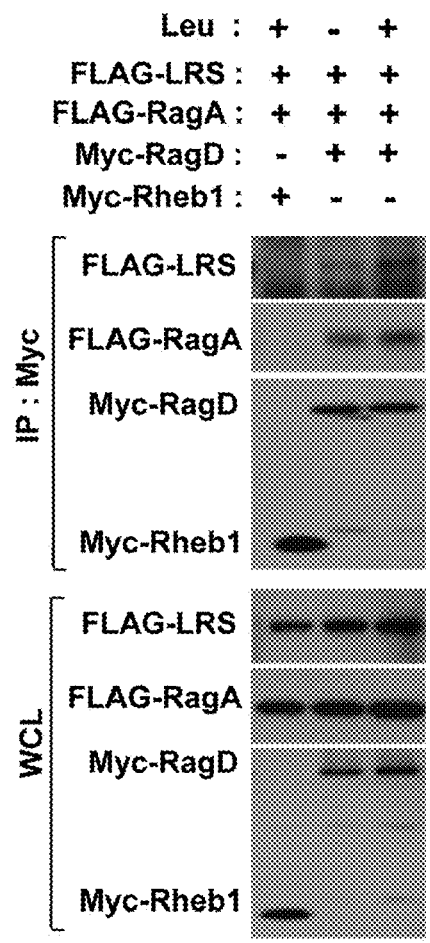

In FIG. 4b, 293T cells were transfected with the indicated cDNAs in expression vectors. Cells were starved for leucine for 1 hour and restimulated with leucine for 5 min. Cell lysates and myc-tagged immunoprecipitaes were analyzed by immunoblotting with anti-FLAG and anti-myc antibodies.

Figure 4C:
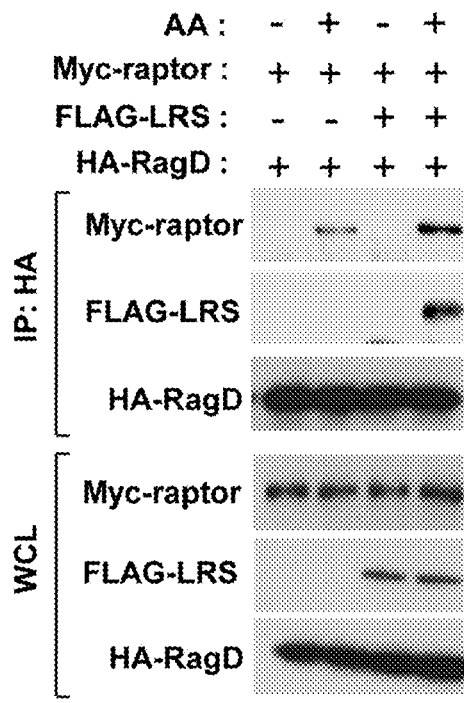

In FIG. 4c, 293T cells were transfected with the indicated cDNAs in expression vectors. Cells were starved for amino acids for 1 hour and restimulated with amino acids for 5 min. Cell lysates and HA-tagged immunoprecipitaes were analyzed by immunoblotting with anti-myc, anti-FLAG, and anti-HA antibodies.

Figure 4D:
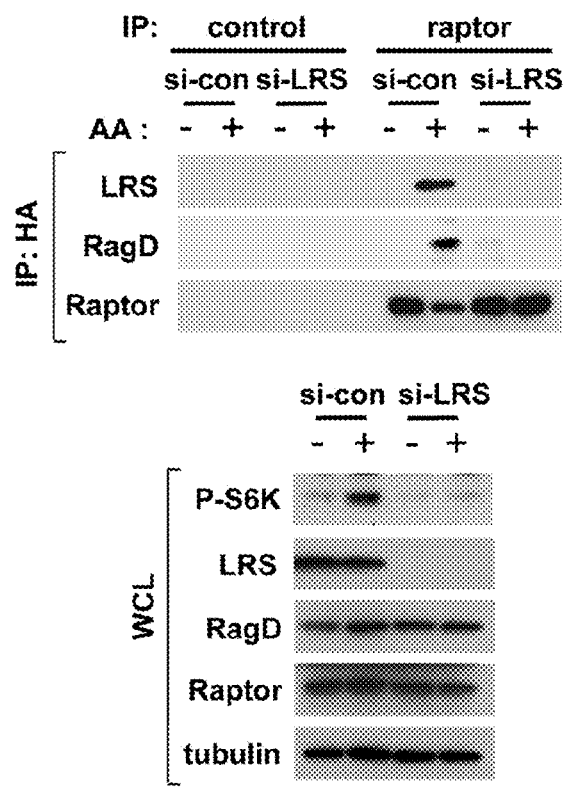

In FIG. 4d, LRS is necessary for the complex formation of RagD with Raptor. 293T cells were transfected with control or LRS siRNAs for 48 hours. Cells were starved for amino acids for 1 hour and re-stimulated with amino acids for 5 min. Cell lysates were immunoprecipitated with anti-Raptor antibody and the precipitates were analyzed by immunoblotting with anti-LRS and anti-RagD antibodies.

Figures 5A, 5B:
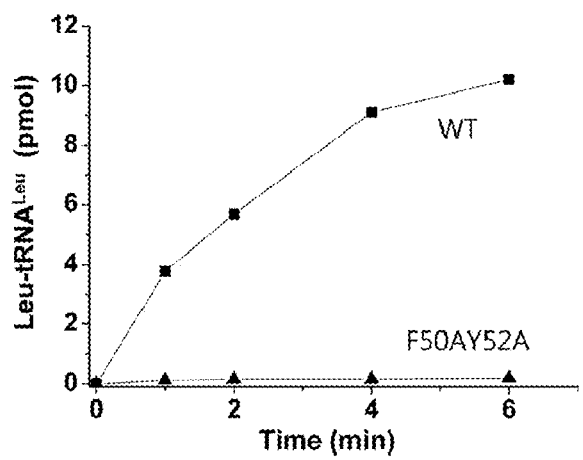
FIGS. 5a-5e include experimental results showing that LRS functions as a leucine receptor for mTORC1 signaling.

FIGS. 5a-5e show LRS functions as a leucine receptor for mTORC1 signaling. In FIG. 5a, primary sequence alignment of N-terminal region of several species leucyl-tRNA synthetases is shown. The class 1a conserved HIGH motif, which is important to ATP binding, is boxed in grey.

In FIG. 5b, leucylations by LRS WT and mutants (F50A/Y52A, F50A, and Y52A) were carried out by using 4 µM tRNALeu and 50 nM enzymes.

Figure 5C:
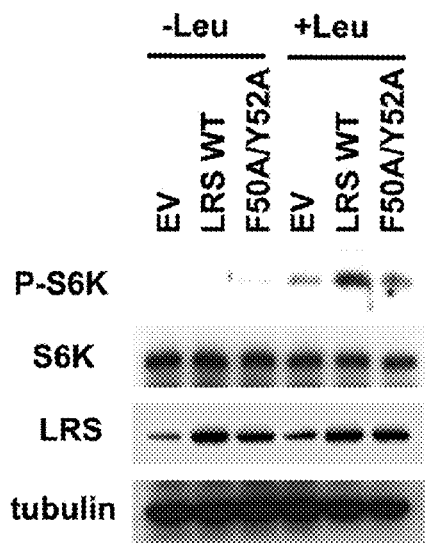

In FIG. 5c, 293T cells were transfected with LRS WT or F50A/Y52A mutant for 24 hours and then starved for amino acids for 1 hour and re-stimulated with amino acids for 5 min. Leucine-dependent S6K phosphorylation was determined by immunoblotting.

Figure 5D:
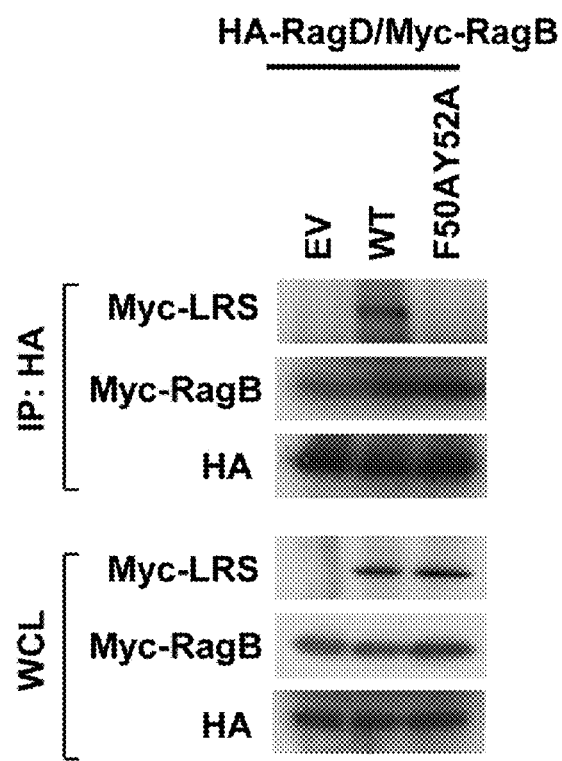

In FIG. 5d, after co-transfection of HA-RagD/myc-RagB with myc-tagged WT or mutated LRS, cell lysates were immunoprecipitated with anti-HA antibody, and the co-precipitated LRS was determined by immunoblotting with anti-myc antibody.

Figure 5E:
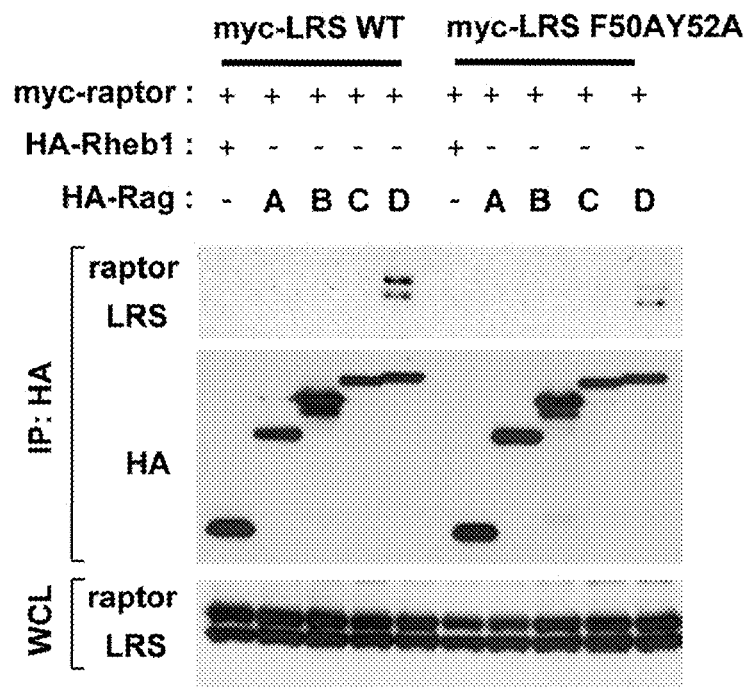

In FIG. 5e, 293T cells were transfected with the indicated cDNAs in expression vectors. Cell lysates were immunoprecipitated with anti-HA antibody, and the co-precipitated LRS and Raptor were determined by immunoblotting with anti-myc antibody.

Figure 6A:
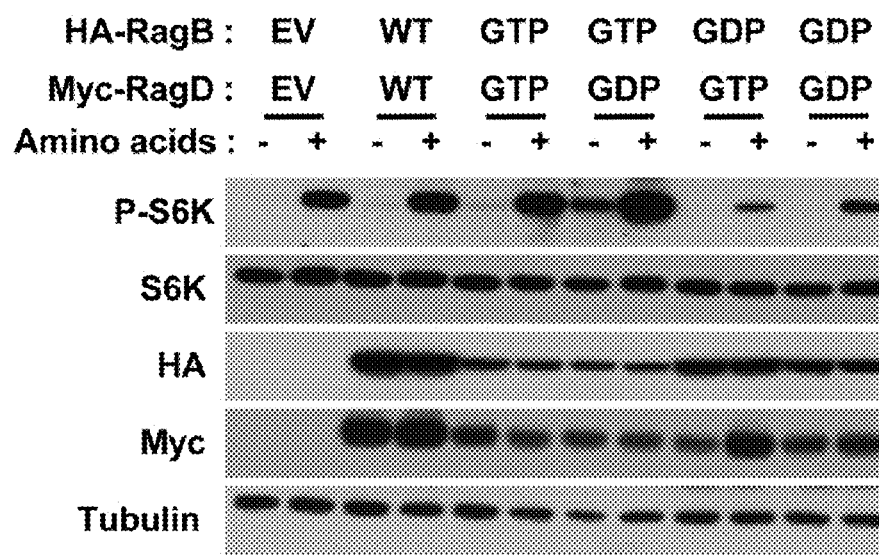
FIGS. 6a-6g show that interaction of LRS with RagD occur in a manner that depends on the nucleotide binding state of RagD.
Figure 6B:
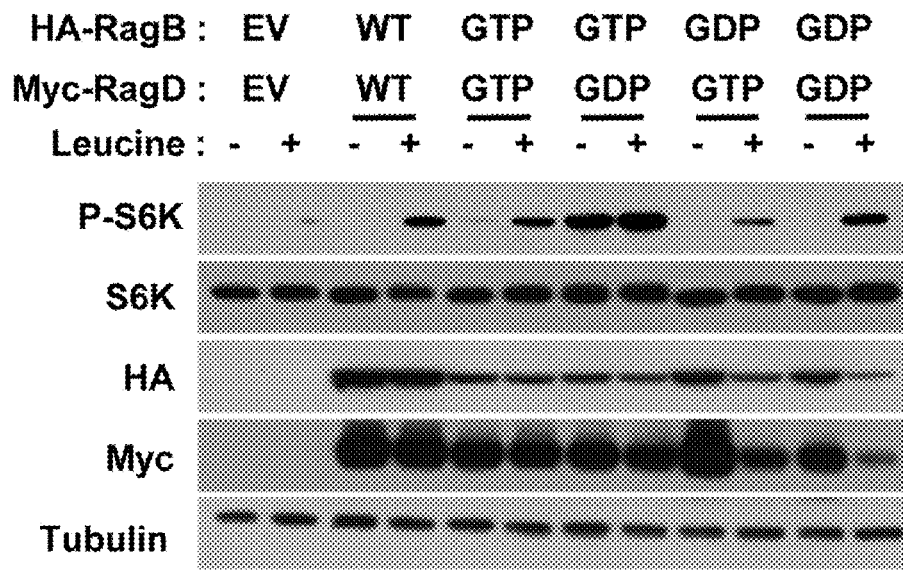

FIGS. 6a-6g show interaction of LRS with RagD in a manner that depends on the nucleotide binding state of RagD. FIGS. 6a and 6b show effects of expressing the indicated proteins on the phosphorylation of S6K in response to starvation and stimulation with amino acids (FIG. 6a) and leucine (FIG. 6b). Cell lysates were prepared from 293T cells starved for 1 hour of (FIG. 6a) amino acids or (FIG. 6b) leucine and then stimulated with amino acids or leucine for 5 min.

Figure 6C:
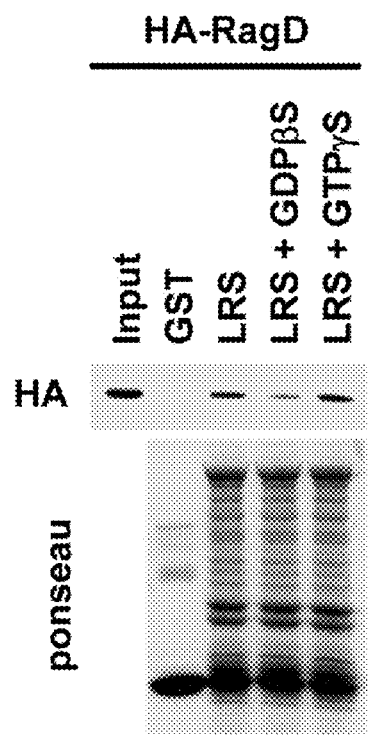

In FIG. 6c, purified GST or GST-LRS protein was incubated with HA-RagD transfected cell lysates in the presence of GDPβS or GTPγS. The co-precipitated RagD was determined by immunoblotting with anti-HA antibody.

Figure 6D:
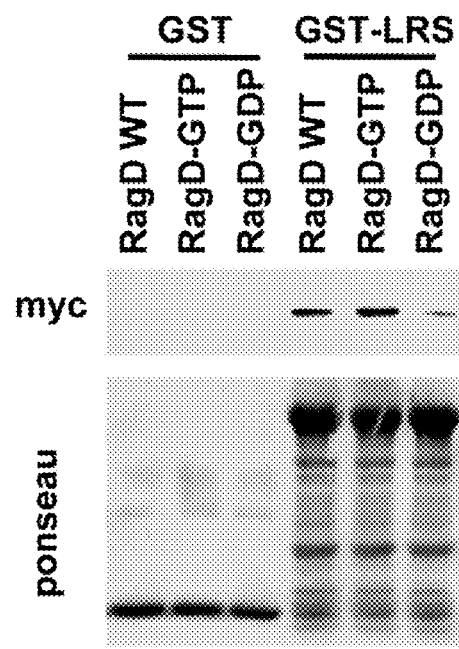

In FIG. 6d, purified GST or GST-LRS protein was incubated with myc-tagged RagD WT, S77L (GDP), or Q121L (GTP) transfected cell lysates. The coprecipitated RagD was determined by immunoblotting with anti-myc antibody.

Figure 6E:
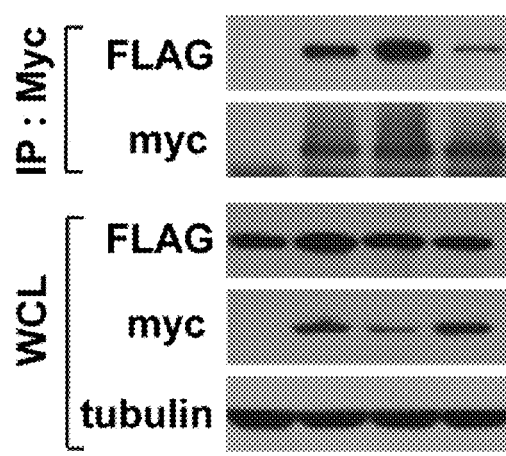

In FIG. 6e, after co-transfection of FLAG-tagged LRS with myc-tagged WT or mutated RagD, cell lysates were immunoprecipitated with anti-myc antibody and the co-precipitated LRS and RagD were determined by immunoblotting with anti-FLAG and anti-myc antibodies.

Figure 6F:
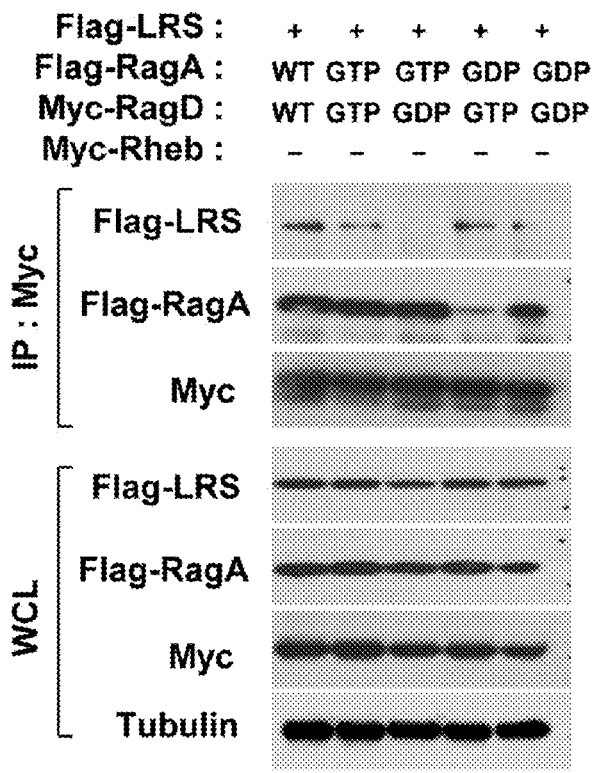

In FIG. 6f, 293T cells were transfected with the indicated cDNAs in expression vectors. Cell lysates were prepared, and cell lysates and myc-tagged immunoprecipitates were analyzed by immunoblotting with anti-FLAG or anti-myc antibody.

Figure 6G:
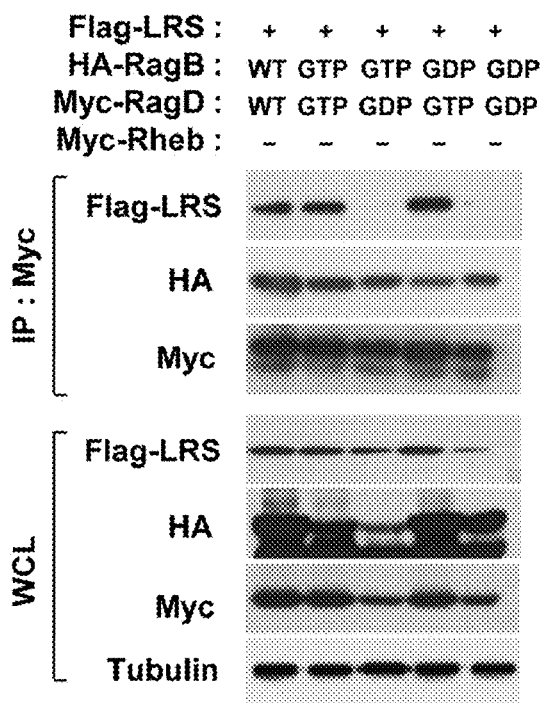

In FIG. 6g, 293T cells were transfected with the indicated cDNAs in expression vectors. Cell lysates were prepared, and cell lysates and myc-tagged immunoprecipitates were analyzed by immunoblotting with anti-FLAG, anti-HA, or anti-myc antibodies.

Figure 7A:
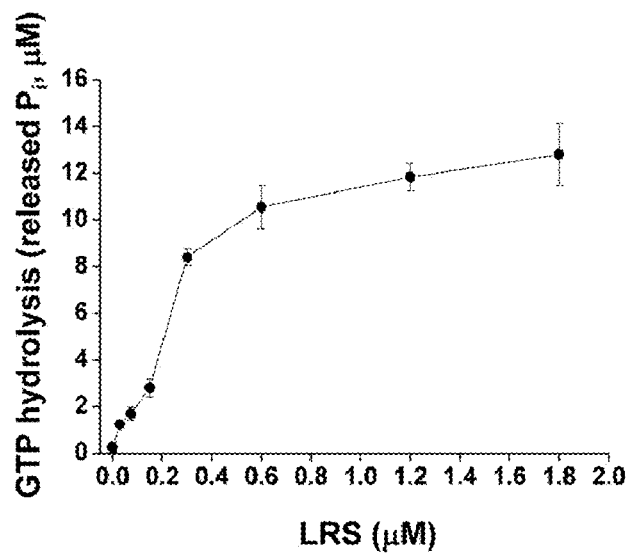
FIGS. 7a-7e include experimental results showing that LRS acts as a GTPase-activating protein for RagD.

FIGS. 7a-7e show that LRS acts as a GTPase-activating protein for RagD. In FIG. 7a, the indicated amounts of Histagged LRS (759-1176 a.a) fragment were incubated with 0.15 pM RagD for 20 min at 37° C. The error bars represent mean S.D. (n=3).

Figure 7B:
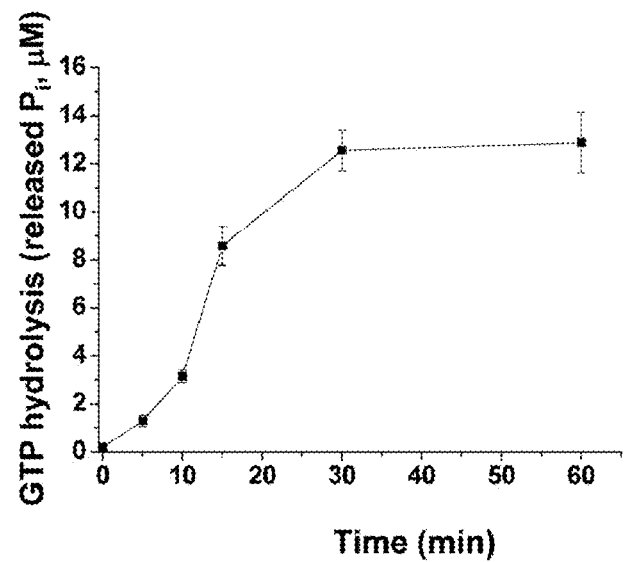

In FIG. 7b, his-tagged LRS fragments (0.3 µM) were incubated with RagD for the indicated times. The error bars represent mean S.D. (n=3).

Figures 7C, 7D:
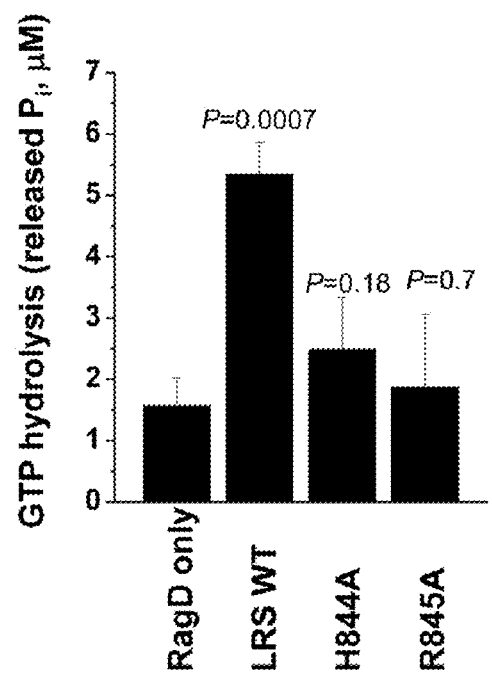

In FIG. 7c, sequence alignment of putative GAP motif of LRS with several species ADP-ribosylation factor-GAPs (ARF-GAPs) is shown. Conserved residues are black. Further, the symbols are defined as follows: h, hydrophobic; s, Gly or Ala; x, any residue. hs, *Homo sapiens*; rn, *Rattus norvegicus*; dm, *Drosophila melanogaster*; sc, *Saccharomyces cerevisiae*; ss, *Sus scrofa*.

In FIG. 7d, the effects of LRS WT and mutants on GTP hydrolysis of RagD is shown. Purified LRS WT (759-1176 a.a) fragment or mutants (H844A, R845A) fragments were incubated with RagD for 20 min at 37° C. The error bars represent mean S.D. (n=3).

Figure 7E:
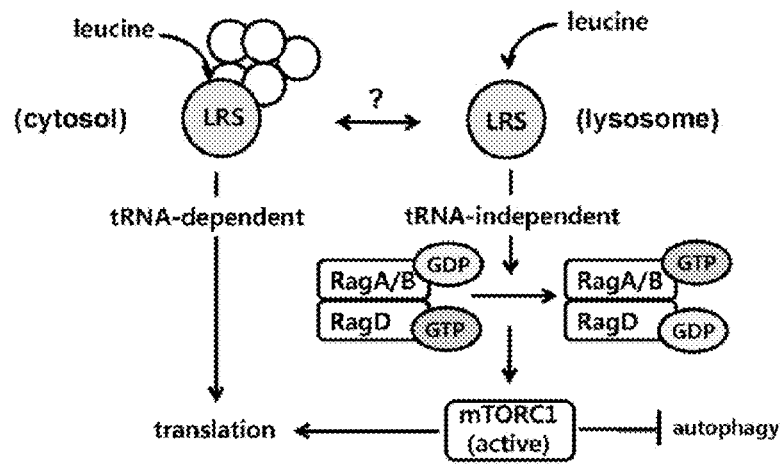

FIG. 7e shows schematic representation for the role of LRS in amino acid signaling to mTORC1.

Figure 8A:
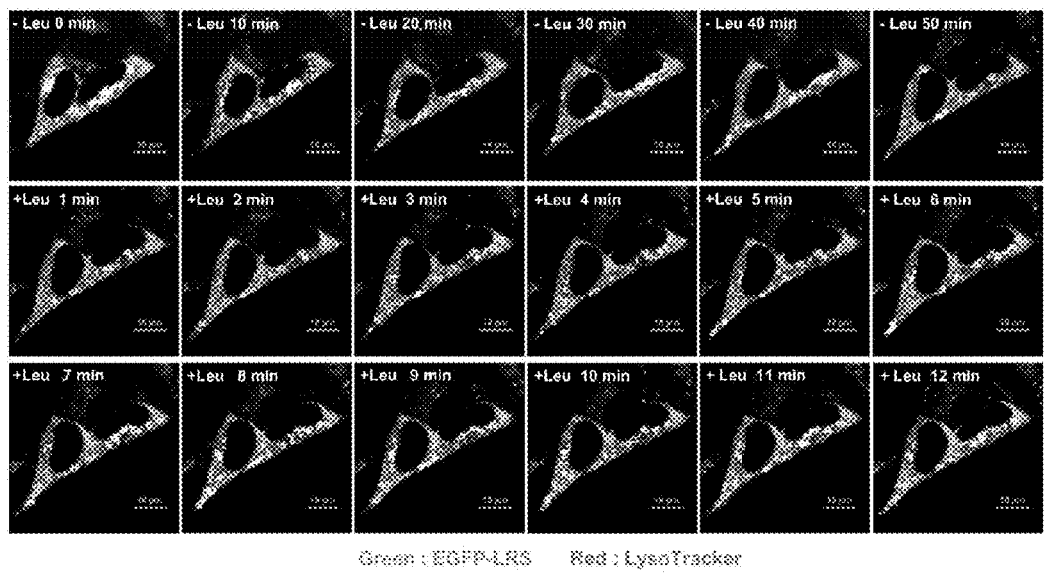
FIGS. 8a-8c show time-lapsed confocal live cell imaging of lysosomal localization of LRS.
Figure 8B:
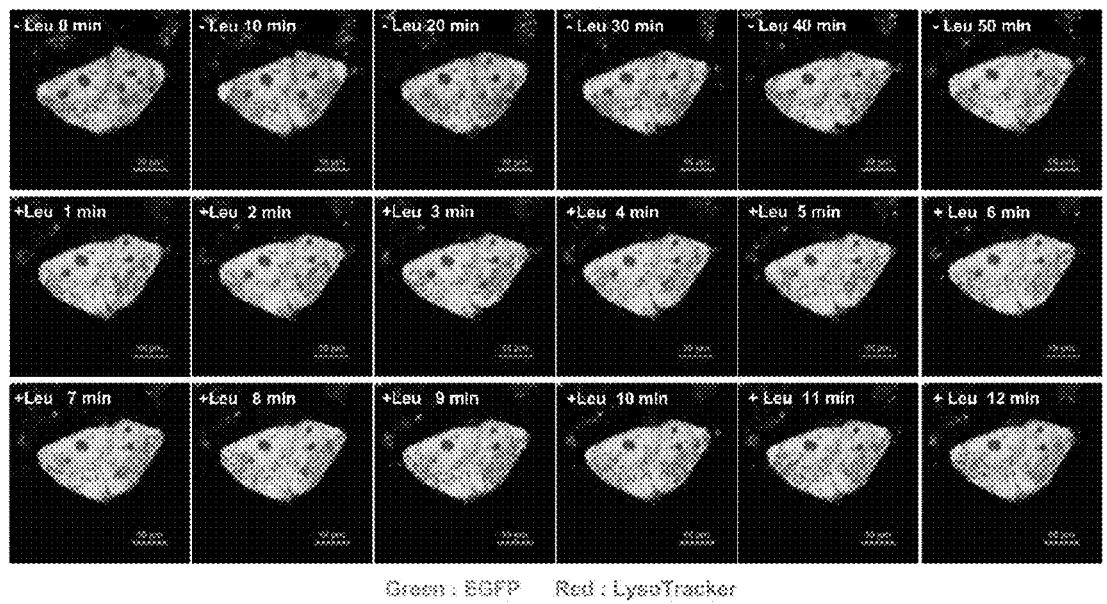
Figure 8C:
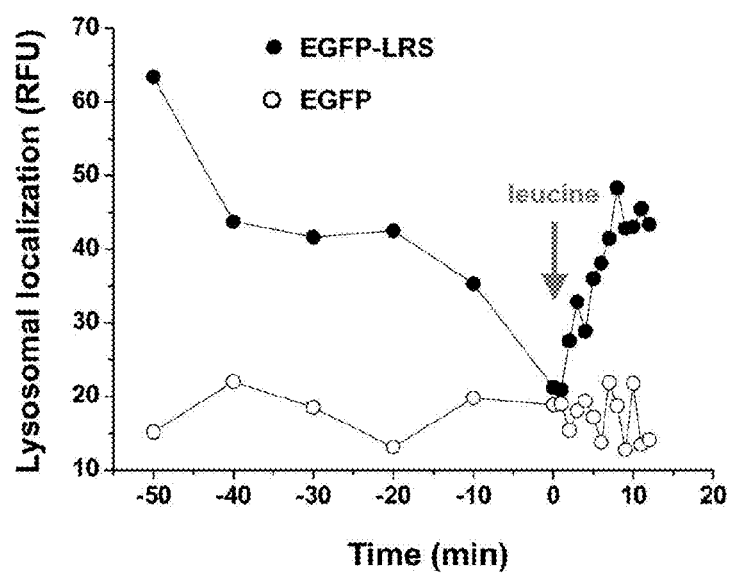

FIGS. 8a-8c show time-lapse confocal live cell imaging of lysosomal localization of LRS. FIGS. 8a and 8b shown 293T cells that were transfected with EGFP-LRS (FIG. 8a) and an EGFP control (FIG. 8b) expression vector for 36 hours and then stained with LysoTracker Red DND-99 (Molecular Probes) for 30 min. Cells were starved for leucine for 50 min and re-stimulated with 0.8 mM leucine for 12 min. During leucine starvation, cells were monitored at 10 min intervals and then monitored at 1 min intervals after re-stimulation with leucine. FIG. 8c includes a quantitative analysis showing leucine-dependent lysosomal localization of LRS.

Figure 9A:
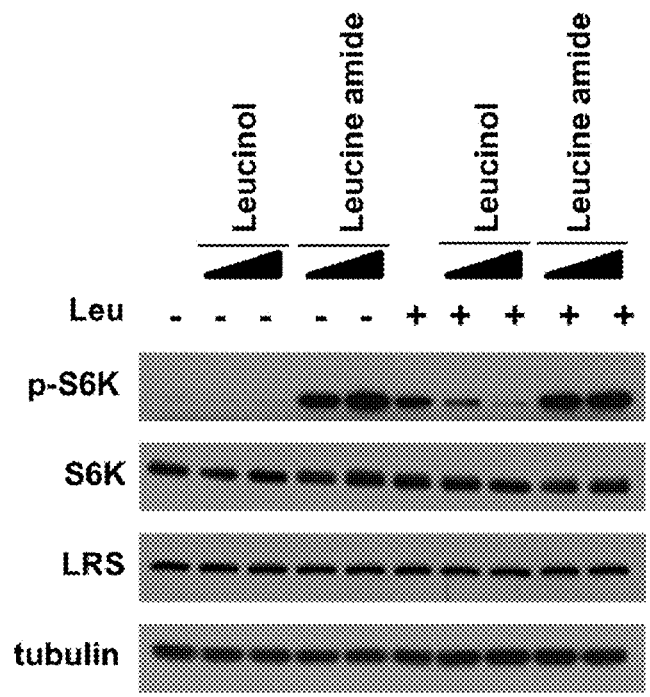
FIGS. 9a-9d include experimental results showing the effect of LRS knockdown on leucine- or leucine analogues-stimulated S6K phosphorylation.

FIGS. 9a-9d show the effect of LRS knockdown on leucine- or leucine analogues-stimulated S6K phosphorylation. In FIG. 9a, the effect of leucine analogues on leucine-stimulated S6K phosphorylation is shown. 293T cells were starved for 1 hour of leucine and preincubated with either 0.8 or 8 mM leucinol or leucine amide. After 5 min, 0.8 mM leucine was added. After 5 min incubation, cells were harvested and S6K phosphorylation was determined by immunoblotting.

Figure 9B:
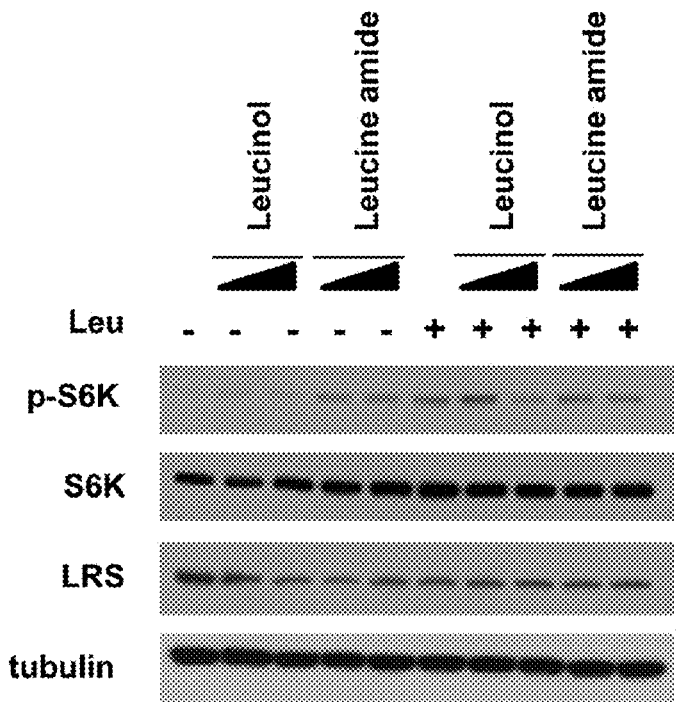

In FIG. 9b, HeLa cells were starved for 1 hour of leucine and preincubated with either 0.8 or 8 mM leucinol or leucine amide. After 5 min, 0.8 mM leucine was added. After 5 min incubation, cells were harvested and S6K phosphorylation was determined by immunoblotting.

Figure 9C:
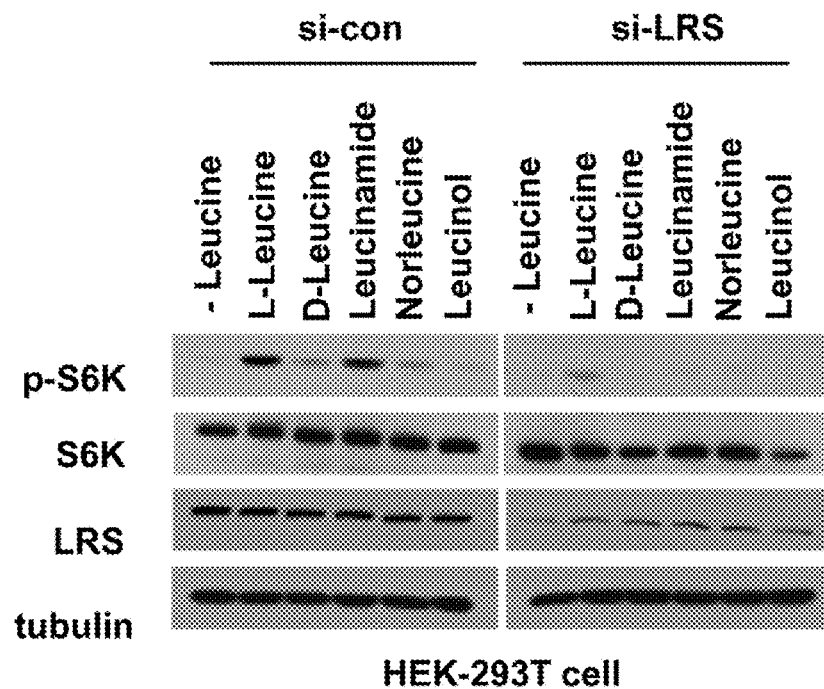

In FIG. 9c, 293T cells were transfected with control or LRS siRNAs for 48 hours and leucine- or leucine analogues-stimulated S6K phosphorylation was determined by immunoblotting. The concentration of L-leucine and leucine amide was 0.8 mM and the concentration of D-leucine, norleucine, and leucinol was 8 mM.

Figure 9D:
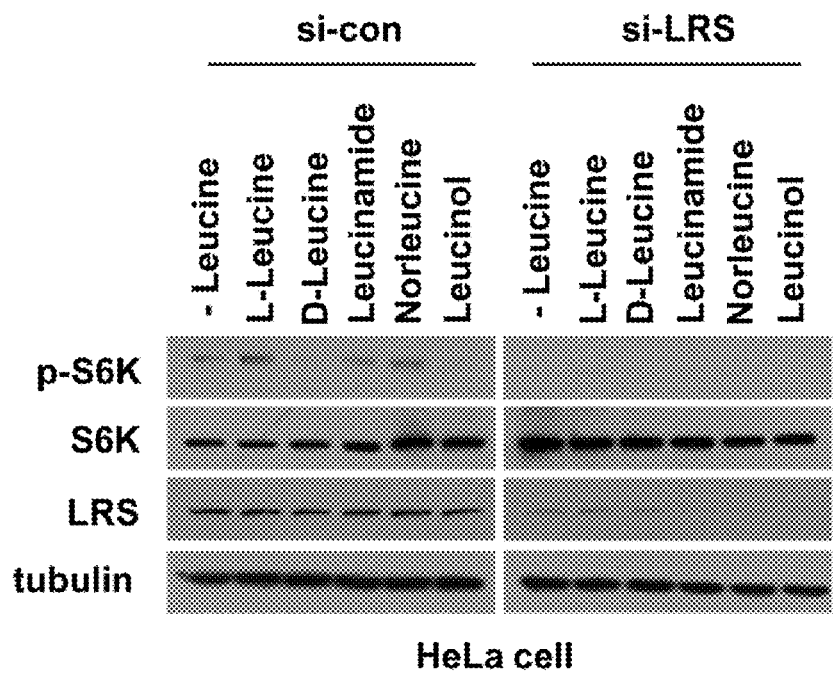

In FIG. 9d, HeLa cells were transfected with control or LRS siRNAs for 48 hours, and leucine- or leucine analogues-stimulated S6K phosphorylation was determined by immunoblotting. The concentration of L-leucine and leucine amide was 0.8 mM and the concentration of D-leucine, norleucine, and leucinol was 8 mM.

Figure 10A:
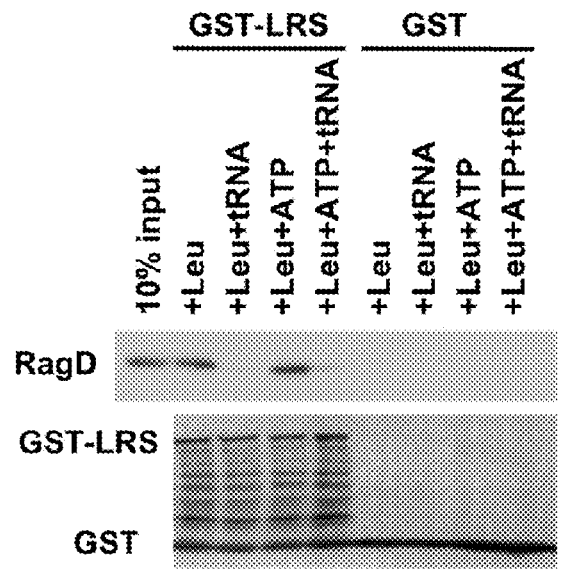
FIGS. 10a-10e include experimental results showing that LRS is involved in mTORC1 activation in tRNA-independent manner.

FIGS. 10a-10E show that LRS is involved in mTORC1 activation in tRNA-independent manner. In FIG. 10a, the effect of tRNA on in vitro LRS-RagD binding. 293T cell lysates were incubated with purified GST or GST-fused LRS in the presence of the combinations of leucine (0.1 mM), ATP (0.1 mM), and tRNA$^{Leu}$ (25 µg). The precipitated RagD was determined by immunoblotting with anti-RagD antibody.

Figure 10B:
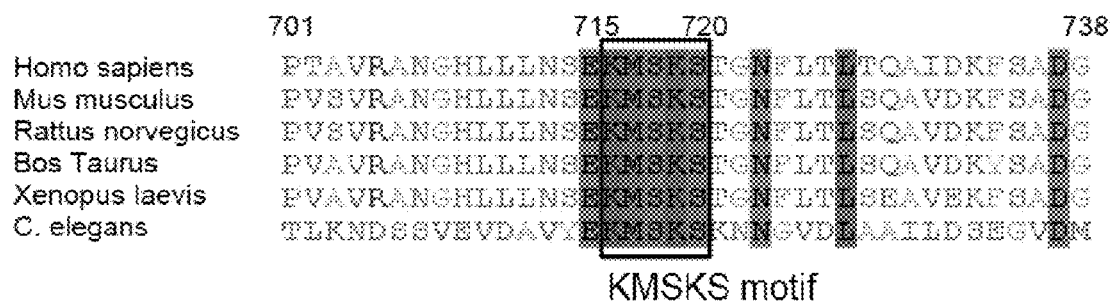

In FIG. 10b, the primary sequence alignment of several species leucyl-tRNA synthetases is shown. The class 1a conserved KMSKS motif, which is important to tRNA binding, is boxed in black.

Figure 10C:
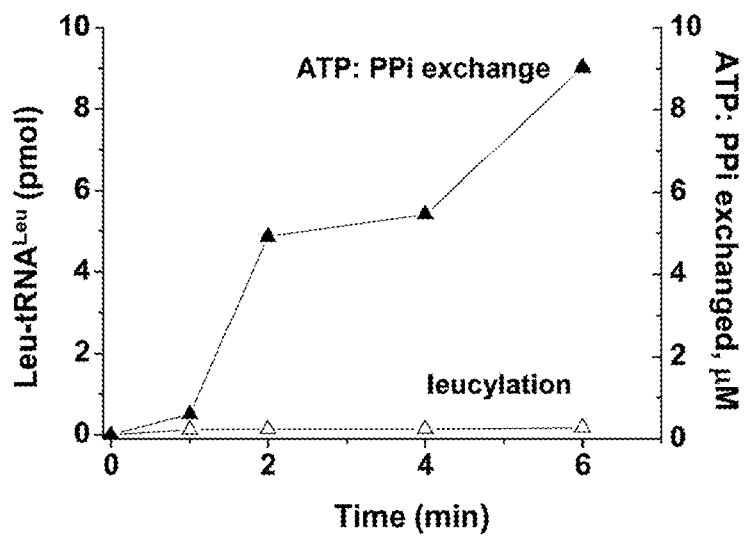
Figure 10D:
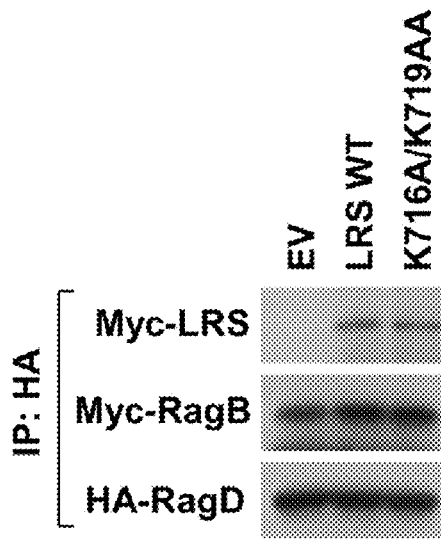

In FIG. 10c, leucylation and ATP-PPi exchange activities by LRS K716A/K719A mutant were carried out as shown. In FIG. 10d, the effect of K716A/K719A mutant on RagD binding is shown. 293T cells were transfected with myc-tagged LRS WT or mutant, and HA-tagged RagD for 24 hours. Cell lysates were immunoprecipitated with anti-HA antibody and the co-precipitated LRS and RagD were determined by immunoblotting with anti-myc and anti-myc antibodies.

Figure 10E:
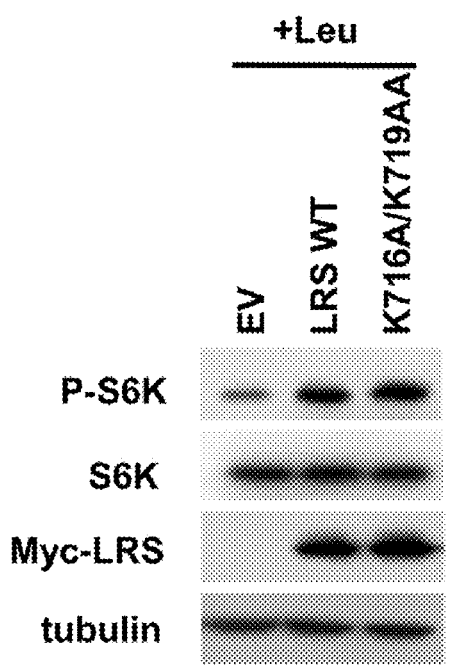

In FIG. 10e, 293T cells were transfected with the indicated cDNAs for 24 hours, and leucine-dependent S6K phosphorylation was determined by immunoblotting.

Figure 11A:
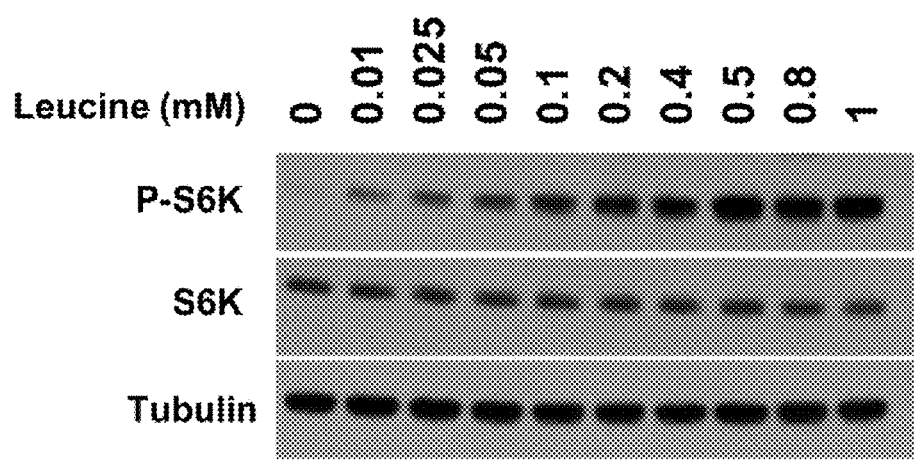
FIGS. 11a-11c include experimental results showing that Leucine activates mTORC1 in dose-dependent manner.
Figures 11B, 11C:
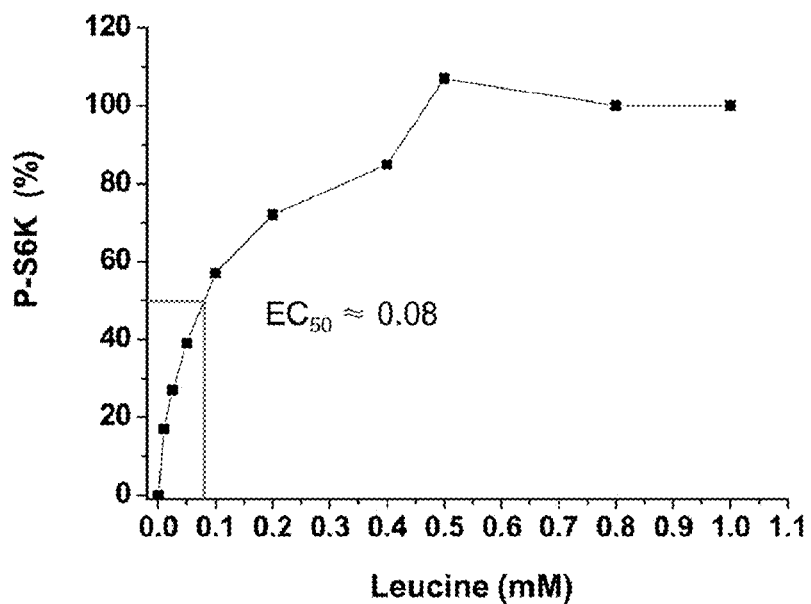

FIGS. 11a-11c FIG. 11 shows that Leucine activates mTORC1 in dose-dependent manner. In FIG. 11a, 293T cells were treated with leucine at the indicated concentration for 5 min. Leucine-dependent S6K phosphorylation was determined by immunoblotting. In FIG. 11b, quantitation of p-S6K band in FIG. 11a is shown. EC50 of leucine stimulation of mTORC1 was about 80 mM. In FIG. 11c, kinetic parameters for leucylation and ATP-PPi exchange activity of WT LRS is shown.

Figure 12:
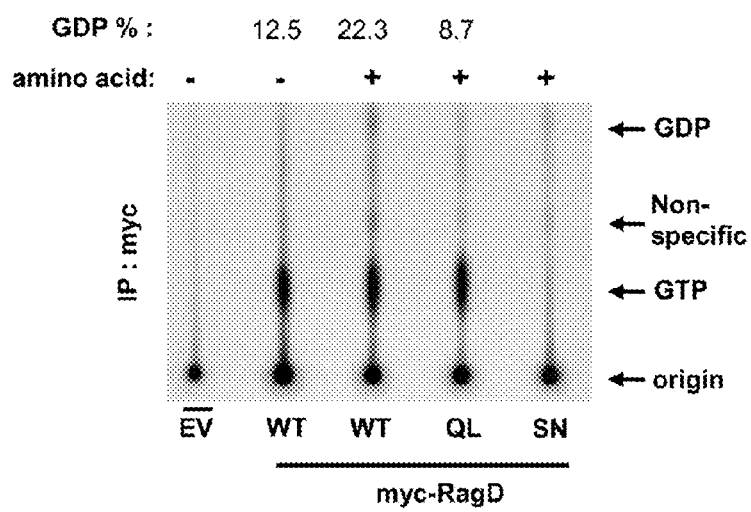
FIG. 12 includes experimental results showing the effect of amino acid stimulation on GTP/GDP status of RagD.

FIG. 12 shows the effect of amino acid stimulation on GTP/GDP status of RagD. Wild type and mutant forms of myc-RagD were transfected into 293T cells and the cells were labeled with 32P-phosphate. Myv-RagD was immunoprecipitated and the bound nucleotides were eluted and analyzed by TLC. EV means control empty vector.

Figure 13A:
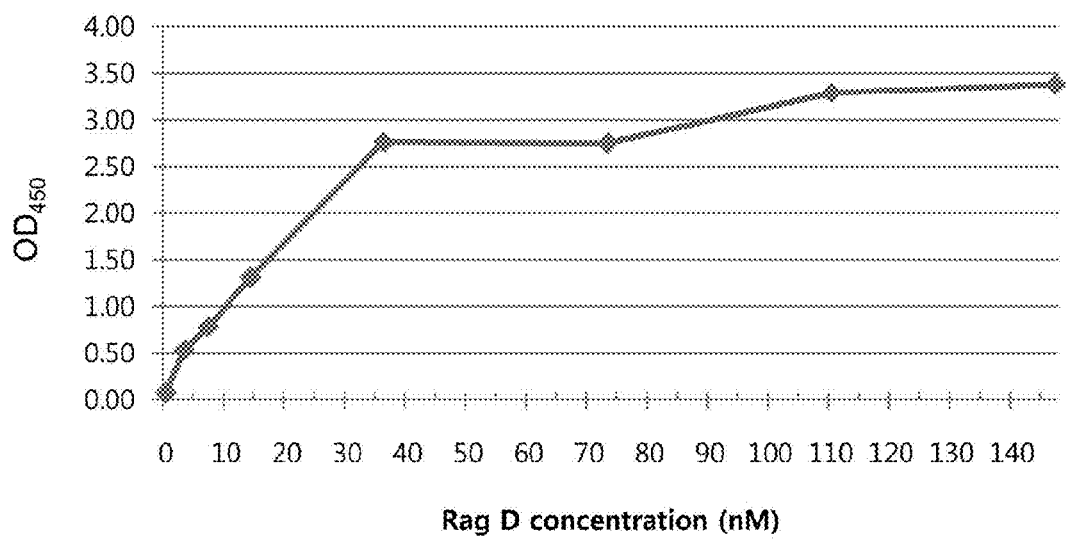
FIGS. 13a and 13b are graphs showing ELISA assay results for measuring binding affinity between LRS and RagD.
Figure 13B:
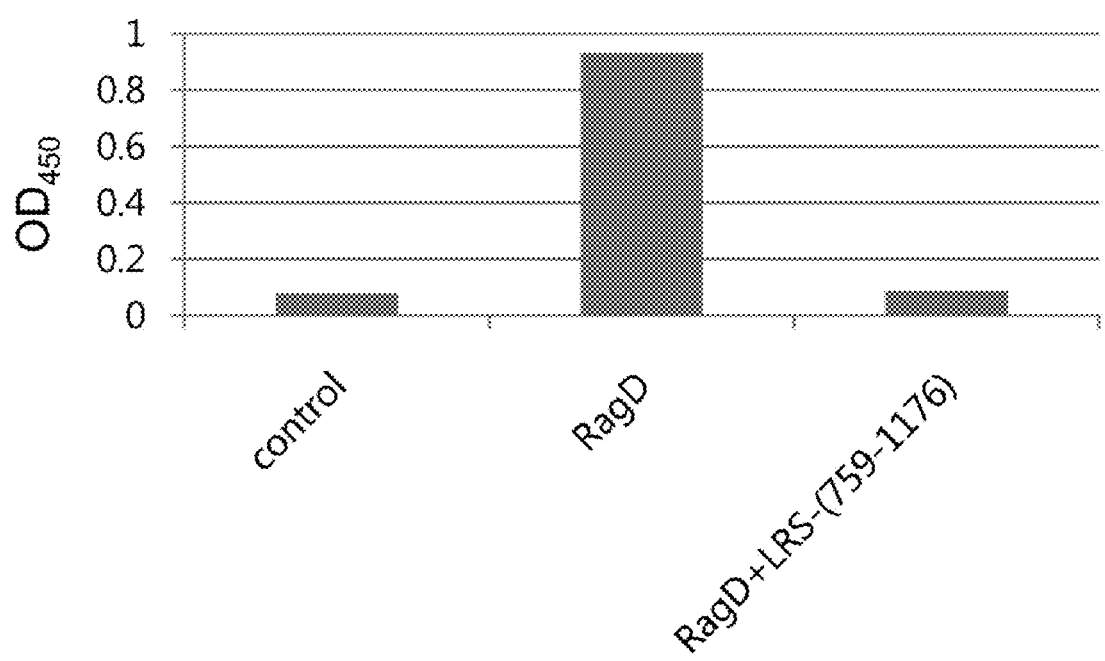

FIGS. 13a and 13b show ELISA assay results for measuring binding affinity between LRS and RagD. In FIG. 13a, ELISA results showed that RagD protein binds to LRS-(1-1176) in a dose dependent manner (96 well plate is coated with LRS-(1-1176) (500 ng/ml in carbonate buffer). GST is a negative control. RagD protein was used as GST-RagD form. Primary antibody is anti-GST antibody (Z-5, 1:100 dilution). Secondary antibody is HRP-conjugated anti-rabbit antibody (1:5000 dilution)).

In FIG. 13b, the comparison result of binding affinity for control (GST), RagD and RagD+LRS-(759-1176) on a 96 well plate coated with LRS-(1-1176) is shown. LRS-(759-1176) decreased the binding affinity of RagD on plate coated with LRS-(1-1176).

<Methods>

1. Cell Culture and Reagents

HEK293T cells and HeLa cells were grown in DMEM (Hyclone) containing 10% fetal bovine serum and antibiotics. CHO-tSH1 cells were a kind gift from Dr. Mike Clemens. CHO-tSH1 cells were grown in Dulbecco's modified Eagle's medium/Nutrient Mixture Ham's F-12 (Sigma) supplemented with 9% (v/v) fetal bovine serum, 100 mg/ml streptomycin sulfate, and 100 units/ml penicillin G at 34° C. The tsH1 line contains a temperature-sensitive leucyl-tRNA synthetase that is active at 34° C., but defective at 39.5° C.

Amino acid deprivation and addition experiments were performed using DMEM (+AA) and DPBS containg 25 mM glucose, 1 mM sodium pyruvate, lx MEM vitamins (Invitrogen) (−AA). L-Leucine, D-Leucine, L-Leucinamide, Leucinol, Norleucine (Sigma Aldrich) were dissolved in PBS [pH 7.6], and treated at the concentration of 0.8 mM or 8 mM. [$^{32}$P]pyrophosphate (80.70mCi/mL) was obtained from PerkinElmer Life Sciences. [$^{3}$H]Leucine was obtained from American Radiolabeled Chemicals. RagC and RagD siRNAs were obtained from Invitrogen.

2. Amino Acids or Leucine Starvation and Stimulation of Cells

For leucine depletion, cells were rinsed with leucine-free DMEM twice, incubated in leucine-free DMEM for 60 minutes, and stimulated with 52 mg/ml leucine for 5-60 minutes. For amino acid starvation, cells were rinsed with and incubated in DPBS containing 25 mM glucose, 1 mM sodium pyruvate, lx MEM vitamins for 60 minutes, and replaced with and incubated in DMEM for 5-60 minutes.

3. Antibodies and Plasmids

Antibodies were obtained from the following sources: anti-mTOR blocking peptide, antibodies to mTOR (for IP), HA, c-MYC, laminA, as well as HRP-labeled anti-mouse, anti-rabbit secondary antibodies from Santa Cruz Biotechnology; antibodies to phospho-T389 S6K1, phospho-5473 Akt/PKB, phospho-T308 Akt, S6K1, Akt, LC3, RagC, RagD from Cell Signaling Technology; antibodies to LAMP2 (H4B4), mTOR (Y391), Raptor from Abcam (for Western) antibodies to Raptor, mTOR, FLAG from Invitrogen (for Western, IF, IP) mouse monoclonal antibody to mTOR, clone 2ID8.2 from Millipore (for Western) LysoTracker Red DND-99 from Molecular Probe; monoclonal mouse anti-calnexin antibody from BD Pharmigen; HA-tagged mTORC1 components constructs including RagA, RagB, RagC, RagD, mTOR, Raptor, GbL, Rheb1 were generously provided by Dr. D-H. Kim (University of Minnesota) and Dr. E. J. Kim (Catholic University of Daegu). All other DNA constructs including LRS, IRS, MRS, and EPRS were laboratory stocks. Transfection was performed using Geneporter system (Gene Therapy System).

4. Preparation of Cell Lysate and Immunoprecipitation

Cells were dissolved in the lysis buffer containing 1% Triton X-100, 40 mM HEPES (pH7.4), 2 mM EDTA, 10 mM pyrophosphate, 10 mM glycerophosphate, and protease inhibitor cocktail. The lysates were centrifuged at 13,000 rpm for 30 minutes. We then fractionated 20 µg of the extracted proteins by SDS-PAGE. For immunoprecipitations, the cells were lysed (50 mM Tris-HCL (pH 7.4), 10 mM NaCl, 1 mM EDTA, 0.5 mM EGTA, 1 mM MgCl$_2$, 0.1% CHAPS, and 0.5% Triton X-100, 1 mM phenylmethylsulfonyl fluoride) and the primary antibodies were added to the lysates and incubated with rotation for 2 hr at 4° C. A 50% slurry of protein agarose G-sepharose was then added and the incubation continued for an additional 4 hr. After washing three times with the ice-cold lysis buffer, the precipitates were dissolved in the SDS sample buffer and separated by SDS-PAGE.

5. Immunofluorescence Staining

Cells were seeded onto cover slips and fixed with 100% aceton, for 5 min, at −20° C. After incubation with PBS blocking buffer containing 2% BSA, the cells were incubated with the primary antibody (1:100) for 2 h and Alexa488- or Alexa595-conjugated secondary antibody (1:1,000) in blocking buffer containing 2% BSA and 10% fetal bovine serum for 1 h. Nuclei were stained with DAPI.

After washing with PBS, the cells were mounted and observed via confocal laser scanning microscope (Nikon MR).

6. Mutations of LRS and RagD

Point mutations in LRS and RagD were generated via site-directed mutagenesis by using a QuikChange kit (Stratagene), and the mutants were confirmed by DNA sequencing.

7. Subcellular Fractionation

Cells were seeded and cultivated to 70% confluence. The cells were washed by amino-acid free media 3 times, and normal media was added for 5 min. Then lysosome fraction was extracted using lysosome isolation kit (SIGMA-ALDRICH) following the manufacturer's instructions. Briefly, extraction buffer added to the cells, cells were broken using Dounce homogenizer with 20 strokes. After centrifugation the sample at 1,000 g for 10 min, the supernatant was further centrifuged at 20,000 g for 20 min. The pellet was resuspended in extraction buffer (lysosomal fraction).

8. Time-Lapse Live Cell Imaging

Cell imaging was performed using a confocal laser scanning microscope (Nikon A1R). All images were captured with a CFI Plan Apochromat VC objective lens (60×/1.40 Oil) at a resolution of 512×512 using digital zooming. All images were stored as ND or JPG2000 files, which are standard formats for Nikon A1Rsi confocal microscope.

9. Image Analysis

Cell images were used for quantitative analysis. This process was performed with Nikon imaging software NIS-element AR 64-bit version 3.00. Image file formats were transferred from ND or JPG2000 files to ICS or TIFF formats using NIS-element software. Quantitative analysis of lysosomal colocalization was performed using the "Time-measurement" tool for "Region Of Intensity" (ROI) in the NIS-element software. After ROIs were defined according to localization of LysoTracker, localization of other components was measured using the defined ROIs. Relative Fluorescence Units (RFU) was normalized against the initial intensity of ROI, and then plotted using OriginPro 7.5. For the quantitative analysis of colocalization, we also used ImageJ colocalization finder plugin. The index of co-localization corresponds to the mean±S.D of the overlap coefficient (R)*100 obtained for more than 10 cells for each co-labeling. The ratio between green and red signals is ranged between 0.8 and 1.2.

10. In Vitro Pull-Down Assay

Recombinant LRS or RagD fragment proteins were expressed as GST fusion proteins and purified by glutathione sepharose. The interactions between RagD fragments and myc-LRS overexpressed cell lysates or between LRS fragments and HA-RagD overexpressed cell lysates were tested using in vitro binding assays. Binding assay was conducted in 25 mM Tris-HCl buffer (pH7.4) containing 10 mM NaCl, 1 mM MgCl$_2$, 1 mM EDTA, 0.5 mM EGTA, and 0.5% Triton X-100.

11. Cell Size Determinations

For measurement of cell size using forward scatter units (FSC) with unfixed cells. 293T cells were plated, washed once with PBS, and resuspended in PBS containing 0.1% serum, 5 mM EDTA, 5 ng/ml propidium iodide (PI; Sigma). Samples were analyzed by FACS analysis (FACS caliber; Becton Dickinson) for cell size (FSC). The mean of FSC of G1 phase cells was determined.

12. ATP-PPi Exchange Assay

The ATP-PPi exchange reaction was performed in a reaction mixture containing 2 mM [$^{32}$P]pyrophosphate (PPi) (80.70 mCi/mL), 50 mM HEPES-KOH (pH 7.6), 2 mM MgCl$_2$, 8 mM KF, 4 mM ATP, and various concentrations of leucine and 25 nM of LRS. Reaction were initiated with enzymes and conducted in a 37° C. heat block. Aliquots (10 ul) were taken at different time points, and the reactions were stopped using 1ml of quenching buffer (50 mM NaPPi, 3.5% HClO$_4$, 2% activated charcoal). The charcoal suspension was filtered through a Whatman GF/A filter, washed four times with 5 ml of water and rinsed with 10 ml of 100% ethanol. The charcoal powder on the filters was dried, and the synthesized [$^{32}$P]ATP was counted using a scintillation counter (Beckman Coulter).

13. Leucylation Assay

The leucylation assay was carried out in a buffer containing 1 mM spermine, 50 mM HEPES-KOH (pH7.6), 25 mM KCl, 5 mM MgCl$_2$, 4 mM ATP, 2 mg/ml bovine liver tRNA$^{Leu}$, various concentrations of [$^3$H]Leu (60 Ci/mmol), and 10-100 nM of LRS. Reactions were initiated with enzyme and conducted in a 37° C. heat block. Aliquots (10 ul) were taken at different time points and quenched on Whatman filter pads that were presoaked with 5% trichloroacetic acid (TCA). The pads were washed three times for 10 min each with cold 5% TCA, and once with cold 100% ethanol. The washed pads were then dried. Radioactivity was quantified in a scintillation counter (Beckman Coulter)

14. In Vitro GTPase Assay

GTPase assays were conducted in assay buffer (20 mM piperazine-N,N9-bis(2-ethanesulfonic acid), 20 mM HEPES, 5 mM MgCl$_2$, 125 mM NaCl, 5 mM KCl at pH 7.0, 0.5 mM GTP) containing 0.1% bovine serum albumin in a final volume of 200 ml using GTPase assay kit (Innova Biosciences) according to manufacturer's instructions.

15. In Vivo GTPase Assay 293T cells were washed with phosphate-free DMEM and incubated with 1 ml of phosphate-free DMEM for 60 min. Cells were then incubated with 100 μC of [$^{32}$P]phosphate/ml for 8 hr. After labeling, cells were lysed with pre-chilled lysis buffer (0.5% NP-40, 50 mM Tris [pH 7.5], 100 mM NaCl, 10 mM MgCl$_2$, 1 mM dithiothreitol (DTT), 1 mM phenylmethylsulfonyl fluoride, 10 μg of leupeptin/ml, and 10 μg of aprotinin/ml), for 30 min on ice. The lysates were then centrifuged at 12,000×g for 15 min at 4° C. The supernatant (160 μl) was transferred to a fresh tube, and 16 μl of NaCl (500 mM) was added to inhibit GAP activity. Myc-RagD was then immunoprecipitated with anti-Myc antibody and protein-G sepharose bead for 1 hr at 4° C. The beads were washed with wash buffer 1 (50 mM Tris [pH 8.0], 500 mM NaCl, 5 mM MgCl$_2$, 1 mM DTT, 0.5% Triton X-100) three times at 4° C., and then washed with wash buffer 2 (50 mM Tris [pH 8.0], 100 mM NaCl, 5 mM MgCl$_2$, 1 mM DTT, 0.1% Triton X-100) three times at 4° C. The myc-RagD-bound nucleotideswere eluted with 20 μl of elution buffer (2 mM EDTA, 0.2% sodium dodecyl sulfate, 1 mM GDP, 1 mM GTP) at 68° C., for 10 min. The eluted nucleotides were applied onto polyethyleneimine cellulose plates (Baker-flex) and developed in 0.75 M KH$_2$PO$_4$[pH 3.4] solution. GTP and GDP were visualized and quantified by a phosphoimager.

16. RT-PCR

RNAs were extracted from the cultivated cells using RNA extraction kit (RNeasy Mini). Total RNA (1 mg) was used for reverse transcription with 1 ml dNTP (2.5 mM each), 1 ml random hexamer (5 mM) and 200 unit of MMLV reverse transcriptase in 20 ml reaction.

After 1: 4 dilution of the cDNA solution, 1 ml was used for PCR reaction (Takara).

```
RagC, Sense:
                                    (SEQ ID NO: 19)
5'-TCGGCTACGGCGTGGAGGAG-3', RagC, Antisense:
                                    (SEQ ID NO: 20)
5'-CGCCCCCCGGACCACAGCCA-3', RagD, Sense:
                                    (SEQ ID NO: 21)
5'-TGAGCTGGTGGGGCTAGCGG-3', RagD, Antisense:
                                    (SEQ ID NO: 22)
5'-GGGTCACTGAAGTCCAGAACTC-3'.
```

17. ELISA Assay for Measuring Binding Affinity Between LRS and RagD.

In order to examine whether the LRS and RagD proteins bind to each other, primers represented by SEQ ID NOs: 1 to 8 were prepared.

TABLE 1

Primer set used for LRS fragment synthesis

| Primers | Sequence | Seq. No. |
|---|---|---|
| LRS-(1-1176) sense | GGA ATT CCA TAT GGC GGA AAG AAA AGG AAC AGC CAA AGT | 4 |
| LRS-(1-1176) antisense | CGG GAT CCT AAA TGA ACC AGA TAG ATT ATT GTA TCG | 5 |
| LRS-(759-1176) sense | GGA ATT CCA TAT GGC AGA TGC AGG TAT TCT CCG | 6 |
| RagD-(1-400) sense | CGG GAT CCA TGA GCC AGG TGC TGG GGA AG | 7 |
| RagD-(1-400) antisense | CGC TCG AGC TAC AGC AGC ACT CTA GGG GTC | 8 |

First, each fragment of LRS was synthesized by PCR amplification using the cDNA of LRS as a template and a primer set (Table 1) specific for each fragment. The PCR amplification was performed under the following conditions: predenaturation of the template DNA at 95° C. for 2 min; and then 30 cycles, each consisting of 30 sec at 95° C., 30 sec at 56° C., and 3 min and 30 sec at 72° C.; followed by final extension at 72° C. for 10 min. Each of the PCR products was digested with NdeI and BamHI and ligated into a pET 16a vector (Novagen) digested with the same restriction enzymes. E. coli BL21(DE3) cells were transformed with the vector and cultured to induce the expression of peptides. Each peptide expressed as a His-tag fusion protein was purified by Ni-chelating agarose. To remove lipopolysaccharide, the protein solution was dialyzed in pyrogen-free buffer (10 mM potassium phosphate buffer, pH 6.0, 100 mM sodium chloride). After dialysis, the protein was loaded to polymyxin resin (Bio-Rad) equilibrated with the same buffer, after which it was incubated for 20 minutes, and then eluted, thereby preparing each fragment of LRS.

A fragment of RagD was synthesized by PCR amplification using the cDNA of LRS as a template and a primer set (Table 1) specific for each fragment. The PCR amplification was performed under the following conditions: predenaturation of the template DNA at 95° C. for 2 min; and then 30 cycles, each consisting of 30 sec at 95° C., 30 sec at 56° C., and 1 min and 30 sec at 72° C.; followed by final extension at 72° C. for 5 min. Each of the PCR products was digested with BamHI and XhoI and ligated into a pGEX4T3 vector (GE healthcare) digested with the same restriction enzymes. E. coli BL21 cells were transformed with the vector and cultured to induce the expression of peptides. Each peptide expressed as a GST-tag fusion protein was purified by GSH agarose. To remove lipopolysaccharide, the protein solution was dialyzed in pyrogen-free buffer (10 mM potassium phosphate buffer, pH 6.0, 100 mM sodium chloride). After dialysis, the protein was loaded to polymyxin resin (Bio-Rad) equilibrated with the same buffer, after which it was incubated for 20 minutes, and then eluted, thereby preparing each fragment of RagD.

Purified GST-RagD was incubated with His-LRS-(1-1176) coated on a plate at various concentrations and was subjected to ELISA using anti-GST antibody (Z-5, 1:100 dilution) and HRP-conjugated anti-rabbit antibody (1:5000 dilution), and the results of the ELISA are shown in FIG. 13.

<Results>

1. Identification of LRS as an mTOR-Associated Protein

To investigate whether LRS has an additional activity, separated from its catalytic role within the ARS complex, we first examined its subcellular distribution. Cell fractionation analysis showed that large amount of LRS was localized to endomembrane fraction with mTOR as well as cytosol where IRS and MRS were mainly found (FIG. 1a). Immunofluorescence analysis showed that LRS was well co-localized with the ER marker, calnexin, and the endosome marker, EEA1. Minor amount of LRS showed co-localization with lysosome marker, LAMP2, but little with the Golgi marker, GM130 (FIG. 1b). Previous report showed that amino acids induce the movement of mTORC1 to lysosomal membranes (Sancak et al., 2010). Thus, we examined the lysosomal localization of LRS upon amino acid stimulation (FIG. 1c and FIG. 8). We biochemically analyzed the lysosomal localization of LRS using sucrose gradient fractionation. Amino acid depletion decreased lysosomal mTOR, Raptor, and LRS, but amino acid supplement clearly induced lysosomal translocation of LRS as well as mTOR and Raptor (FIG. 1c). Quantitative analysis of lysosomal colocalization was performed using time lapse confocal live cell imaging. Leucine depletion decreased colocalization of EGFP-LRS with lysosomal marker, LysoTracker. However, leucine supplementation recovered the colocalization of EGFP-LRS with lysosome within 10 min (FIG. 8a). Colocalization of control EGFP with LysoTracker showed little change by the depletion or addition of leucine (FIG. 8b). The intensity of colocalization was quantified by NIS-element software. Lysosomal localization of LRS gradually decreased for 50 min after leucine depletion, but lysosomal localization of LRS was rapidly induced within 10 min after leucine supplementation (FIG. 8c). These results suggest that leucine induces the movement of LRS to lysosomal fraction as well as mTORC1.

We investigated whether LRS would form a complex with mTORC1. HEK293T cell lysates were immunoprecipitated with anti-goat IgG, anti-mTOR, and anti-actin antibodies and then the immunoprecipitates were analyzed with anti-LRS, anti-IRS, anti-mTOR, and anti-Raptor antibodies. LRS was coprecipitated with mTOR and Raptor only in mTOR immunoprecipitates (FIG. 1d). The intensity of LRS band decreased significantly when competitive epitope peptide against mTOR antibody was added after cell lysis, indicating that LRS specifically interacted with mTORC1. Interestingly, isoleucyl-tRNA syntheatse (IRS) was not detected within mTOR immunoprecipitates, consistent with FIG. 1a, implying that LRS in mTORC1 should be different from that within ARS complex. To examine this possibility, HEK293T cells were transfected with myc-tagged LRS or methionyl-tRNA synthetase (MRS) and cell lysates were immunoprecipitated with anti-myc antibody and then the immunoprecipitates were analyzed with anti-mTOR and anti-Raptor antibodies. mTOR and Raptor were only detected in LRS immunoprecipitates (FIG. 1e). Furthermore, LRS was well co-localized with mTOR (FIG. 1f) and with Raptor (FIG. 1g). Consistent with FIG. 1d and E, MRS and IRS were not co-localized with mTORC1 (Figure if and G). These results suggest that LRS in mTORC1 is different from that bound to ARS complex.

2. Effect of LRS on mTORC1 Activation, Lysosomal Localization, Cell Size, and Autophagy To see the importance of LRS in the control of mTORC1 activation, we monitored the effect of LRS knockdown on mTORC1 activation using 6 different kinds of LRS siRNA (Table 2). All siRNAs significantly suppressed the expression of LRS and inhibited amino acid-induced S6K phosphorylation (FIG. 2a). Next, we monitored the specific involvement of LRS on mTORC1 activation. Knockdown of mTOR and LRS, but not of IRS, MRS, or valyl-tRNA synthetase (VRS), significantly inhibited amino acid-induced S6K phosphorylation (Table 3, FIGS. 2b and 2c). Also, LRS specifically mediated leucine-induced S6K phosphorylation (FIG. 2c). These results suggest that endogenous LRS is involved in amino acid-induced mTORC1 activation pathway. Next, we monitored the effect of LRS knockdown on amino acid-induced lysosomal localization of mTORC1. While amino acid supplement induced lysosomal localization of mTOR and Raptor in si-controltransfected cells, lysosomal localization of mTOR and Raptor was not observed in si-LRS-transfected cells (FIG. 2d). Therefore, this result suggests that LRS mediates amino acid-induced lysosomal localization of mTORC1.

mTORC1 is known to control cell size (Fingar D C, Salama S, Tsou C, Harlow E, Blenis J. Mammalian cell size is controlled by mTOR and its downstream targets S6K1 and 4EBP1/eIF4E. Genes Dev. 16 (2002), pp 1472-1487). If mTORC1 pathway is inhibited, it leads to a reduction in cell size. Consistent with LRS being a mediator of amino acid signaling to mTORC1, LRS-suppressed cells were smaller in size than control cells (FIG. 2e upper panel). However, IRS, VRS, and MRS knockdown had no effect on cell size (FIG. 2e lower panel). Quantitative analysis of cell size regulation was performed and we confirmed that rapamycin treatment or LRS knockdown specifically reduced cell size (FIG. 2f). In addition, autophagy, a process normally inhibited by mTORC1 pathway, was activated in LRS downregulated cells, as detected by the increase of LC3-II/LC-3-I ratio (FIG. 2g). Also, downregulation of endogenous LRS specifically activate autophagy, as detected by an increase compared to in control cells in the size and the number of GFP-LC3-II puncta (FIGS. 2g and 2i). These results suggest the specific role of LRS in the regulation of mTORC1 pathway.

TABLE 2 siRNA sequences targeting LRS

| Location | siRNA sequence (5' to 3') | Seq. No. |
|---|---|---|
| 105 (5' UTR) | CAGCAGGUGUGAAGCGUGUGCUUUA | 9 |
| 195 (5' UTR) | CCAGGGUCAUUGUCGUGGAUUUGCA | 10 |

TABLE 2-continued siRNA sequences targeting LRS

| Location | siRNA sequence (5' to 3') | Seq. No. |
|---|---|---|
| 396 (CDS) | CAUAUAUGAAUGGACGCCUUCAUUU | 11 |
| 792 (CDS) | CGCCACUGGCUAUUCAGGAUUUAAA | 12 |
| 1312 (CDS) | UGGUGCAUCACUUUCUGCACCUUUA | 13 |
| 3844 (5' UTR) | CAGAACCUUAGGCUGGACCUAAAUA | 14 |

TABLE 3 siRNA sequences targeting mTOR, IRS, VRS, and MRS

| Target | siRNA sequence (5' to 3') | Seq. No. |
|---|---|---|
| mTOR | GGAAGUACCCUACUUUGCUUGAGGU | 15 |
| IRS | GGAAGCCAGAUUGUCAGCCCUCUAU | 16 |
| VRS | AGAAGAGGAUGUCAUGACCGGUCUC | 17 |
| MRS | CUACCGCUGGUUUAACAUUUCGUUU | 18 |

3. LRS Directly Interacts with RagD GTPase

We investigated whether LRS would interact with the key components of mTORC1 pathway. The interaction was tested by in vitro pull-down assay using GST-LRS and HA-tagged mTORC1 molecules. GST-LRS specifically co-precipitated with HA-RagD, but not with others (FIG. 3a), indicating their specific and direct interaction. Co-immunoprecipitation assay also showed the specific interaction of LRS with RagD, but not with RagA, RagB, and RagC (FIG. 3b), despite its sequence homology with RagC (81.1% identity) (Sekiguchi T, Hirose E, Nakashima N, Ii M, Nishimoto T. Novel G proteins, Rag C and Rag D, interact with GTP-binding proteins, Rag A and Rag B. J Biol. Chem. 276 (2001), pp7246-'725'7). Next, we examined specific interaction between LRS and RagD. RagD only interacted with LRS, but not with IRS, MRS, or EPRS (FIG. 3c). Since Rag GTPases form a heterodimer for mTORC1 activation, we examined which heterodimer of Rag GTPases is a specific binding partner for LRS. Consistently, LRS showed specific interaction with RagD heterodimer, but not with RagC heterodimer (FIG. 3d). Interestingly, RagB/RagD heterodimer showed higher affinity for LRS than RagA/RagD heterodimer (FIG. 3d). We also investigated whether endogenous LRS can form a complex with Rag B/RagD heterodimer and found that endogenous LRS also can form a complex with Raptor and RagB/RagD heterodimer (FIG. 3e). Next, we determined the peptide region of RagD that is involved in the interaction with LRS by in vitro pull-down assay. The myc-tagged LRS was precipitated with GST-RagD fragments. The peptides spanning aa 1-400 and 230-400 of RagD interacted with LRS (FIG. 3f).

As shown in FIG. 3b, LRS interacted with RagD, but not with RagC in spite of sequence homology. Therefore, we hypothesized that the C-terminal 230-400 region of RagD may confer the binding specificity for LRS. Within 230-400 region of RagD, 371-400 region of RagD only has sequence variability compared with that of RagC. To confirm this hypothesis, we prepared different point mutants of RagD at the amino acid position of 379, 383, 385, 388, and 389, and tested whether these mutations would affect the interaction with RagB or LRS. While the RagD mutants at 379, 383, and 389 were coimmunoprecipitated with LRS, the mutants at 385 and 388 lost their binding capability (FIG. 3g), further confirming the interaction of the C-terminal region of RagD with LRS. In contrast, all the mutants retained the binding ability to RagB, indicating that RagD has different binding sites for RagB and LRS. Conversely, we determined the peptide region of LRS that is involved in the interaction with RagD by in vitro pull-down assay. The HA-tagged RagD-transfected cell lysates were pull-downed with GST-fused LRS fragments. The peptide spanning aa 951-1176 of LRS interacted with RagD (data not shown), implying the C-terminal region of LRS for the interaction with RagD. To further confirm the RagD-binding site of LRS, we prepared different deletion mutants of LRS, incubated them with HA-tagged RagD and tested which deletion would affect the interaction with RagD. While the peptides spanning 759-1120, 759-1176, and 951-1176 of LRS bound to RagD, the peptide spanning 971-1176 lost its binding capability (FIG. 3h), implying the peptide region spanning 951-971 of LRS for the interaction with RagD. To confirm this conclusion, we also prepared alanine substitutions at S953/V954, R956/K957, and N969/K970 located in the RagD binding region of LRS. We then tested whether any of these mutations would affect the interaction with RagD. In the immunoprecipitation assay, while the two mutants (S953A/V954A and R956A/K957A) showed interaction with RagB/RagD heterodimer, N969A/K970A mutant lost its binding capability (FIG. 3i).

4. LRS Forms Molecular Complex with RagD and Raptor in Amino Acid-Dependent Manner.

We investigated whether Raptor would interact with RagD and LRS in amino acid-dependent manner. 293T cells were treated with amino acid for 5 min and protein lysates were prepared to perform co-immunoprecipitation of Raptor with LRS and RagD. The interaction of Raptor with RagD and LRS increased after amino acid supplementation (FIG. 4a). Next, we examined whether LRS would interact with RagD in amino acid-dependent manner. While RagB/RagD heterodimer formation would not be affected by amino acid, LRS interacted with RagB/RagD heterodimer in amino acid-dependent manner (FIG. 4b), implying that LRS-RagD interaction is also amino acid-dependent.

To assess the importance of LRS for the interaction of RagD with Raptor, we compared the RagD-Raptor interaction in the presence or absence of exogenous LRS. In the absence of exogenous LRS, RagD slightly interacted with Raptor upon amino acid supplementation. However, overexpression of LRS significantly enhanced amino acid-induced RagD-Raptor binding (FIG. 4c). Conversely, down-regulation of endogenous LRS weakened amino acid-induced RagD-Raptor binding (FIG. 4d), suggesting that LRS augments RagD-Raptor binding.

5. LRS Functions as a Leucine Sensor for mTORC1 Signaling

LRS is a class I aminoacyl-tRNA synthetase and has a conserved HIGH motif, which serves as an ATP-binding site (FIG. 5a). Previous structural study demonstrated that the large hydrophobic pocket to accommodate the substrate leucine side chain is formed by Phe50 and Tyr52, highly conserved residues among leucyl-tRNA synthetases of different species (FIG. 5a) (Cusack S, Yaremchuk A, Tukalo M. The 2A crystal structure of leucyl-tRNA synthetase and its complex with a leucyl-adenylate analogue. EMBO J. 19(2000), pp. 2351-2361). The α-amino group of leucine makes hydrogen bond to the carbonyl oxygen of Phe50 and the sulfate in leucyl-adenylate hydrogen bonds to the main chain of Tyr52 (Cusack et al., 2000). Alanine substitution of these conserved Phe50 and Tyr52 significantly suppressed leucylation activity of LRS due to the increased Km for leucine (FIG. 5b and Table 4). To access the importance of leucine binding of LRS for the activation of mTORC1 and for the complex formation with RagD and Raptor, we investigated the effect of F50A/Y52A mutant of LRS on them. Leucine-induced S6K phosphorylation was enhanced by the introduction of WT LRS, but not of the F50A/Y52A mutant (FIG. 5c). Also, F50A/Y52A mutant lost the ability to bind RagB/RagD heterodimer (FIG. 5d), and could not mediate the association of RagB/RagD heterodimer and Raptor (FIG. 5d). These results clearly show that leucine sensing by LRS is critical for mTORC1 activation.

TABLE 4

| Substrates | Constants | LRS WT Leucylation | LRS F50A/Y52 Leucylation |
|---|---|---|---|
| Substrates | Constants | Leucylation | Leucylation |
| Leucine | $K_m$(mM) | 0.0159 ± 0.0004 | 0.536 ± 0.063 |
| Leucine | $K_{cat}$(S$^{-1}$) | 0.368 ± 0.009 | 0.2 ± 0.04 |
|  | $K_{cat}$/Km(S$^{-1}$mM$^{-1}$) | 22.9 ± 0.57 | 2.71 ± 0.232 |

Previous efforts to identify leucine sensor for mTORC1 activation were analyzed by examining the effects of leucine analogues and emperature-sensitive leucyl-tRNA synthetase mutant (Lynch C J, Fox H L, Vary T C, Jefferson L S, Kimball S R. Regulation of amino acid-sensitive TOR signaling by leucine analogues in adipocytes. J Cell Biochem. 77 (2000), pp. 234-251; Wang R C, Levine B. Autophagy in cellular growth control. FEBS Lett. 584 (2010), pp 1417-1426; Xin Y, Li W, First EA. The 'KMSKS' motif in Tyrosyl-tRNA synthetase participates in the initial binding of tRNA. Tyr. Biochemistry 39(2002), pp. 340-347).

Through the structure-activity relationship studies, leucine analogues with a modified amino group, a modified carboxylic group, charged R groups, or bulkier aliphatic R groups lost mTORC1 agonist activity (Lynch C J, Fox H L, Vary T C, Jefferson L S, Kimball S R. Regulation of amino acid-sensitive TOR signaling by leucine analogues in adipocytes. J Cell Biochem. 77 (2000), pp. 234-251). However, since the effects of leucine analogues on leucylation or ATP-PPi exchange activity of LRS were not clearly determined and leucine analogues have different effects on mTORC1, further investigations are needed. In this study, we analyzed the effect of leucine analogues, leucinol and leucinamide, on leucine-induced S6K phosphorylation. The leucine analogue, leucinol, is a competitior against leucine (Lynch C J, Fox H L, Vary T C, Jefferson L S, Kimball S R. Regulation of amino acid-sensitive TOR signaling by leucine analogues in adipocytes. J Cell Biochem. 77 (2000), pp. 234-251), thereby inhibiting leucylation (Vaughan M H, Hansen B S. Control of initiation of protein synthesis in human cells. Evidence for a role of uncharged transfer rebonucleic acid, J Biol Chem. 248 (1973), pp. 7087-7096). Interestingly, leucinol itself had no effect on S6K phosphorylation, but inhibited leucine-induced S6K phosphorylation in dose-dependent manner in two different cell types (FIGS. 9a and 9b). In contrast, leucinamide itself significantly induced S6K phosphorylation and these effects were further increased in the presence of L-leucine (FIGS. 9a and 9b). Although the effects of leucine analogues varied, their effects were commonly disappeared by suppression of LRS (FIGS. 9c and 9d), further illustrating the significance of LRS for amino acid signaling.

To investigate whether tRNA charging activity of LRS is involved in RagD binding and mTORC1 activation, we performed in vitro competition assay using LRS substrates, leucine, ATP, and tRNA$^{Leu}$.

Interestingly, tRNA$^{Leu}$, but not ATP, significantly competed with RagD for LRS binding (FIG. 10a), suggesting that RagD and tRNA show exclusive access to LRS in vitro. To prove that interaction between LRS and RagD is independent of the leucylation activity, we made alanine mutant (K716A/K719A) of the conserved KMSKS motif which is an important for tRNA binding (FIG. 10b) (Hountondji C. Dessen P, Blanquet S. Sequence similarities among the family of aminoacyl-tRNA synthetases. biochimie 69 (1986), pp. 1071-1078; Xin Y, Li W, First EA. The 'KMSKS' motif in Tyrosyl-tRNA synthetase participates in the initial binding of tRNA. Tyr. Biochemistry 39(2002), pp. 340-347). Although this mutant showed little leucylation activity, it retained the ATP-PPi exchange activity (FIG. 10c). K716A/K719A mutant of LRS showed no difference from the wild type LRS its effect on RagB/RagD heterodimer formation (FIG. 10d) and leucine-induced mTORC1 activation (FIG. 10e), suggesting that the tRNA charging activity of LRS is not involved in mTORC1 activation.

A comparison between the $K_m$ value of leucine for LRS and the $EC_{50}$ for leucine stimulation of mTORC1 can give a clue to the involvement of LRS in mTORC1 signaling. The $EC_{50}$ for leucine stimulation of mTORC1 was about 80 µM in 293T cells (FIGS. 11a and 11b) and in HeLa cells (data not shown). In the absence of tRNA$^{Leu}$ (ATP-PPi exchange), the $K_m$ of leucine for LRS was 143±61 µM although the $K_m$ of leucine for LRS was 15.9±0.4 µM in the presence of tRNA$^{Leu}$ (leucylation) (FIG. 11c). Therefore, the $K_m$ of leucine for LRS in ATP-PPi exchange reaction is comparable to the $EC_{50}$ for leucine stimulation of mTORC1. These results clearly support that leucine, but not tRNA, binding to LRS is involved in RagD binding and mTORC1 activation.

6. LRS Interacts with GTP Form of RagD

Since Rag GTPases are Ras family GTP-binding proteins, mTORC1 activation and LRS binding can be affected by the GTP/GDP binding status of Rag GTPases. Indeed, it is known that heterodimers of GTP-bound RagA or B and GDP-bound RagC or D show strong binding to mTORC1 (Sancak Y, Peterson T R, Shaul Y D, Lindquist R A, Thoreen C C, Bar-Peled L, Sabatini D M. The Rag GTPases bind raptor and mediate amino acid signaling to mTORC1. Science 320 (2008), pp. 1496-1501; Kim E, Goraksha-Hicks P, Li L, Neufeld T P, Guan K L. Regulation of TORC1 by Rag GTPases in nutrient response. Nat Cell Biol. 10 (2008), pp. 935-945). Among heterodimers of Rag GTPases, heterodimer of GTPbound RagB and GDP-bound RagD, which interacted strongly with mTORC1, not only activate mTORC1 pathway, but also make it insensitive to deprivation of leucine or amino acids (Sancak Y, Peterson T R, Shaul Y D, Lindquist R A, Thoreen C C, Bar-Peled L, Sabatini D M. The Rag GTPases bind raptor and mediate amino acid signaling to mTORC1. Science 320 (2008), pp. 1496-1501). Consistently, we also observed that the combination of GTP-bound RagB and GDP-bound RagD showed the highest effect on S6K phosphorylation in response to leucine and amino acids (FIGS. 6a and 6b).

We examined whether the GTP/GDP status of RagD can affect LRS binding. HA-RagD transfected 293T cell lysates were incubated with GST or GST-LRS in the presence of GDPβS or GTPγS, followed by immunoblot analysis. GDPβS, but not GTPγS, significantly reduced the binding affinity of LRS to RagD (FIG. 6c). We again performed in vitro binding assay using myc-tagged RagD WT, GTP-bound form (Q121L), or GDP-bound form (S77L)-transfected cells. Consistently, S77L mutant of RagD showed lower affinity for LRS (FIG. 6d), indicating that interaction between LRS and RagD is controlled by the GTP/GDP cycle of RagD. Since intracellular concentration of GTP is higher than GDP (Lowy, 1993), the GTP-form (Q121L) of RagD might show the binding affinity to LRS comparable with RagD WT. We investigated whether the binding of LRS to RagD would be affected by GTP/GDP status. Different forms of Myc-RagD (WT, GTP, and GDP forms) were expressed with FLAG-LRS in 293T cells and their binding to LRS was compared by coimmunoprecipitation of LRS with RagD. RagD Q121L showed higher affinity for LRS than RagD WT, but RagD S77L had very weak binding to LRS (FIG. 6e). Next, we monitored the interaction between LRS and heterodimers of RagA/B and RagD upon GTP/GDP status of Rag GTPases.

Interestingly, the interaction between LRS and RagA/D or RagB/D heterodimer was determined by GTP/GDP status of RagD, but not of RagA or RagB (FIGS. 6f and 6g). GTP-bound RagD, but not GDP-bound RagD, tightly interacted with LRS. These results suggest that LRS has no effect on GTP/GDP cycle of RagA or RagB and that LRS dynamically associated with GTP-bound RagD and then dissociate from GDP-bound RagD when the bound GTP is changed into GDP due to its intrinsic GTPase activity. Since GTP form of RagD is inhibitory for mTORC1 activation, LRS appears to bind the inactive Rag heterodimer in order to facilitate GTP to GDP transition, and dissociate from the active Rag heterodimer for mTORC1 activation.

7. LRS Acts as GTPase-Activating Protein for RagD GTPase

Since LRS interacts with GTP form of RagD, but not with GDP form of RagD, we investigated whether LRS had GTPase-activating protein (GAP) function for RagD GTPase to activate mTORC1 pathway. First, we confirmed the amino acid-induced GTP/GDP status of RagD. Consistent with previous model, amino acid stimulation of cells increased the GDP form of RagD (FIG. 12). In in vitro GTPase assay, addition of WT LRS fragment (759-1176 a.a) enhanced GTP hydrolysis by RagD GTPase in dose- and time-dependent manner (FIGS. 7a and 7b), indicating that LRS has intrinsic GAP activity for RagD GTPase. Through amino acid sequence alignment, we found that LRS had putative GAP motif, which was found in several Arf-GAP proteins (FIG. 7c). To prove that this motif of LRS is indeed important for the GAP activity, we made alanine mutants (H844A and R845A) of putative LRS GAP motif. In in vitro GTPase assay, H844A and R845A mutants lost their GAP activity while WT LRS showed GAP activity (FIG. 7d). Next, we examined the effect of H844A or R845A mutation on leucine-induced mTORC1 activation. While WT LRS enhanced leucine-induced S6K phosphorylation, H884A and R845A mutant lost their activities. These results clearly indicate that LRS functions as a GAP for RagD GTPase to activate mTORC1 activation. Combined together, the binding of LRS to ARS complex in the cytoplasm and to RagD GTPase in the lysosome may take place independently. Lysosomal LRS interacts with RagD and facilitates the conversion of the inactive heterodimer of Rag GTPases into the active form, leading to the activation of mTORC1 (FIG. 7e).

8. ELISA Assay for Measuring Binding Affinity Between LRS and RagD.

Purified GST-RagD was incubated with His-LRS-(1-1176) coated on a plate at various concentrations and was subjected to ELISA using anti-GST antibody, and the results of the ELISA are shown in FIGS. 13A and 13b. As a result, it was shown that RagD was bound to LRS.

In addition, when His-LRS-(759-1176) was added during the process of incubating GST-RagD with His-LRS-(1-

1176) coated on the plate, the binding between RagD and LRS was inhibited, suggesting that a region of residues 759-1176 of LRS is involved in binding with RagD to inhibit the binding between LRS-(1-1176) and RagD. In addition, it could be seen that such results of ELISA by the protein overlay method are results with specificity.

Application Example 1

Anticancer and Antitumor

It was found that a large number of human cancers (lymphoma, melanoma, breast cancer, ovarian cancer, prostate cancer, stomach cancer, and head and neck cancers) have mutant genes translated in the mTOR pathway (Guertin, D. et al., An expanding role for mTOR in cancer. Trends Mol. Med. 11(2005), pp 353-361). The test agent of the present invention, which inhibits the binding between LRS and RagD, can be used as an anticancer agent which inhibits the mTOR pathway to inhibit the occurrence of a mutant gene caused by translation in the mTOR pathway.

Application Example 2

Anti-Obesity

The mTOR pathway is known to be involved in lipid metabolisms, and it was found that the excessive production of lipids by the over-expression of preadipocytes leads to an increase in the activity of the mTOR pathway (Kim, J. E and Chen, J, Regulation of peroxisome proliferator-activated receptor-γ activity by mammalian target of rapamycin and amino acids in adipogenesis, Diabetes, 52(2004), pp 1748-1756; Cho, H. et al., Regulation of adipocyte differentiation and insulin action with rapamycin. Biochem. biophys. Res. Cmmun., 321(2004), pp 942-948)). Particularly, it was found that the mTOR pathway is highly involved in the accumulation of lipids and the growth of adipocytes (Um, S. et al., Absence of S6K1 protects against age- and diet-induced obesity while enhancing insulin sensitivity, Nature, 431(2004), pp 200-205). The test agent of the present invention inhibits the activity of the mTOR pathway, suggesting it is effective against excessive lipid production and lipid accumulation, which influence obesity.

What is claimed is:

1. A method for screening for an agent for treating mTORC1 (mammalian target of rapamycin complex 1)-mediated diseases, the method comprising:
   applying test agents to mixtures comprising LRS (Leucyl tRNA synthetase) and RagD (RagD GTPase) to provide test mixtures;
   measuring a binding affinity between LRS and RagD in each of the test mixtures;
   comparing the measured binding affinity between LRS and RagD in each of the test mixtures with the test agents applied thereto, to a binding affinity between LRS and RagD in a control mixture without a test agent, wherein a decrease in binding affinity between LRS and RagD in at least one of the test mixtures in comparison to the control mixture provides an indication that at least one of the test agents in the at least one test mixture inhibits binding affinity between LRS and RagD;
   identifying the at least one test agent in the at least one test mixture that inhibits the binding affinity between LRS and RagD, based on the comparison; and
   evaluating the at least one test agent in the at least one test mixture that inhibits the binding affinity between LRS and RagD as an agent for treating a mTORC1-mediated disease selected from the group consisting of cancer, autoimmune disease, diabetes, obesity, and cardiovascular disease.

* * * * *

SEQUENCE LISTING

<160> NUMBER OF SEQ ID NOS: 22

<210> SEQ ID NO 1
<211> LENGTH: 1176
<212> TYPE: PRT
<213> ORGANISM: Homo sapiens

<400> SEQUENCE: 1

```
Met Ala Glu Arg Lys Gly Thr Ala Lys Val Asp Phe Leu Lys Lys Ile
  1               5                  10                  15

Glu Lys Glu Ile Gln Gln Lys Trp Asp Thr Glu Arg Val Phe Glu Val
             20                  25                  30

Asn Ala Ser Asn Leu Glu Lys Gln Thr Ser Lys Gly Lys Tyr Phe Val
         35                  40                  45

Thr Phe Pro Tyr Pro Tyr Met Asn Gly Arg Leu His Leu Gly His Thr
     50                  55                  60

Phe Ser Leu Ser Lys Cys Glu Phe Ala Val Gly Tyr Gln Arg Leu Lys
 65                  70                  75                  80

Gly Lys Cys Cys Leu Phe Pro Phe Gly Leu His Cys Thr Gly Met Pro
                 85                  90                  95

Ile Lys Ala Cys Ala Asp Lys Leu Lys Arg Glu Ile Glu Leu Tyr Gly
            100                 105                 110

Cys Pro Pro Asp Phe Pro Asp Glu Glu Glu Glu Glu Glu Glu Thr Ser
        115                 120                 125

Val Lys Thr Glu Asp Ile Ile Ile Lys Asp Lys Ala Lys Gly Lys Lys
    130                 135                 140

Ser Lys Ala Ala Ala Lys Ala Gly Ser Ser Lys Tyr Gln Trp Gly Ile
145                 150                 155                 160

Met Lys Ser Leu Gly Leu Ser Asp Glu Glu Ile Val Lys Phe Ser Glu
                165                 170                 175

Ala Glu His Trp Leu Asp Tyr Phe Pro Pro Leu Ala Ile Gln Asp Leu
            180                 185                 190

Lys Arg Met Gly Leu Lys Val Asp Trp Arg Arg Ser Phe Ile Thr Thr
        195                 200                 205

Asp Val Asn Pro Tyr Tyr Asp Ser Phe Val Arg Trp Gln Phe Leu Thr
    210                 215                 220
```

```
Leu Arg Glu Arg Asn Lys Ile Lys Phe Gly Lys Arg Tyr Thr Ile Tyr
225                 230                 235                 240

Ser Pro Lys Asp Gly Gln Pro Cys Met Asp His Asp Arg Gln Thr Gly
            245                 250                 255

Glu Gly Val Gly Pro Gln Glu Tyr Thr Leu Leu Lys Leu Lys Val Leu
        260                 265                 270

Glu Pro Tyr Pro Ser Lys Leu Ser Gly Leu Lys Gly Lys Asn Ile Phe
        275                 280                 285

Leu Val Ala Ala Thr Leu Arg Pro Glu Thr Met Phe Gly Gln Thr Asn
290                 295                 300

Cys Trp Val Arg Pro Asp Met Lys Tyr Ile Gly Phe Glu Thr Val Asn
305                 310                 315                 320

Gly Asp Ile Phe Ile Cys Thr Gln Lys Ala Ala Arg Asn Met Ser Tyr
                325                 330                 335

Gln Gly Phe Thr Lys Asp Asn Gly Val Val Pro Val Val Lys Glu Leu
            340                 345                 350

Met Gly Glu Glu Ile Leu Gly Ala Ser Leu Ser Ala Pro Leu Thr Ser
        355                 360                 365

Tyr Lys Val Ile Tyr Val Leu Pro Met Leu Thr Ile Lys Glu Asp Lys
        370                 375                 380

Gly Thr Gly Val Val Thr Ser Val Pro Ser Asp Ser Pro Asp Asp Ile
385                 390                 395                 400

Ala Ala Leu Arg Asp Leu Lys Lys Lys Gln Ala Leu Arg Ala Lys Tyr
                405                 410                 415

Gly Ile Arg Asp Asp Met Val Leu Pro Phe Glu Pro Val Pro Val Ile
            420                 425                 430

Glu Ile Pro Gly Phe Gly Asn Leu Ser Ala Val Thr Ile Cys Asp Glu
        435                 440                 445

Leu Lys Ile Gln Ser Gln Asn Asp Arg Glu Lys Leu Ala Glu Ala Lys
        450                 455                 460

Glu Lys Ile Tyr Leu Lys Gly Phe Tyr Glu Gly Ile Met Leu Val Asp
465                 470                 475                 480

Gly Phe Lys Gly Gln Lys Val Gln Asp Val Lys Lys Thr Ile Gln Lys
                485                 490                 495

Lys Met Ile Asp Ala Gly Asp Ala Leu Ile Tyr Met Glu Pro Glu Lys
            500                 505                 510

Gln Val Met Ser Arg Ser Ser Asp Glu Cys Val Val Ala Leu Cys Asp
        515                 520                 525

Gln Trp Tyr Leu Asp Tyr Gly Glu Glu Asn Trp Lys Lys Gln Thr Ser
530                 535                 540

Gln Cys Leu Lys Asn Leu Glu Thr Phe Cys Glu Glu Thr Arg Arg Asn
545                 550                 555                 560

Phe Glu Ala Thr Leu Gly Trp Leu Gln Glu His Ala Cys Ser Arg Thr
                565                 570                 575

Tyr Gly Leu Gly Thr His Leu Pro Trp Asp Glu Gln Trp Leu Ile Glu
            580                 585                 590

Ser Leu Ser Asp Ser Thr Ile Tyr Met Ala Phe Tyr Thr Val Ala His
        595                 600                 605

Leu Leu Gln Gly Gly Asn Leu His Gly Gln Ala Glu Ser Pro Leu Gly
        610                 615                 620

Ile Arg Pro Gln Gln Met Thr Lys Glu Val Trp Asp Tyr Val Phe Phe
625                 630                 635                 640

Lys Glu Ala Pro Phe Pro Lys Thr Gln Ile Ala Lys Glu Lys Leu Asp
```

-continued

```
                645                 650                 655
Gln Leu Lys Gln Glu Phe Glu Phe Trp Tyr Pro Val Asp Leu Arg Val
            660                 665                 670
Ser Gly Lys Asp Leu Val Pro Asn His Leu Ser Tyr Tyr Leu Tyr Asn
            675                 680                 685
His Val Ala Met Trp Pro Glu Gln Ser Asp Lys Trp Pro Thr Ala Val
690                 695                 700
Arg Ala Asn Gly His Leu Leu Leu Asn Ser Glu Lys Met Ser Lys Ser
705                 710                 715                 720
Thr Gly Asn Phe Leu Thr Leu Thr Gln Ala Ile Asp Lys Phe Ser Ala
                725                 730                 735
Asp Gly Met Arg Leu Ala Leu Ala Asp Ala Gly Asp Thr Val Glu Asp
            740                 745                 750
Ala Asn Phe Val Glu Ala Met Ala Asp Ala Gly Ile Leu Arg Leu Tyr
            755                 760                 765
Thr Trp Val Glu Trp Val Lys Glu Met Val Ala Asn Trp Asp Ser Leu
            770                 775                 780
Arg Ser Gly Pro Ala Ser Thr Phe Asn Asp Arg Val Phe Ala Ser Glu
785                 790                 795                 800
Leu Asn Ala Gly Ile Ile Lys Thr Asp Gln Asn Tyr Glu Lys Met Met
                805                 810                 815
Phe Lys Glu Ala Leu Lys Thr Gly Phe Phe Glu Phe Gln Ala Ala Lys
            820                 825                 830
Asp Lys Tyr Arg Glu Leu Ala Val Glu Gly Met His Arg Glu Leu Val
            835                 840                 845
Phe Arg Phe Ile Glu Val Gln Thr Leu Leu Leu Ala Pro Phe Cys Pro
850                 855                 860
His Leu Cys Glu His Ile Trp Thr Leu Leu Gly Lys Pro Asp Ser Ile
865                 870                 875                 880
Met Asn Ala Ser Trp Pro Val Ala Gly Pro Val Asn Glu Val Leu Ile
                885                 890                 895
His Ser Ser Gln Tyr Leu Met Glu Val Thr His Asp Leu Arg Leu Arg
            900                 905                 910
Leu Lys Asn Tyr Met Met Pro Ala Lys Gly Lys Lys Thr Asp Lys Gln
            915                 920                 925
Pro Leu Gln Lys Pro Ser His Cys Thr Ile Tyr Val Ala Lys Asn Tyr
930                 935                 940
Pro Pro Trp Gln His Thr Thr Leu Ser Val Leu Arg Lys His Phe Glu
945                 950                 955                 960
Ala Asn Asn Gly Lys Leu Pro Asp Asn Lys Val Ile Ala Ser Glu Leu
                965                 970                 975
Gly Ser Met Pro Glu Leu Lys Lys Tyr Met Lys Lys Val Met Pro Phe
            980                 985                 990
Val Ala Met Ile Lys Glu Asn Leu Glu Lys Met Gly Pro Arg Ile Leu
            995                 1000                1005
Asp Leu Gln Leu Glu Phe Asp Glu Lys Ala Val Leu Met Glu Asn Ile
    1010                1015                1020
Val Tyr Leu Thr Asn Ser Leu Glu Leu Glu His Ile Glu Val Lys Phe
1025                1030                1035                1040
Ala Ser Glu Ala Glu Asp Lys Ile Arg Glu Asp Cys Cys Pro Gly Lys
                1045                1050                1055
Pro Leu Asn Val Phe Arg Ile Glu Pro Gly Val Ser Val Ser Leu Val
            1060                1065                1070
```

```
Asn Pro Gln Pro Ser Asn Gly His Phe Ser Thr Lys Ile Glu Ile Arg
        1075                1080                1085

Gln Gly Asp Asn Cys Asp Ser Ile Ile Arg Arg Leu Met Lys Met Asn
    1090                1095                1100

Arg Gly Ile Lys Asp Leu Ser Lys Val Lys Leu Met Arg Phe Asp Asp
1105                1110                1115                1120

Pro Leu Leu Gly Pro Arg Arg Val Pro Val Leu Gly Lys Glu Tyr Thr
                1125                1130                1135

Glu Lys Thr Pro Ile Ser Glu His Ala Val Phe Asn Val Asp Leu Met
            1140                1145                1150

Ser Lys Lys Ile His Leu Thr Glu Asn Gly Ile Arg Val Asp Ile Gly
        1155                1160                1165

Asp Thr Ile Ile Tyr Leu Val His
    1170                1175

<210> SEQ ID NO 2
<211> LENGTH: 25
<212> TYPE: DNA
<213> ORGANISM: Artificial Sequence
<220> FEATURE:
<223> OTHER INFORMATION: Homo sapiens

<400> SEQUENCE: 2
ggaaguaccc uacuuugcuu gaggu                                           25

<210> SEQ ID NO 3
<211> LENGTH: 4926
<212> TYPE: DNA
<213> ORGANISM: Artificial Sequence
<220> FEATURE:
<223> OTHER INFORMATION: Homo sapiens

<400> SEQUENCE: 3
cgcagtctct ctctctctcc ctcctccggg aggaactgcc gcgctccggc tgactcctcc      60
gccggcgggc ggggcggggg aggggcttc gggcgcgctg ggaaccgcgg gacccggacc      120
tgggcgccgc ccgccggggg acgcgcggcc cccgcttccg ccgggccccg ctgagctcta     180
gacaaacctc cgcttcagaa ataggctgcg gcggccggc taggaggctt ggcccccacc      240
ccgggacccc cgccgtcccc gggcggccg ccggtgggc acgatgagcc aggtgctggg       300
gaagccgcag ccgcaggacg aggacgacgc ggaggaggag gaggaggagg atgagctggt     360
ggggctagcg gactacggag acgggcccga ctcctccgac gccgatccgg acagcggcac     420
agaggaggga gttctggact tcagtgaccc cttcagcact gaagtgaagc cgagaatcct     480
gctcatgggc ctgaggagaa gcggcaagtc gtctattcag aaagttgtct ttcacaaaat     540
gtctcccaac gaaactctgt tcttggagag cactaataag atatgccggg aagatgtttc     600
caacagctcc tttgtcaatt ttcagatttg ggacttccca ggacagatt acttttttga     660 ccctacattt gactatgaga tgatcttccg gggaacagga gcactgatat tgtcattga      720 ctcacaggat gattacatgg aagccctggc caggctccac ctcacggtga ccagggccta     780
caaagtgaat actgacatca acttcgaggt gtttattcat aaagtggatg gtctgtcaga     840
tgaccacaaa attgaaaccc aaagagatat tcaccagagg gcaaacgatg accttgcaga     900
tgctggatta gaaaaaattc acctcagctt ttatctgaca agcatatatg atcattcaat     960
atttgaagct tttagcaaag ttgttcagaa actgattcca caactcccaa ctctggaaa     1020 tttgctgaac atctttatct caaattctgg aattgaaaag gcatttctat tgatgtggt     1080
```

```
cagtaaaatt tatattgcaa ctgatagtac tccggtggat atgcaaacct atgagctctg    1140
ctgtgatatg atagatgtgg ttattgacat ctcttgtatt tatggtctca aagaagatgg    1200
agcaggaacc ccctatgaca aggaatccac agccatcata aagcttaata atacaaccgt    1260
gctttattta aaagaggtga caaagttcct ggctctcgtt tgctttgtca gagaggaaag    1320
ctttgaaaga aaagggctaa ttgactataa ttttcattgc ttccggaagg ccattcatga    1380 agttttgag gtgagaatga aagtagtaaa atctcgaaag gttcagaatc ggctgcagaa    1440 gaaaagaga gccaccccta atgggacccc tagagtgctg ctgtaggtga ggtttcagga    1500
atgtcttttg aaatcagacc ttatccatga ggctgctgcg ccatgttgca ctaaaggaag    1560
aggaagaagg agattgggac ataccatt gatttgttgt taaaaaaaaa aaattcctgc    1620
aaccctcttg atcttctctt ttataaataa agtaagcact ttgaagcaaa aacttgtata    1680
ttaacagtga tgtgaaatcc attgtcattt cattacacaa atgtaaactt ttatggtctg    1740
tagtcaaaaa aatcccgtgt gagaactgcc aggaattgta catattttgc acttttcat     1800 gtttctcatt gaactgaact ttgataaaac gacttttcta agctttttt ctgtacttgg     1860 tgtcaaggac atgcatactg tagtccatat ctatatggca atcagaaatt aatcaaaaag    1920
tgatgcattg gtaatgactt tttgtaaatt tggaaatctt tgctaccaat tgttgagaaa    1980
aatcattttt cagtggagct ggaacagatt ggagctacaa gctccaggag caataagaac    2040
tgtcccctat ttataatggg tgtaaacagt tttgtagaat aatgctagca ccagacttac    2100
ctaaaaattt ctatagcagt ggctgtgctt ccctgctcaa cggttttttat gaagctgttt    2160 acctcaacac acatctctat aatcacttta tacagagagg ttatttcttt ttgttgcatt    2220
agtattcttt tgaaactttg ggaccagatt tccaaaatgg tgccgaacac tggagagaag    2280
taagaatgtc actgaattgt agggtttctg gaggcttttc tgtacctacc acccagggct    2340
aaagtaacat cagaggccta aagttgttcc aaaagtatgt gattggcaac tgcagactaa    2400
aaaacataga tacaattctg gacttttggc cctgtgcgat ggtctggtgt gctgcattta    2460
aaatgcttat tcaggaccag ttctttattg ctccatgacc atagtgaata gaacaaatcg    2520 cagaaccca ccatggagct caatcctgtt agtcactttt gtcacctcca catctccttc    2580
tcactggtga taacatgcct catgtactcc acttgttccc acctatgat taagccaagc    2640 tcagcctgcc accagcatgc tctgcaaggc tgaagagtca tcctgaagac ccctaaaggt    2700
cagtgggaaa aggatggctg gagagacatt acaattagct gtgtaattgt ttctgtgaaa    2760
ttatttcact tatgtttact ttagactaac aggaaattaa gagtcctaaa tctacccta     2820 tgccaaatca ttccaagtag ataatttac gtgcatctca agggttagca ccctaaggca    2880
tgcttgtggg gcattagaaa atgagatttt tttttttta aagcagagcc tcctaagaac     2940
atcaaagttg gtcctagcaa aatatataaa gtccctaaag caacttatac ttgaaacttt    3000
tttttttttt tttttagag ggggcctca ttctgttgct tgtgctggaa tacattggta     3060
caatcatagc tcactgttac ctcttgggct caagggatcc ttccacctca gcctccctag    3120
tagctagaac tacaggtgtg cacaaccacg cccggctaat tcttaaattt tgttttgta     3180 gagacaggat ctcactgtgt tgcccaagat ggtctcaaac tcctggcccc aagcaatcct    3240
cctgccttgg cctcctcaaa tgctgagatt acaggcctga gctactgtgc ccagcctaaa    3300
cttccccact tctctctgtg gcttctttcc aacctctctc cttcctctcc ccaagtcctg    3360
tttctttgaa gctggtaact gaatttaaga tgatatctgg ttggtgttta aggtttgagc    3420
```

```
ctcccaaggt tctgtgcatt ttgaaaggag atttctaaaa ataattaagg tgccctaact    3480
cctttcctca tgattcctac tccgaaacct ggatggttag gagcccaggg ctccctgatt    3540
tccagagcta tatcctgttg gacctttgcc aacagacctg acacttaggg gttattgtta    3600
taaatctaat tctctaatat ttttacatg ttgtttcact ttgataagc aaatgaagaa      3660 tcagttttct aatatgactt tatcctcaag ctagagacac tagcctattt ggtaaatcac    3720
acattactta ggtatattta ttactataac caggttggag cttccatgtt taagctgggt    3780
atatgatggg ttttgttaa aatgtgcctt aaaaagccta ttacttcaag agcaaatgat     3840
tctttggggg aaaggcaaaa ataattctat gacatagggc ccaagttcat ggtagtaagt    3900
gtactctttg attaatcaca cgctaatata gattactgcc tctaactttg taagtgtggc    3960
aatgacttct taattaaaga agatgcagg agttatgtct aagcgttcag tttttcaaat     4020
ctgtgttatt ggaaatgtct tcaagtcatt ttgcattgta tttttgatat gagaggcagc    4080
ttattgcgat gtgtatggcc atgtttcatt ctcaaattta attctataaa tacaaatcct    4140
aaatacatgg ctacagcaac tgcactggaa cattttgct tggttttagg gattgagaac     4200
ttgccttgca ggtttccttc ctcaaaagga gcagggcagt cctttccctg ttgagtcaat    4260
tagaattttt acatagaggt gagactgtga attattttgg ttatttcag tgatgtagat     4320 tagtgtgaat gaccagggtg gaatgttttt gaaggaatat aaagcaaaaa ctggttgaca    4380
ttcacaaact gttcttttgt gaacatattt tggacccta aatatgacta aaatcacagc     4440
aatattgtta catcgggtt atatgccaac tctgtttgaa atatactctg gaaaacagc      4500 tgaattgtct tggttattaa agtatggtat gtattcaact tgtacagact ggatgtaatt    4560
tgtaatcagg tatagtccat gttttacttt aagcagtaca tcacttaata accattgtta    4620
agccattgct ttcaagaatg ttaactgcca atttaaaagc atgtgtccta ggttcatgct    4680
ttggtaaagc tctcatttca agtgtattca tagctaagct ttctgggagc agaattgtct    4740
ctttggtgaa aaggaagtac agcctttcct gtttctgagg ttgcttacca tacatgtatg    4800
tcactgtttc attggcccctg ttacatccat ttggtaaaat ttatttgtcc tgattaacca   4860
gctctcattt tatggaaatg atgataaatc tcactactta aatttaattt atgcttttat    4920
ttttaa                                                               4926
```

<210> SEQ ID NO 4
<211> LENGTH: 39
<212> TYPE: DNA
<213> ORGANISM: Artificial Sequence
<220> FEATURE:
<223> OTHER INFORMATION: LRS-(1-1176)sense

<400> SEQUENCE: 4

```
ggaattccat atggcggaaa gaaaaggaac agccaaagt                             39
```

<210> SEQ ID NO 5
<211> LENGTH: 36
<212> TYPE: DNA
<213> ORGANISM: Artificial Sequence
<220> FEATURE:
<223> OTHER INFORMATION: LRS-(1-1176)antisense

<400> SEQUENCE: 5

```
cgggatcctt aatgaaccag atagattatt gtatcg                                36
```

<210> SEQ ID NO 6
<211> LENGTH: 33

```
<212> TYPE: DNA
<213> ORGANISM: Artificial Sequence
<220> FEATURE:
<223> OTHER INFORMATION: LRS-(759-1176)sense

<400> SEQUENCE: 6
ggaattccat atggcagatg caggtattct ccg                               33

<210> SEQ ID NO 7
<211> LENGTH: 29
<212> TYPE: DNA
<213> ORGANISM: Artificial Sequence
<220> FEATURE:
<223> OTHER INFORMATION: RagD-(1-400)sense

<400> SEQUENCE: 7
cgggatccat gagccaggtg ctggggaag                                    29

<210> SEQ ID NO 8
<211> LENGTH: 30
<212> TYPE: DNA
<213> ORGANISM: Artificial Sequence
<220> FEATURE:
<223> OTHER INFORMATION: RagD-(1-400)antisense

<400> SEQUENCE: 8
cgctcgagct acagcagcac tctaggggtc                                   30

<210> SEQ ID NO 9
<211> LENGTH: 25
<212> TYPE: DNA
<213> ORGANISM: Artificial Sequence
<220> FEATURE:
<223> OTHER INFORMATION: 105(5'UTR)

<400> SEQUENCE: 9
cagcaggugu gaagcgugug cuuua                                        25

<210> SEQ ID NO 10
<211> LENGTH: 25
<212> TYPE: DNA
<213> ORGANISM: Artificial Sequence
<220> FEATURE:
<223> OTHER INFORMATION: 195(5'UTR)

<400> SEQUENCE: 10
ccagggucau ugucguggau uugca                                        25

<210> SEQ ID NO 11
<211> LENGTH: 25
<212> TYPE: DNA
<213> ORGANISM: Artificial Sequence
<220> FEATURE:
<223> OTHER INFORMATION: 396(CDS)

<400> SEQUENCE: 11
cauauaugaa uggacgccuu cauuu                                        25

<210> SEQ ID NO 12
<211> LENGTH: 25
<212> TYPE: DNA
<213> ORGANISM: Artificial Sequence
<220> FEATURE:
<223> OTHER INFORMATION: 792(CDS)

<400> SEQUENCE: 12
```
cgccacuggc uauucaggau uuaaa                                              25

<210> SEQ ID NO 13
<211> LENGTH: 25
<212> TYPE: DNA
<213> ORGANISM: Artificial Sequence
<220> FEATURE:
<223> OTHER INFORMATION: 1312(CDS)

<400> SEQUENCE: 13
uggugcauca cuuucugcac cuuua                                              25

<210> SEQ ID NO 14
<211> LENGTH: 25
<212> TYPE: DNA
<213> ORGANISM: Artificial Sequence
<220> FEATURE:
<223> OTHER INFORMATION: 3844(3'UTR)

<400> SEQUENCE: 14
cagaaccuua ggcuggaccu aaaua                                              25

<210> SEQ ID NO 15
<211> LENGTH: 25
<212> TYPE: DNA
<213> ORGANISM: Artificial Sequence
<220> FEATURE:
<223> OTHER INFORMATION: mTOR

<400> SEQUENCE: 15
ggaaguaccc uacuuugcuu gaggu                                              25

<210> SEQ ID NO 16
<211> LENGTH: 25
<212> TYPE: DNA
<213> ORGANISM: Artificial Sequence
<220> FEATURE:
<223> OTHER INFORMATION: IRS

<400> SEQUENCE: 16
ggaagccaga ugucagccc ucuau                                               25

<210> SEQ ID NO 17
<211> LENGTH: 25
<212> TYPE: DNA
<213> ORGANISM: Artificial Sequence
<220> FEATURE:
<223> OTHER INFORMATION: VRS

<400> SEQUENCE: 17
agaagaggau gucaugaccg gucuc                                              25

<210> SEQ ID NO 18
<211> LENGTH: 25
<212> TYPE: DNA
<213> ORGANISM: Artificial Sequence
<220> FEATURE:
<223> OTHER INFORMATION: MRS

<400> SEQUENCE: 18
cuaccgcugg uuuaacauuu cguuu                                              25

<210> SEQ ID NO 19
<211> LENGTH: 20
<212> TYPE: DNA
<213> ORGANISM: Artificial Sequence

```
<220> FEATURE:
<223> OTHER INFORMATION: RagC, Sense

<400> SEQUENCE: 19
tcggctacgg cgtggaggag                                               20

<210> SEQ ID NO 20
<211> LENGTH: 20
<212> TYPE: DNA
<213> ORGANISM: Artificial Sequence
<220> FEATURE:
<223> OTHER INFORMATION: RagC, Antisense

<400> SEQUENCE: 20 cgcccccgg accacagcca                                                20

<210> SEQ ID NO 21
<211> LENGTH: 20
<212> TYPE: DNA
<213> ORGANISM: Artificial Sequence
<220> FEATURE:
<223> OTHER INFORMATION: RagD, Sense

<400> SEQUENCE: 21
tgagctggtg gggctagcgg                                               20

<210> SEQ ID NO 22
<211> LENGTH: 22
<212> TYPE: DNA
<213> ORGANISM: Artificial Sequence
<220> FEATURE:
<223> OTHER INFORMATION: RagD, Antisense

<400> SEQUENCE: 22
gggtcactga agtccagaac tc                                            22
```